US012009064B2

(12) United States Patent
Gibson et al.

(10) Patent No.: US 12,009,064 B2
(45) Date of Patent: *Jun. 11, 2024

(54) SYSTEMS AND METHODS FOR HIGH THROUGHPUT COMPOUND LIBRARY CREATION

(71) Applicant: Recursion Pharmaceuticals, Inc., Salt Lake City, UT (US)

(72) Inventors: Chris Gibson, Salt Lake City, UT (US); Blake C. Borgeson, San Francisco, CA (US); Mason L. Victors, Sandy, UT (US); David Healey, Provo, UT (US); Ian Quigley, Salt Lake City, UT (US); Ronald Wakim Alfa, Salt Lake City, UT (US)

(73) Assignee: Recursion Pharmaceuticals, Inc., Salt Lake City, UT (US)

( * ) Notice: Subject to any disclaimer, the term of this patent is extended or adjusted under 35 U.S.C. 154(b) by 478 days.

This patent is subject to a terminal disclaimer.

(21) Appl. No.: 17/292,798

(22) PCT Filed: Nov. 13, 2019

(86) PCT No.: PCT/US2019/061275
§ 371 (c)(1),
(2) Date: May 11, 2021

(87) PCT Pub. No.: WO2020/102419
PCT Pub. Date: May 22, 2020

(65) Prior Publication Data
US 2021/0398619 A1    Dec. 23, 2021

Related U.S. Application Data

(63) Continuation of application No. 16/190,946, filed on Nov. 14, 2018, now Pat. No. 11,393,560.
(Continued)

(51) Int. Cl.
*G16C 20/20* (2019.01)
*G06F 17/16* (2006.01)
*G16C 20/40* (2019.01)

(52) U.S. Cl.
CPC ............. *G16C 20/20* (2019.02); *G06F 17/16* (2013.01); *G16C 20/40* (2019.02)

(58) Field of Classification Search
None
See application file for complete search history.

(56) References Cited

U.S. PATENT DOCUMENTS 7,416,524 B1   8/2008  Labanov et al.
11,393,560 B2  7/2022  Gibson et al.
(Continued)

FOREIGN PATENT DOCUMENTS

WO   2020102419 A1   5/2020

OTHER PUBLICATIONS

PCT/US2019/061275, International Searching Authority, International Search Report & Written Opinion, dated Jan. 20, 2020, 8 pgs. , dated Jan. 29, 2020.
(Continued)

*Primary Examiner* — Roy Y Yi

(57) ABSTRACT

The disclosure provides methods and systems for identifying a subset of compounds in a plurality of compounds. The identifying includes obtaining, for each compound, a vector including a set of elements, where each element includes a measurement of a different feature of an instance of a cell context upon exposure to the compound. The identifying includes performing the obtaining for a plurality of cell contexts, to obtain a plurality of vectors for each compound across different cell contexts. The identifying includes combining the vectors for each compound to form a combined vector for each compound, thereby forming a plurality of
(Continued)

combined vectors representing different compounds. The identifying includes pruning the plurality of compounds to the subset of compounds based on a similarity between respective combined vectors in the plurality of combined vectors corresponding to compounds in the plurality of compounds.

20 Claims, 12 Drawing Sheets

Related U.S. Application Data

(60) Provisional application No. 62/760,686, filed on Nov. 13, 2018.

(56) References Cited

U.S. PATENT DOCUMENTS

| | | |
|---|---|---|
| 11,791,019 B2 | 10/2023 | Gibson et al. |
| 2003/0104523 A1 | 6/2003 | Bauer et al. |
| 2004/0265909 A1 | 12/2004 | Blaney et al. |
| 2015/0273010 A1 | 10/2015 | Wolkowicz et al. |
| 2018/0148799 A1 | 5/2018 | Benenson et al. |
| 2020/0152295 A1 | 5/2020 | Gibson et al. |
| 2021/0398619 A1 | 12/2021 | Gibson et al. |
| 2022/0406414 A1 | 12/2022 | Gibson et al. |
| 2024/0029832 A1 | 1/2024 | Gibson et al. |

OTHER PUBLICATIONS

Gustafsdottir, et al., "Multiplex Cytological Profiling Assay to Measure Diverse Cellular States", PLOS/one, vol. 8, Issue 12, Dec. 2013.

Anonymous: "Cosine similarity—Wikipedia" Retrieved from the Internet: ORL:https://en.wikipeclia.org/w/index.php?titl.e=Cosine_simil.arity&ol.did=863396027 [retrieved on Jul. 10, 2019]; Oct. 10, 2018, 6 pages.

Bray et al. "Cell Painting, a high-content image-based assay for morphological profiling using multiplexed fluorescent dyes" Nature Protocols, vol. 11, No. 9; Aug. 25, 2016, pp. 1757-1774.

European Patent Application No. 37665EP; "European Extended Search Report" dated Jul. 7, 2022; 9 pages.

Petrone et al. "Biodiversity small molecules—a new perspective in screening set selection" Drug Discovery Today, vol. 18, No. 13-14; Jul. 1, 2013, pp. 674-680.

Weber, "Current Status of Virtual Combinatorial Library Design" QSAR & Combinatorial Science, vol. 24 No. 7; Sep. 19, 2005, pp. 809-823.

100

```
┌─────────────────────────────────────────────────────────────────┐
│ 102  Measure features of a plurality of test instances in one   │
│      or more cell context for each compound in a test compound  │
│      library                                                    │
│  ┌───────────────────────────────────────────────────────────┐  │
│  │ 104  Standardize measurements against a control instance  │  │
│  └───────────────────────────────────────────────────────────┘  │
└─────────────────────────────────────────────────────────────────┘
```

```
┌─────────────────────────────────────────────────────────────────┐
│ 106  Generate multi-dimensional vectors based on measurements   │
│      of each test instance in a cell context for each compound  │
└─────────────────────────────────────────────────────────────────┘

┌─────────────────────────────────────────────────────────────────┐
│ 108  Select a subset of compounds based on a geometric          │
│      relationship between multi-dimensional vectors             │
│      corresponding to the same compound                         │
│  ┌───────────────────────────────────────────────────────────┐  │
│  │ 110  Reduce dimensions of multi-dimensional vectors       │  │
│  └───────────────────────────────────────────────────────────┘  │
│  ┌───────────────────────────────────────────────────────────┐  │
│  │ 112  Whiten dimension-reduced vectors against control     │  │
│  │      instances                                            │  │
│  └───────────────────────────────────────────────────────────┘  │
│  ┌───────────────────────────────────────────────────────────┐  │
│  │ 114  Standardize whitened vectors against control         │  │
│  │      instances                                            │  │
│  └───────────────────────────────────────────────────────────┘  │
│  ┌───────────────────────────────────────────────────────────┐  │
│  │ 116  Filter-out compounds with disparate effects          │  │
│  └───────────────────────────────────────────────────────────┘  │
└─────────────────────────────────────────────────────────────────┘
```

402 Obtain, for each respective compound in the plurality of compounds, a corresponding vector, thereby obtaining a corresponding plurality of vectors

404 Each respective vector in the corresponding plurality of vectors comprises a corresponding set of elements

406 Each respective element in the corresponding set of elements comprises a measurement of a different feature in a plurality of features, across a plurality of instances of a cell context in a plurality of cell contexts upon exposure of an amount of the respective compound to the plurality of instances of the cell context using one or more multi-well plates comprising a plurality of wells

408 The measurement of the different feature in the plurality of features is a fluorescent microscopy measurement of the different feature

410 The measurement of the different feature in the plurality of features is a bright field measurement of the different feature

412 The measurement of the different feature in the plurality of features is phase contrast measurement of the different feature

414 Each feature in the plurality of features represents a color, texture, or size of the cell or an enumerated portion of the cell context upon exposure of the cell context to the amount of the respective compound

416 Each respective instance of the plurality of instances of the cell context is imaged to form a corresponding two-dimensional pixelated image having a corresponding plurality of native pixel values and wherein a feature in the plurality of features comprises a result of a convolution or a series convolutions and pooling operators run against native pixel values in the plurality of native pixel values of the corresponding two-dimensional pixelated image

417 Exposure of the respective compound to the plurality of instances of the cell context is done in the presence of one or more optical emitting entities

418 The one or more optical emitting compounds are dyes and the vector for a compound in the plurality of compounds includes respective measurements of features in the plurality of features for the cell context in the presence of each of at least three different dyes

420 The one or more optical emitting compounds are dyes and the vector for a compound in the plurality of compounds includes respective measurements of features in the plurality of features for the cell context in the presence of each of at least five different dyes 422 A first amount of the respective compound is tested in a first subset of the plurality of instances of the cell context, and a second amount of the respective compound is tested in a second subset of the plurality of instances of the cell context 424 The first subset of the plurality of instances is three instances, and the second subset of the plurality of instances is three instances 426 The first amount is 0.3 µM, and the second amount is 1 µM 428 A third amount of the respective compound is tested in a third subset of the plurality of instances of the cell context 430 The third subset of the plurality of instances is three instances 432 The third amount is 3 µM 434 The first amount of the respective compound is a first concentration of the respective compound, the second amount of the respective compound is a second concentration of the respective compound other than the first concentration, and the third amount of the respective compound is a third concentration of the respective compound other than the first concentration or the second concentration (B)

436 A subset of the wells in the plurality of wells in each multi-well plate in the plurality of multi-well plates comprise an aliquot of cells of the cell context that have not been exposed to the respective compound, and the measurement of the different feature in the plurality of features, across the plurality of instances of the cell context that has been exposed to the amount of the respective compound, is normalized by a mean of the different feature measured across the instances of the wells in the subset of wells that contain the cell context that have not been exposed to the respective compound.

438 The normalization of the different feature is normalized by the mean of the different feature measured across the instances of the wells in the subset of the wells that contain the cell context that have not been exposed to the compound by a method including:

a) subtracting (i) the mean of the different feature measured across the instances of the wells in the subset of wells that contain the cell context from that have not been exposed to the compound from (ii) each measurement of the different feature across the plurality of instances of the cell context upon exposure of the amount of the respective compound, and b) dividing the measurement of the different feature across the plurality of instances of the cell context upon exposure of the amount of the respective compound by a standard deviation of the different feature measured across the instances of the wells in the subset of wells that contain the cell context that have not been exposed to the compound.

440 The plurality of cell contexts consists of two or more cell types

442 The plurality of cell contexts consists of five or more cell types

444 A first cell context in the plurality of cell contexts consists of a first cell type and a second cell context in the plurality of cell contexts consist of the first cell type exposed to a perturbing agent

446 The perturbing agent is a toxin, a cytokine, a predetermined drug, a siRNA, a sgRNA, a different cell time, a cell type from a different donor, or a cell culture condition (C)

448 A first cell context in the plurality of cell contexts consists of a first native cell type and a second cell context in the plurality of cell contexts consist of the first native cell type that has incurred a genetic modification 450 The genetic modification is a genetic deletion or insertion 452 The exposure of the amount of the respective compound to the plurality of instances of the cell type is for at least one hour prior to obtaining the measurement 454 The corresponding set of elements consists of between 5 test elements and 100,000 elements 456 Each feature in the plurality of features is an optical feature that is optically measured 458 A first subset of the plurality of features are optical features that are optically measured, and a second subset of the plurality of features are non-optical features 460 Each feature in the plurality of features is a feature that is non-optically measured 462 Perform the obtaining (402) for each cell context in a plurality of cell contexts, thereby obtaining for each respective compound in the plurality of compounds, a plurality of vectors (D)

Fig. 4D

464 Reduce a dimension of each vector in the plurality of vectors using a dimension reduction technique

466 The dimension reduction technique is principal component analysis in which a plurality of principal components is identified based on a variance in the measurement of each different feature in the plurality of features, for a cell context in the plurality of cell contexts, across each compound in the plurality of compounds, and each respective vector in the plurality of concatenated vectors for the cell context is re-expressed as a projection of the respective concatenated vector onto the plurality of principal components

468 Each respective principal component analysis in the plurality of principal components is associated with a corresponding eigenvalue, and each respective principal component in the plurality of principal components is normalized by the square root of the corresponding eigenvalue prior to using the plurality of principal components to reexpress each respective vector in the plurality of vectors

470 A subset of the wells in the plurality of wells in each multi-well plate in the plurality of multi-well plates comprise an aliquot of cells of the cell context that have not been exposed to the respective compound, and each respective element in the respective vector is normalized by a measure of central tendency of the respective element in the vectors representing the subset of the wells that contain the cell context that have not been exposed to the respective compound prior to applying the dimension reduction technique

472 Each respective element in the respective vector is normalized by a measure of central tendency of the respective element in the vectors representing the subset of the wells that contain the cell context by a method comprising: a) subtracting the measure of central tendency of the respective element across the vectors representing the subset of the wells that contain the cell context that have not been exposed to the respective compound, and b) dividing by a measure of dispersion of the respective element in the vectors representing the subset of the wells that contain the cell context that have not been exposed to the respective compound

474 The dimension reduction method includes:

(i) application of a kernel function to the respective measurement of each measured different feature in the plurality of features, for a cell context in the plurality of cell contexts, across each compound in the plurality of compounds, thereby deriving a kernel matrix, and (ii) applying principal component analysis to the kernel matrix thereby identifying a plurality of principal components and wherein each respective vector in the plurality of combined vectors for the cell context is re-expressed as a projection of the respective combined vector onto the plurality of principal components

476 (A) for each respective compound in the plurality of compounds:

for each respective cell context in the plurality of cell contexts:

compute an angle between each vector representing the respective compound in the respective cell context thereby forming a distribution of angles for the respective compound for the respective cell context, and determine a distribution p-value for the distribution of angles for the respective compound for the respective cell context; and (B) eliminate any compound from the plurality of compounds that fails a p-value distribution threshold for each cell contexts in the plurality of cell contexts

402 The p-value distribution threshold is 0.05

478 Combine, for each respective compound in the plurality of compounds, the plurality of vectors for the respective compound to form a combined vector for the respective compound, thereby forming a plurality of combined vectors, each combined vector in the plurality of combined vectors representing a different compound in the plurality of compounds

Fig. 4F ( F )

480 Prune the plurality of compounds to the subset of compounds based on a similarity between respective combined vectors in the plurality of combined vectors corresponding to respective compounds in the plurality of compounds

482 Compute an angle between respective combined vector pairs in the plurality of combined vectors for all respective pairs of compounds in the plurality of compounds

484 The distance is an angular distance computed as:

$$\frac{\sum_{i}^{n} A_i B_i}{\sqrt{\sum_{i=1}^{n} A_i^2} \sqrt{\sum_{i=1}^{n} B_i^2}}$$

where: $A_i$ is an element $i$ in a first combined vector, in the plurality of combined vectors, that represents a first compound in a compound pair, $B_i$ is an element $i$ in a second combined vector, in the plurality of combined vectors, that represents a second compound in the compound pair, and $n$ is a number of elements common between the first combined vector and the second combined vector

486 identify a pair of compounds, consisting of a first compound and a second compound, from the computing (a) that has a smallest angle

488 discard a compound in the pair of compounds identified in the last instance of the identifying that has a smaller mean angle with respect to the combined vector of each other compound remaining in the plurality of compounds

490 repeat the identifying and the discarding until a threshold number of compounds have been pruned from the plurality of compounds or a number of compounds in the subset of compounds satisfies a threshold value

Fig. 4G

SYSTEMS AND METHODS FOR HIGH THROUGHPUT COMPOUND LIBRARY CREATION

REFERENCE TO RELATED APPLICATIONS

The present application claims priority to U.S. Non-provisional application Ser. No. 16/190,946, filed Nov. 14, 2018, which claims priority to U.S. Provisional Application Ser. No. 62/760,686, filed on Nov. 13, 2018, the disclosures of which are incorporated herein by reference in their entirety.

TECHNICAL FIELD

The present disclosure relates generally to systems and methods for high throughput compound library creation.

BACKGROUND

High throughput screening (HTS) is a process used in pharmaceutical drug discovery to test large compound libraries containing thousands to millions of compounds for various biological effects. HTS typically uses robotics, such as liquid handlers and automated imaging devices, to conduct tens of thousands to tens of millions of assays, e.g., biochemical, genetic, and/or phenotypical, on the large compound libraries in multi-well plates, e.g., 96-well, 384-well, 1536-well, or 3456-well plates. In this fashion, lead-compounds that provide a desired biochemical, genetic, or phenotypic effect can be quickly identified from the large compound libraries, for further testing and development towards the goal of discovering a new pharmaceutical agent for disease treatment. For a review of basic HTS methodologies see, for example, Wildey M J et al., "Chapter Five—High-Throughput Screening," Annual Reports in Medicinal Chemistry, Academic Press, 50:149-95 (2017), which is hereby incorporated by reference. However, HTS suffers from several inherent challenges.

First, although many commercial and proprietary chemical libraries having very large numbers of compounds exist, these libraries do not begin to scratch the surface of the available chemical space from which a compound useful for therapy of a particular disorder may be identified. For example, the Diversity Compound Library (Charles River) contains 689,000 sourced compounds, the EXPRESS-Pick Collection Stock (Chem Bridge) contains over 480,000 chemical compounds, the CORE Library Stock contains more than 690,000 (Chem Bridge) compounds, and pharmaceutical companies have their own proprietary compound libraries having over a million compounds (Macarron R, et al., "Impact of high-throughput screening in biomedical research," Nat Rev Drug Discov., 10(3):188-95 (2011), which is hereby incorporated by reference). However, the number of possible compounds is nearly limitless.

For example, the PubChem database (see, Wang, Y., et al., Nucleic Acids Res. 40:D400-D412 (2012)), a public repository for screening data, lists over 93 million compounds for which screening data has been generated. And these are only the records that researchers have decided to share publicly, as many companies choose to keep their proprietary compound libraries and screening data secret. Moreover, limitless other compounds have either never been isolated and/or tested for therapeutic properties. Thus, there is no practical fashion to screen the entirety of the compound space, or even particular sections of compound space, even when a priori information about possible chemical functions exist.

Second, screening millions of compounds is a time-intensive process, even with the heavy use of automation and robotics. For example, Macarron R, et al., supra, estimates that initial screening of one million chemical compounds takes one to three months. Third, screening millions of compounds can be very expensive, considering both the costs of the compounds being screened, many of which have to be chemically synthesized, and the reagents used for a particular assay.

Fourth, the reagents needed for informative screening assays, particularly in phenotypic drug discovery approaches, can limit the number of screening assays that can be performed. In phenotypic drug discovery, preliminary screening assays are commonly performed in vitro, using targeted cell lines, or in vivo, using whole organisms, such as zebrafish (see, for example, Delvecchio C. et al., "The zebrafish: a powerful platform for in vivo, HTS drug discovery," Assay Drug Dev Technol., 9(4):354-61 (2011)). For review see, for example, Moffat J G et al., "Opportunities and challenges in phenotypic drug discovery: an industry perspective," Nat Rev Drug Discov., 16(8):531-43 (2017), which is hereby incorporated by reference. For instance, in some cases, primary cells or stem cells are used in HTS. Because of the limited availability of homogeneous primary or stem cell populations, very large compound libraries cannot be completely screened against these reagents. See, for example, Eglen R, et al., "Primary cells and stem cells in drug discovery: emerging tools for high-throughput screening," Assay Drug Dev Technol., 9(2):108-24 (2011), which is hereby incorporated by reference.

Thus, the vast size of compound space presents many challenges for pharmaceutical and biopharmaceutical drug discovery using existing high throughput screening methodologies.

SUMMARY

Given the above background, what is needed in the art are systems and methods for identifying and constructing smaller, smart compound libraries that can be used for primary high throughput screening.

The present disclosure addresses, among others, a need in the art for systems and methods that facilitate intelligent pruning of large chemical compound libraries, while maintaining sufficient diversity in the effects caused by the chemical compounds within the pruned library. The reduced size of these "smart" pruned chemical compound libraries, in turn, significantly reduces the time and cost associated with screening chemical compounds, e.g., for new drug discovery, without compromising the amount of coverage a significantly larger chemical compound library provides. The reduced size of these smart libraries also allows for phenotypic high throughput screening using reagents that are limited, e.g., primary cells, 3D cultures, whole organisms, etc. In this fashion, the methods and systems described herein for identifying a subset of compounds in a plurality of compounds speeds-up pharmaceutical drug discovery.

For instance, as described herein, the creation of smart compound libraries allows for initial screening to occur across a wider range of phenotypic effects, with a lower probability that two compounds within the library will provide the same effects on the screened context, e.g., a cell or whole organism. This is advantageous because each individual assay can be expensive, time consuming, and consuming of a limited resource. Thus, by using a library of compounds that has been selected based on the diversity of effects between the compounds, there is a greater probability that each compound will provide a different possible avenue for generating a biological effect.

In one aspect, the disclosure provides methods, systems, and computable readable media for identifying a subset of compounds in a plurality of compounds. The identifying includes obtaining, for each respective compound in the plurality of compounds, a corresponding vector, thereby obtaining a corresponding plurality of vectors. The identifying also includes performing the obtaining for each cell context in the plurality of cell contexts, thereby obtaining for each respective compound in the plurality of compounds, a plurality of vectors. The identifying also includes combining the plurality of vectors for each respective compound in the plurality of compounds to form a combined vector, thereby forming a plurality of combined vectors, each combined vector in the plurality of combined vectors representing a different compound in the plurality of compounds. The identifying also includes pruning the plurality of compounds to the subset of compounds based on a similarity between respective combined vectors in the plurality of combined vectors corresponding to respective compounds in the plurality of compounds.

In one aspect, the disclosure provides methods, systems, and computable readable media for identifying a subset of compounds in a plurality of compounds. The identifying includes obtaining, for each respective compound in the plurality of compounds, a corresponding vector, thereby obtaining a corresponding plurality of vectors. In such embodiments, each respective vector in the corresponding plurality of vectors comprises a corresponding set of elements, and each respective element in the corresponding set of elements comprises a measurement of a different feature in a plurality of features, across a plurality of instances of a cell context in a plurality of cell contexts upon exposure of an amount of the respective compound to the plurality of instances of the cell context in the presence of one or more optical emitting entities using a plurality of multi-well plates comprising a plurality of wells. The identifying also includes performing the obtaining for each cell context in the plurality of cell contexts, thereby obtaining for each respective compound in the plurality of compounds, a plurality of vectors, each vector in the plurality of vectors for the plurality of features across a different cell context in the plurality of cell contexts. The identifying also includes combining the plurality of vectors for each respective compound in the plurality of compounds to form a combined vector, thereby forming a plurality of combined vectors, each combined vector in the plurality of combined vectors representing a different compound in the plurality of compounds. The identifying also includes pruning the plurality of compounds to the subset of compounds based on a similarity between respective combined vectors in the plurality of combined vectors corresponding to respective compounds in the plurality of compounds.

Use of the aspects described above, results in identification of a subset of compounds that has the same phenotypic informative content of the larger, starting plurality of compounds. Such a reduced dataset provides for more efficient use of computer resources and/or lab resources to evaluate the original plurality of compounds. In some embodiments, the fold reduction from the plurality of compounds to the subset of compounds is a two-fold or greater reduction, a three-fold or greater reduction, a four-fold or greater reduction, or a ten-fold greater reduction. As an example, in the case where the reduction is a ten-fold reduction and the original plurality of compounds consists of 1000 compounds, the subset of compounds is 100 compounds or less.

Yet, the disclosed systems and methods ensure that the subset of compounds effectively samples the same high dimensional phenotypic space as the plurality of compounds. Thus, subsequent evaluation, by in silico and/or in vivo methods, of the subset of compounds is sufficient to phenotypically sample the plurality of compounds (without actually testing all the compounds in the plurality of compounds). For example, the subset of compounds, rather than the plurality of compounds, can be used in a cell-based assay representative of a disease condition to determine whether any compounds in the plurality of compounds have efficacy with respect to the disease condition. As another example, the subset of compounds, rather than the plurality of compounds, can be used in in silico methods to determine whether any compounds in the plurality of compounds have efficacy with respect to the disease condition. Such in silico methods include, for example, docking studies in which each compound in the subset of compounds is docked into the active site of an atomic representation of an enzyme associated with a disease condition to determine the rank order of the binding affinity of the subset of compounds. Such rank ordering can be used to prioritize subsequent in vivo testing of the compounds in cell based assays, cell-free enzymatic assays, or animal-based assays designed to assess the efficacy of such compounds with respect to a disease condition. The reduction of the plurality of compounds down to the subset of compounds makes any such subsequent assays or in silico computations more efficient because the disclosed systems and methods ensure that the smaller number of compounds (the subset of compounds) covers the same phenotypic space as the larger original plurality of compounds.

In some embodiments, the measurement of the different feature in the plurality of features is a fluorescent microscopy measurement of the different feature. In some embodiments, the measurement of the different feature in the plurality of features is a bright field measurement of the different feature. In some embodiments, the measurement of the different feature in the plurality of features is phase contrast measurement of the different feature. In some embodiments, each feature in the plurality of features represents a color, texture, or size of the cell or an enumerated portion of the cell context upon exposure of the cell context to the amount of the respective compound.

In some embodiments, each respective instance of the plurality of instances of the cell context is imaged to form a corresponding two-dimensional pixelated image having a corresponding plurality of native pixel values and a feature in the plurality of features comprises a result of a convolution or a series convolutions and pooling operators run against native pixel values in the plurality of native pixel values of the corresponding two-dimensional pixelated image.

In some embodiments, the one or more optical emitting compounds are dyes and the vector for a compound in the plurality of compounds includes respective measurements of features in the plurality of features for the cell context in the presence of each of at least three different dyes.

In some embodiments, the one or more optical emitting compounds are dyes and the vector for a compound in the plurality of compounds includes respective measurements of features in the plurality of features for the cell context in the presence of each of at least five different dyes.

In some embodiments, a first amount of the respective compound is tested in a first subset of the plurality of instances of the cell context, and a second amount of the respective compound is tested in a second subset of the plurality of instances of the cell context.

In some embodiments, the first subset of the plurality of instances is three instances, and the second subset of the plurality of instances is three instances.

In some embodiments, the first amount is 0.3 µM, and the second amount is 1 µM.

In some embodiments, a third amount of the respective compound is tested in a third subset of the plurality of instances of the cell context.

In some embodiments, the third subset of the plurality of instances is three instances.

In some embodiments, the third amount is 3 µM.

In some embodiments, the first amount of the respective compound is a first concentration of the respective compound, the second amount of the respective compound is a second concentration of the respective compound other than the first concentration, and the third amount of the respective compound is a third concentration of the respective compound other than the first concentration or the second concentration.

In some embodiments, a subset of the wells in the plurality of wells in each multi-well plate in the plurality of multi-well plates comprise an aliquot of cells of the cell context that have not been exposed to the respective compound, and the measurement of the different feature in the plurality of features, across the plurality of instances of the cell context that has been exposed to the amount of the respective compound, is normalized by a mean of the different feature measured across the instances of the wells in the subset of wells that contain the cell context.

In some embodiments, the normalization of the different feature is normalized by the mean of the different feature measured across the instances of the wells in the subset of the wells that contain the cell context by a method including: subtracting (i) the mean of the different feature measured across the instances of the wells in the subset of wells that contain the cell context from (ii) each measurement of the different feature across the plurality of instances of the cell context upon exposure of the amount of the respective compound, and dividing the measurement of the different feature across the plurality of instances of the cell context upon exposure of the amount of the respective compound by a standard deviation of the different feature measured across the instances of the wells in the subset of wells that contain the cell context.

In some embodiments, the method further includes reducing a dimension of each vector in the plurality of vectors using a dimension reduction technique. In some embodiments, the dimension reduction technique is principal component analysis in which a plurality of principal components is identified based on a variance in the measurement of each different feature in the plurality of features, for a cell context in the plurality of cell contexts, across each compound in the plurality of compounds, and each respective vector in the plurality of concatenated vectors for the cell context is re-expressed as a projection of the respective concatenated vector onto the plurality of principal components.

In some embodiments, each respective principal component analysis in the plurality of principal components is associated with a corresponding eigenvalue, and each respective principal component in the plurality of principal components is normalized by the square root of the corresponding eigenvalue prior to using the plurality of principal components to reexpress each respective vector in the plurality of vectors.

In some embodiments, a subset of the wells in the plurality of wells in each multi-well plate in the plurality of multi-well plates comprise an aliquot of cells of the cell context that have not been exposed to the respective compound, and each respective element in the respective vector is normalized by a mean of the respective element in the vectors representing the subset of the wells that contain the cell context.

In some embodiments, each respective element in the respective vector is normalized by a mean of the respective element in the vectors representing the subset of the wells that contain the cell context by a method including: subtracting the mean of the respective element across the vectors representing the subset of the wells that contain the cell context, and dividing by a standard deviation of the respective element in the vectors representing the subset of the wells that contain the cell context.

In some embodiments, the method further includes: for each respective compound in the plurality of compounds: for each respective cell context in the plurality of cell contexts: computing an angle between each vector representing the respective compound in the respective cell context thereby forming a distribution of angles for the respective compound for the respective cell context, and determining a distribution p-value for the distribution of angles for the respective compound for the respective cell context (e.g., relative to a null hypothesis); and eliminating any compound from the plurality of compounds that fails a p-value distribution threshold for each cell contexts in the plurality of cell contexts. In some embodiments, the p-value distribution threshold is 0.05.

In some embodiments, the pruning the plurality of compounds to the subset of compounds based on the similarity between the combined vectors corresponding to the plurality of compounds is performed by a procedure that includes: computing an angle between respective combined vector pairs in the plurality of combine vectors for all respective pairs of compounds in the plurality of compounds, identifying a pair of compounds, consisting of a first compound and a second compound, from the computing (a) that has a smallest angle, discarding a compound in the pair of compounds identified in the last instance of the identifying (b) that has a smaller mean angle with respect to the combined vector of each other compound remaining in the plurality of compounds, and repeating the identifying (b) and the discarding (c) until a threshold number of compounds have been pruned from the plurality of compounds or a number of compounds in the subset of compounds satisfies a threshold value.

In some embodiments, the distance is an angular distance computed as:

$$\frac{\sum_{i}^{n} A_i B_i}{\sqrt{\sum_{i=1}^{n} A_i^2} \sqrt{\sum_{i=1}^{n} B_i^2}}$$

where, $A_i$ is an element i in a first combined vector, in the plurality of combined vectors, that represents a first compound in a compound pair, $B_i$ is an element i in a second combined vector, in the plurality of combined vectors, that represents a second compound in the compound pair, and n is a number of elements common between the first combined vector and the second combined vector.

In some embodiments, the plurality of cell contexts consists of two or more cell types. In some embodiments, the plurality of cell contexts consists of five or more cell types.

In some embodiments, a first cell context in the plurality of cell contexts consists of a first cell type and a second cell context in the plurality of cell contexts consist of the first cell type exposed to a perturbing agent.

In some embodiments, the perturbing agent is a toxin, a cytokine, a predetermined drug, a siRNA, a sgRNA, a different cell time, a cell type from a different donor, or a cell culture condition.

In some embodiments, a first cell context in the plurality of cell contexts consists of a first native cell type and a second cell context in the plurality of cell contexts consist of the first native cell type that has incurred a genetic modification.

In some embodiments, the genetic modification is a genetic deletion or insertion.

In some embodiments, the exposure of the amount of the respective compound to the plurality of instances of the cell type is for at least one hour prior to obtaining the measurement.

In some embodiments, the corresponding set of elements consists of between 5 test elements and 100,000 elements.

In some embodiments, each feature in the plurality of features is an optical feature that is optically measured.

In some embodiments, a first subset of the plurality of features are optical features that are optically measured, and a second subset of the plurality of features are non-optical features.

In some embodiments, each feature in the plurality of features is a feature that is non-optically measured.

In some embodiments, the dimension reduction method includes: application of a kernel function to the respective measurement of each measured different feature in the plurality of features, for a cell context in the plurality of cell contexts, across each compound in the plurality of compounds, thereby deriving a kernel matrix, and applying principal component analysis to the kernel matrix thereby identifying a plurality of principal components. In such embodiments, each respective vector in the plurality of combined vectors for the cell context is re-expressed as a projection of the respective combined vector onto the plurality of principal components.

BRIEF DESCRIPTION OF THE DRAWINGS

FIGS. 4A, 4B, 4C, 4D, 4E, 4F, and 4G collectively provide a flow chart of processes and features for identifying a subset of compounds in a plurality of compounds for use as an initial screening library of compounds, e.g., for drug discovery, in which optional steps are denoted by dashed boxes, in accordance with various embodiments of the present disclosure.

Like reference numerals refer to corresponding parts throughout the several views of the drawings.

DETAILED DESCRIPTION

Figure 1B:
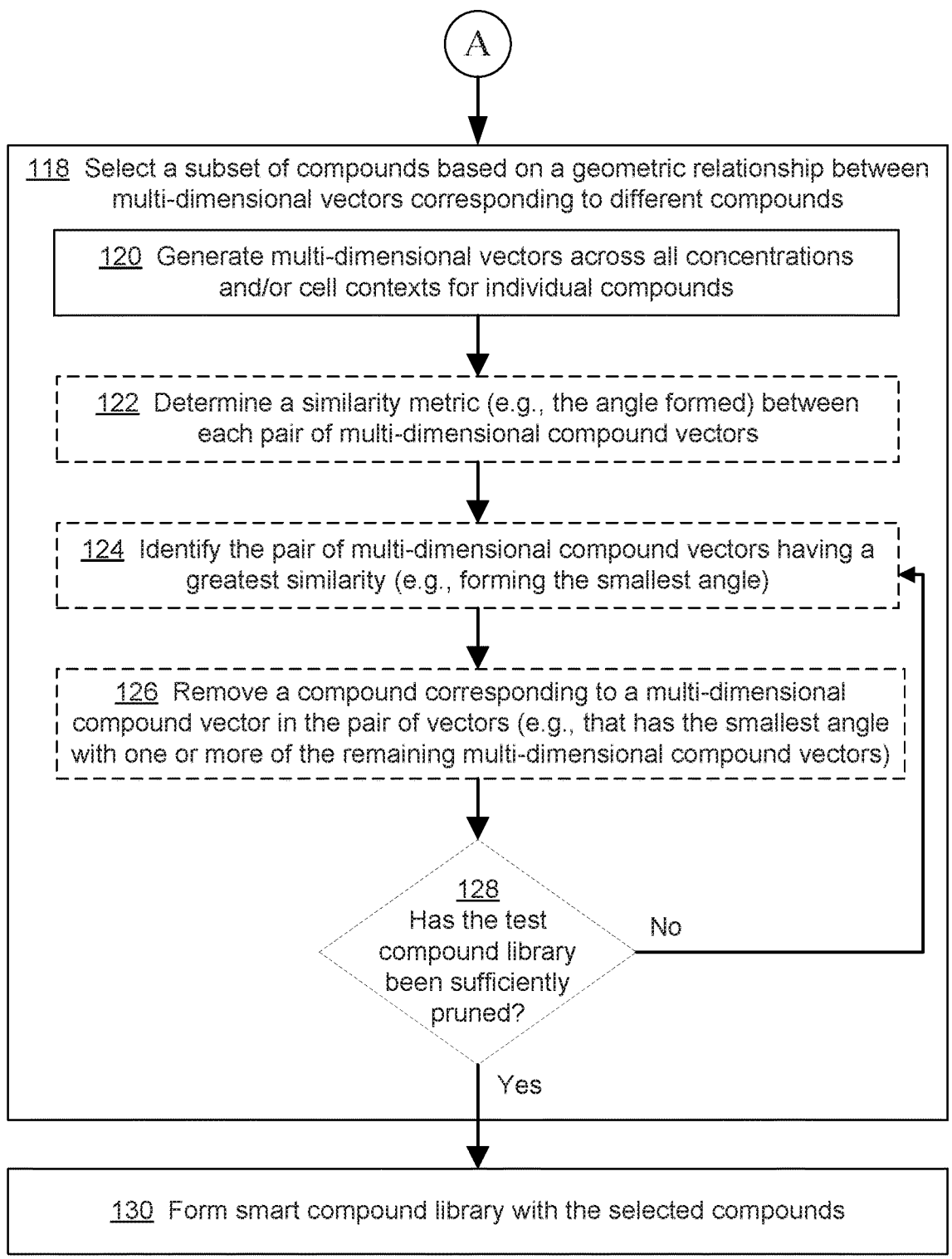
FIG. 1 illustrates an exemplary workflow for identifying a subset of compounds in a plurality of compounds for use as an initial screening library of compounds, e.g., for drug discovery, in accordance with various embodiments of the present disclosure.

Referring to FIG. 1, the present disclosure provides a screening method 100 for identifying a subset of compounds in a compound library that are representative of the larger set of compounds in the library. In some embodiments, the identification of a sub-plurality of compounds is based on measurements of a plurality of features of test instances in one or more cell contexts for each compound in the compound library, which are used to create multi-dimensional vectors for each compound, e.g., either or both multi-dimensional instance vectors incorporating measurements from a single series of test instances for each compound (e.g., separate multi-dimensional vectors for each instance of a cell context that is exposed to a respective compound) and multi-dimensional compound vectors incorporating measurements from multiple (e.g., all) series of test instances for each compound (e.g., a single multi-dimensional vectors for each respective compound that incorporates measurements from each instance of a cell context that is exposed to the respective compound). Geometric relationships between the multi-dimensional vectors are then used to identify a subset of compounds, e.g., that is representative of the diversity of effects provided by the whole compound library. In some embodiments, the compound library is pruned by comparing (108) multi-dimensional instance vectors, representing measurements of features caused by the same compound, e.g., across multiple replicates of the measurements, across multiple concentrations of the compound, and/or across multiple cell contexts. In some embodiments, the compound library is pruned by comparing (120) multi-dimensional compound vectors, representing measurements of features caused by different compounds.

In some embodiments, the method includes measuring (102) features of a plurality of test instances in one or more cell context exposed to each compound in a test compound library, e.g., in multiplex assays that expose each cell context to each test compound in the library of compounds, in one or more series of replicates and at one or more concentration of each compound. In some embodiments, each feature measurement is standardized (104) against a control instance, e.g., a measurement from a control instance performed in the same cell context as the measured instance, where the control instance does not include a test compound (e.g., a negative control instance), includes a reduced concentration of the test compound, or includes a compound other than the test compound.

In some embodiments, the method includes generating (106) multi-dimensional instance vectors for each compound in the compound library based on measurements (e.g., standardized measurements) of each test instance of a cell context exposed to a respective compound, thereby generating a plurality of multi-dimensional instance vectors for each compound. For instance, in some embodiments, a multi-dimensional vector is generated based on every measurement taken for an instance in which a respective compound was exposed to a respective cell context at a particular concentration of the compound, thereby generating a plurality of multi-dimensional instance vectors for each compound, where each multi-dimensional instance vector in the plurality of multi-dimensional instance vectors for a compound represents a different concentration of the compound and/or a different cell context to which the compound was exposed. In some embodiments, where each instance is performed in a series of replicates (e.g., where a respective compound is exposed to a respective cell context at a respective compound concentration in two or more instances), measurements from respective replicates of the instance are represented in separate multi-dimensional instance vector, e.g., generating a plurality of multi-dimensional instance vectors for each compound exposed to each cell context at each compound concentration. In some embodiments, where each instance is performed in a series of replicates (e.g., where a respective compound is exposed to a respective cell context at a respective compound concentration in two or more instances), all the measurements from all the replicates are represented in the multi-dimensional instance vector, e.g., as individual dimensions or averaged within a single dimension.

In some embodiments, method 100 includes selecting (108) a subset of compounds based on a geometric relationship between multi-dimensional instance vectors corresponding to the same compound, e.g., comparing multi-dimensional instance vectors generated for a single compound with each other, e.g., to eliminate compounds that do not provide internally consistent effects on one or more cell context. In some embodiments, the selecting includes reducing (118) dimensions of the multi-dimensional instance vectors (e.g., using a feature projection method such as linear or non-linear principle component analysis, non-negative matrix factorization, or linear or non-linear discriminant analysis). In some embodiments, the selecting includes whitening (112) the multi-dimensional instance vectors (e.g., dimension-reduced instance vectors) against control instances. In some embodiments, the selecting includes standardizing (114) the multi-dimensional instance vectors (e.g., dimension-reduced instance vectors and/or whitened instance vectors) against control instances. In some embodiments, the selecting includes filtering-out (116) compounds with disparate effects across different replicates, e.g., removing compounds associated with multi-dimensional instance vectors having more than a threshold amount of geometric difference, representing differing effects across different replicates. In some embodiments, a compound is filtered out only if it provides inconsistent effects (e.g., as identified by geometric differences between multi-dimensional instance vectors) across all cellular contexts. That is, if the compound provides consistent effects across at least one cellular context, the compound is not removed from the compound library. In some embodiments, a compound is filtered out if it provides inconsistent effects across a single cellular context. Likewise, the person of skill in the art can decide at what level of inconsistent results a compound should be removed from the compound library (e.g., when it provides inconsistent effects across two, three, four, or more cellular contexts, or when it provides inconsistent effects across at least 25%, 50%, 75%, or more of the cellular contexts).

In some embodiments, method 100 includes selecting (118) a subset of compounds based on a geometric relationship between multi-dimensional compound vectors corresponding to different compounds, e.g., comparing multi-dimensional compound vectors corresponding to all feature measurements for a respective compound across all concentrations and/or cell contexts, to each other. In some embodiments, the selecting is performed on the entire compound library for which measurements were obtained. In some embodiments, the selecting is performed on a reduced compound library, e.g., a compound library that was previously pruned by removing compounds with disparate effects across different replicates, concentrations, and/or cell contexts. In some embodiments, the selecting includes combining (120) multi-dimensional instance vectors across all concentrations and/or cell contexts for respective compounds, e.g., full-size or dimension-reduced instance vectors. In some embodiments, the selecting includes determining (122) a similarity metric between respective pairs of multi-dimensional compound vectors (e.g., an angle formed between respective pairs of multi-dimensional compound vectors). In some embodiments, the selecting includes identifying (124) a pair of multi-dimensional compound vectors that are most similar (e.g., that form the smallest angle of any pair of respective compound vectors remaining in the compound library), e.g., representing the two remaining compounds providing the most similar effects across all measured instances. In some embodiments, the selecting includes removing (126) one or the compounds in the identified pair, e.g., the compound in he identified pair that is most similar to one or more other compounds remaining in the compound library (e.g., the compound corresponding to the multi-dimensional compound vector in the pair of compound vectors that forms the smallest angle with one or more of the remaining multi-dimensional compound vectors, for example, the smallest average angle with every other remaining multi-dimensional compound vector). In some embodiments, the selecting includes iterating (128) the similarity identification (e.g., the angle pair identification) (124) and eliminating compounds (128) until the compound library has been sufficiently pruned, e.g., been reduced to a desired size or complexity.

Accordingly, the result of method 100 is that a smart compound library is formed (130) by the selected compounds, e.g., those compounds that weren't eliminated after making intra-compound comparisons of associated multi-dimensional instance vectors and/or inter-compound comparisons of associated multi-dimensional compound vectors, thereby providing a smaller compound library that is representative of the larger, original compound library.

Reference will now be made in detail to embodiments, examples of which are illustrated in the accompanying drawings. In the following detailed description, numerous specific details are set forth in order to provide a thorough understanding of the present disclosure. However, it will be apparent to one of ordinary skill in the art that the present disclosure may be practiced without these specific details. In other instances, well-known methods, procedures, components, circuits, and networks have not been described in detail so as not to unnecessarily obscure aspects of the embodiments.

Definitions

It will also be understood that, although the terms first, second, etc. may be used herein to describe various elements, these elements should not be limited by these terms. These terms are only used to distinguish one element from another. For example, a first subject could be termed a second subject, and, similarly, a second subject could be termed a first subject, without departing from the scope of the present disclosure. The first subject and the second subject are both subjects, but they are not the same subject. Furthermore, the terms "subject," "user," and "patient" are used interchangeably herein. By the term insulin pen is meant an injection device suitable for applying discrete doses of insulin, where the injection device is adapted for logging and communicating dose related data.

The terminology used in the present disclosure is for the purpose of describing particular embodiments only and is not intended to be limiting of the invention. As used in the description of the invention and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context.

As used herein, the term "control instance" or simply "control" refers to an experimental condition that lacks or significantly lacks a compound whose effects are being tested. In the context of the present disclosure, a control instance is a sample of a cell context that is not exposed to a respective compound from the compound library being tested, e.g., but is otherwise substantially identical to the test instance. In this fashion, control instances are used to minimize the effects that variables other than the compound being exposed to the cell context have on measured features. In some embodiments, a control instance is used for a plurality of test instances, e.g., where a respective cell context is not exposed to any compound, the control instance can be used as a control for any test instance in which the respective cell context is exposed to any compound. In other embodiments, a control instance is specific for one or a subset of test instances, e.g., where a respective cell context is exposed to a lower concentration of a respective test compound that in a test instance, the control instance can be used for only those test instances in which the respective cell context is exposed to the respective test compound (e.g., at higher concentrations). In some embodiments, a control instance includes a compound that is different from a respective test compound, e.g., a compound known to have or not to have a desired effect.

As used herein, the term "multi-dimensional instance vector" or simply "instance vector" refers to an n-dimensional vector of elements, where the elements include measured features from a test instance in which a respective cell context is exposed to a respective compound at a respective concentration. Accordingly, for a compound screening method in which a respective cell context is exposed to a respective compound at a respective concentration in multiple instances (e.g., replicates), a plurality of instance vectors are generated, each corresponding to different instances (e.g., replicates) in which a respective cell context is exposed to a respective compound at a respective concentration. In addition to measured features, instance vectors can also include elements derived externally from a screening assay, e.g., mechanism of action tags, chemical structures, functional groups, molecular weight, known activities, etc.

As used herein, the term "multi-dimensional compound vector" or simply "compound vector" refers to an n-dimensional vector of elements, where the elements include measured features from all test instances in which a cell context is exposed to a test compound. Accordingly, for a compound screening method in which multiple cell contexts are exposed to the same compound, a single compound vector is generated for a respective compound, incorporating measured features from all instances that included the respective compound. In some embodiments, a compound vector is formed by combining a plurality of instance vectors, e.g., which may or may not be normalized against one or more control instance, dimension reduced, or whitened, corresponding to the compound. In some embodiments, a compound vector is formed from component feature measurements, e.g., which may or may not be normalized against one or more control instance.

Systems for Smart Library Construction

Figure 2:
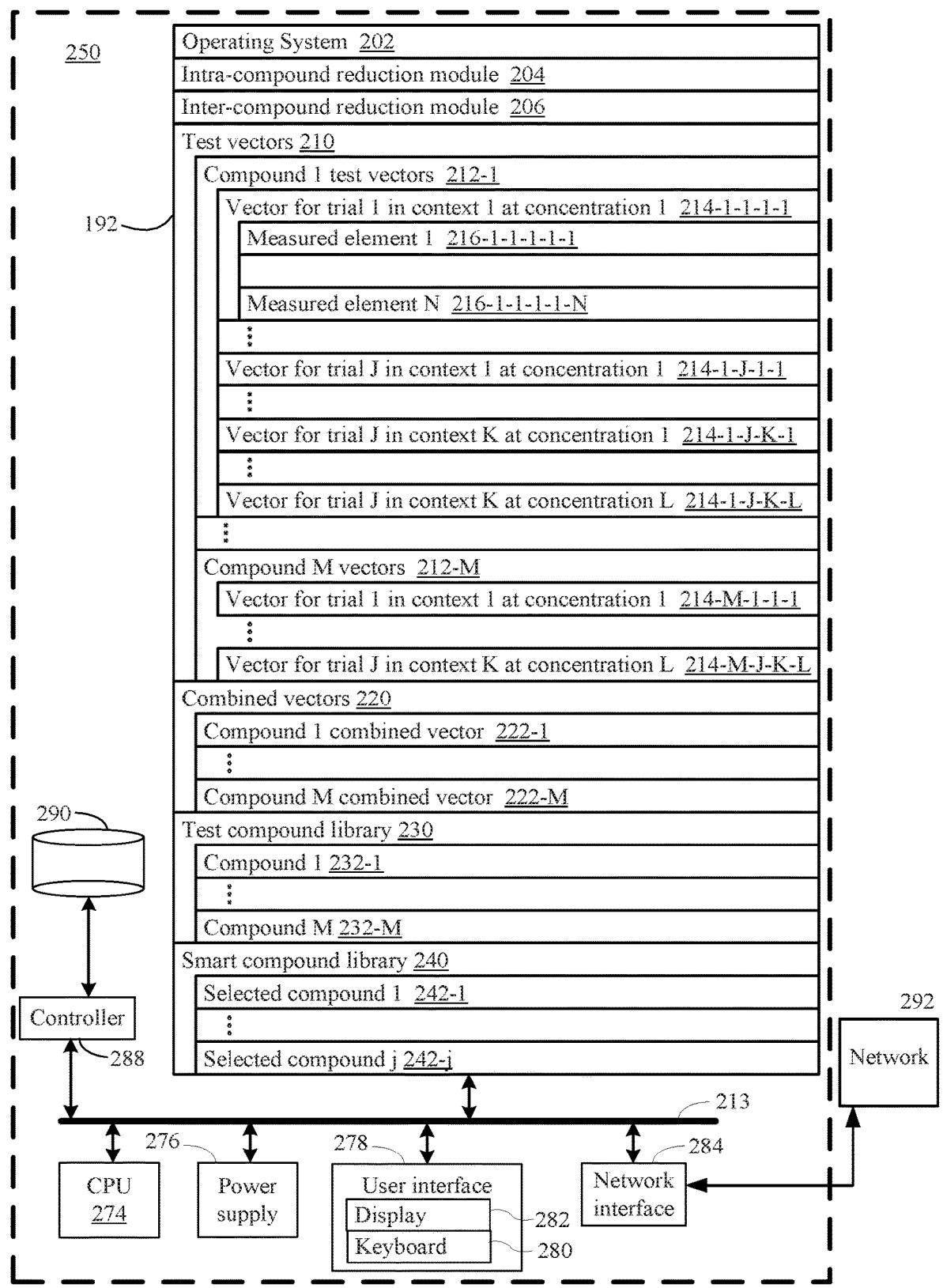
FIG. 2 illustrates a device for identifying a subset of compounds in a plurality of compounds for use as an initial screening library of compounds, e.g., for drug discovery, in accordance with various embodiments of the present disclosure.
Figure 3:
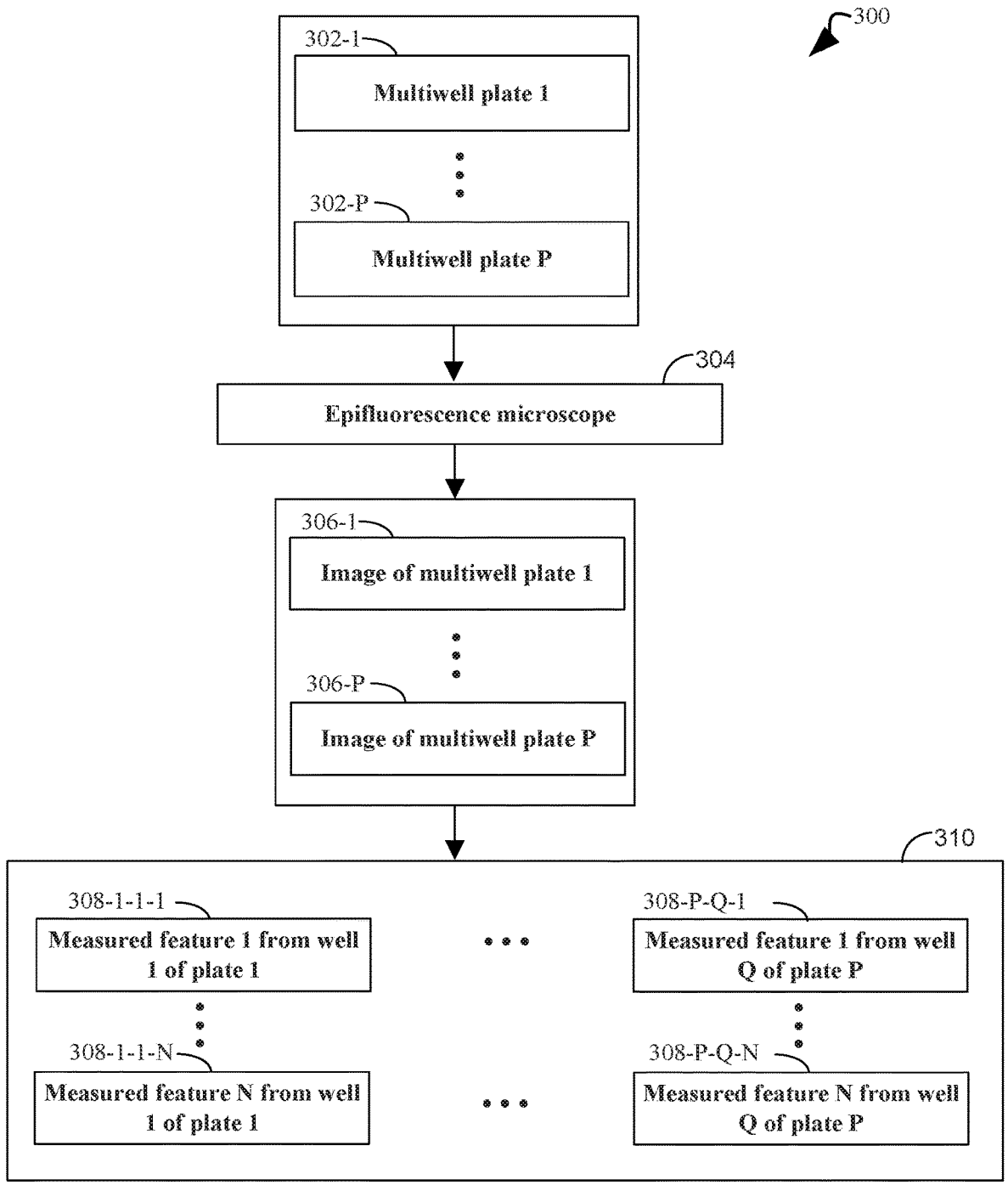
FIG. 3 illustrates an example workflow for acquiring measurements of different features, across a plurality of instances of a cell context in a plurality of cell contexts upon exposure of an amount of a respective compound to the plurality of instances of the cell context, in accordance with various embodiments of the present disclosure.

A detailed description of a system 250 for identifying a subset of compounds in a plurality of compounds is described in conjunction with FIGS. 2 and 3. As such, FIGS. 2 and 3 collectively illustrate the topology of the system, in accordance with an embodiment of the present disclosure. In the topology, there is a workflow for removing compounds, thereby selecting the remaining compounds, from a test compound library based on at least intra-compound and inter-compound geometric relationships between various multi-dimensional vectors formed from a plurality of feature measurements obtained across one or more instances of one or more concentrations of the compounds exposed to one or more cell contexts. Generation of the various multi-dimensional vectors, comparison of the geometric properties of the multi-dimensional vectors, and selection of a subset of compounds based on the geometric relationships is performed as described in further detail below by system 250 of FIG. 2.

Referring to FIG. 2, in typical embodiments, system 250 comprises one or more computers. For purposes of illustration in FIG. 2, system 250 is represented as a single computer that includes all of the functionality for identifying a subset of compounds in a plurality of compounds. However, the disclosure is not so limited. In some embodiments, the functionality for identifying a subset of compounds in a plurality of compounds is spread across any number of networked computers and/or resides on each of several networked computers and/or is hosted on one or more virtual machines at a remote location accessible across the communications network 106. One of skill in the art will appreciate that any of a wide array of different computer topologies are used for the application and all such topologies are within the scope of the present disclosure.

With the foregoing in mind, an example system 250 for identifying a subset of compounds in a plurality of compounds comprises one or more processing units (CPU's) 274, a network or other communications interface 284, a memory 192 (e.g., random access memory), one or more magnetic disk storage and/or persistent devices 290 optionally accessed by one or more controllers 288, one or more communication busses 213 for interconnecting the aforementioned components, a user interface 278, the user interface 278 including a display 282 and input 280 (e.g., keyboard, keypad, touch screen), and a power supply 276 for powering the aforementioned components. In some embodiments, data in memory 192 is seamlessly shared with non-volatile memory 290 using known computing techniques such as caching. In some embodiments, memory 192 and/or memory 290 includes mass storage that is remotely located with respect to the central processing unit(s) 274. In other words, some data stored in memory 192 and/or memory 290 may in fact be hosted on computers that are external to the system 250 but that can be electronically accessed by the system 250 over an Internet, intranet, or other form of network or electronic cable (illustrated as element 292 in FIG. 2) using network interface 284.

In some embodiments, the memory 192 of the system 250 for identifying a subset of compounds in a plurality of compounds stores:

- an operating system 202 that includes procedures for handling various basic system services;
- an intra-compound reduction module 204, e.g., for selecting (108) a subset of compounds based on a geometric relationship between multi-dimensional instance vectors 214 corresponding to the same compound;
- an inter-compound reduction module 206, e.g., for selecting (118) a subset of compounds based on a geometric relationship between multi-dimensional compound vectors 222 corresponding to different compounds;
- a test vector database 210 storing sets of multi-dimensional instance vectors 212 for each compound in the test compound library, each respective instance vector 214 in a respective set of instance vectors 212 for a respective compound including a plurality of measured elements 216 for a respective trial (e.g., repetition) in a respective cell context at a respective concentration of the respective compound;
- a combined vector database 220 storing multi-dimensional compound vectors 222 for compounds in the test compound library (e.g., all test compounds in the test compound library or all test compounds selected from intra-compound library reduction), each respective compound vector 222 including a plurality of measured elements 216 across a plurality of trials in a plurality of cell contexts at a plurality of concentrations of the respective compound;
- a test compound library record 230 including entries corresponding to each compound 232 in the test compound library; and
- a smart compound library record 240 including entries corresponding to each selected compound 242.

In some embodiments, the intra-compound reduction module 204 and/or inter-compound reduction module 206 is accessible within any browser (phone, tablet, laptop/desktop). In some embodiments the intra-compound reduction module 204 and/or inter-compound reduction module 206 runs on native device frameworks, and is available for download onto the system 250 running an operating system 202 such as Android or iOS.

In some implementations, one or more of the above identified data elements or modules of the system 250 for identifying a subset of compounds in a plurality of compounds are stored in one or more of the previously described memory devices, and correspond to a set of instructions for performing a function described above. The above-identified data, modules or programs (e.g., sets of instructions) need not be implemented as separate software programs, procedures or modules, and thus various subsets of these modules may be combined or otherwise re-arranged in various implementations. In some implementations, the memory 192 and/or 290 optionally stores a subset of the modules and data structures identified above. Furthermore, in some embodiments the memory 192 and/or 290 stores additional modules and data structures not described above.

In some embodiments, device 250 for identifying a subset of compounds in a plurality of compounds is a smart phone (e.g., an iPHONE), laptop, tablet computer, desktop computer, or other form of electronic device. In some embodiments, the device 250 is not mobile. In some embodiments, the device 250 is mobile.

Referring to FIG. 3, in some embodiments, the present disclosure relies upon the acquisition of a data set 310 that includes measurements of a plurality of features 308 (e.g., measured elements 216) from each compound in a test compound library, in one or more replicates in one or more cell contexts at one or more concentrations. As an example, each compound i in a compound library having M compounds is introduced into wells of a multiwell plate 302 at each of k concentrations for each of l cell contexts in j replicates, resulting in X wells containing compound i, where $X=(j)*(k)*(l)$. N features are then measured from each well $\{1 \ldots Q\}$ of each multiwell plate $\{1 \ldots P\}$, resulting in $N*M*X*$ measurements for the test compound library, as well as C control measurements, where $C=(j)*(l)$, e.g., j replicates of no compound measured across/cell contexts.

In some embodiments, referring to FIG. 3, this is accomplished by capturing images 306 of the multiwell plates using, for example, epifluorescence microscopy. The images 306 are then used as a basis for obtaining the measurements of the N different features from each of the wells in the multiwell plates, thereby forming dataset 310. Data set 310 is then used to generate multi-dimensional vectors for each compound, e.g., via intra-compound reduction module 204 and/or inter-compound reduction module 206 illustrated in FIG. 2.

Now that details of a system 250 for identifying a subset of compounds in a plurality of compounds have been disclosed, details regarding a flow chart of processes and features of the system, in accordance with an embodiment of the present disclosure, are disclosed with reference to FIGS. 4A through 4G. In some embodiments, such processes and features of the system are carried out by intra-compound reduction module 204 and/or inter-compound reduction module 206 illustrated in FIG. 2.

Referring to method 400, the systems described herein (e.g., system 250) include instructions for performing a method (e.g., methods 100 and/or 400) for identifying a subset of compounds in a plurality of compounds, e.g., identifying representative chemical compounds in a chemical compound library used for pharmaceutical drug discovery. The method includes obtaining (402), for each respective compound in the plurality of compounds, a corresponding vector (e.g., multi-dimensional instance vectors 214 as illustrated in FIG. 2), thereby obtaining a corresponding plurality of vectors (e.g., set of instance vectors 210 as illustrated in FIG. 2). In some embodiments, the obtaining includes obtaining underlying data (e.g., feature measurements) for the vectors and constructing the vectors, e.g., by combining data received for individual compounds. In some embodiments, feature measurements are collected directly by the system (e.g., system 250), e.g., the system includes instructions for processing images acquired of microwell plates. In some embodiments, the vectors and/or underlying data for the vectors is obtained from a remote source, e.g., over network 292 via network interface 284.

In some embodiments, each respective vector in the corresponding plurality of vectors includes (404) a corresponding set of elements (e.g., elements 216 as illustrated in FIG. 2), e.g., feature measurements corresponding to an effect the compound had on a particular cell context. In some embodiments, the instance vectors include, or are accompanied by, additional information about the compound, e.g., information that was not measured in an assay. For example, in some embodiments, this additional information includes annotated tags about the compound, e.g., MOA annotations for the compound. For instance, the vector may include, or be accompanied by, a known mechanism of action, a chemical structure or other structural characteristic of the molecule (e.g., an identity of a functional group within the compound). Available information about a chemical compound that can be incorporated into, or accompany, a multi-dimensional vector can be found, for example, in publicly available electronic databases, such as ChEMBL (see, Gaulton, A., et al., Nucleic Acids Res. 40:D1100-D1107 (2012)), PubChem (see, Wang, Y., et al., Nucleic Acids Res. 40:D400-D412 (2012)), and ZINC 15 (see, Sterling and Irwin, J. Chem. Inf. Model, 55:2324-37 (2015)). In some embodiments, the vector includes a two-dimensional fingerprint of the corresponding compound (e.g., an extended-connectivity fingerprint "ECFP" which are described in Rogers and Hahn, "Extended-connectivity fingerprints," 2010, Journal of Chemical Information and Modeling 50, no. 5, pp. 742-754, and on the Internet at docs.chemaxon.com/display/docs/Extended+Connectivity+Fingerprint+ECFP, accessed Sep. 14, 2018, each which is hereby incorporated by reference in its entirety) or a chemical hashed fingerprint of the corresponding compound (e.g., as described on the Internet at https://docs.chemaxon.com/display/docs/Chemical+Hashed+Fingerprint, accessed Sep. 14, 2018, is hereby incorporated by reference in its entirety).

Each respective element (e.g., elements 216) in the corresponding set of elements includes (406) a measurement of a different feature in a plurality of features, across a plurality of instances (e.g., two or more, three or more, four or more, five or more, six or more, seven or more, etc.) of a cell context in a plurality of cell contexts (e.g., 10 or more, 20 or more, 30 or more, 40 or more, 50 or more, 60 or more, 100 or more, 200 or more, etc.) upon exposure of an amount of the respective compound to the plurality of instances of the cell context. For example, as described with respect to FIG. 3, in some embodiments, each feature measurement is obtained in replicate, e.g., each condition (e.g., exposure of each cell context to each compound) is performed more than once (e.g., each compound is exposed to each cell context in a plurality of instances such as two or more instances, three or more instance, four or more instances, five or more instance, six or more instance, seven or more instance, etc.) and each feature measurement is obtained from each instance of the condition.

In some embodiments, the respective compound is exposed to the cell context in the presence of one or more optical emitting entities (417), e.g., using a plurality of multi-well plates comprising a plurality of wells. In some embodiments, the optical emitting entity can be a dye, a quantum dot, a fluorophore, etc.

Cell Contexts

In some embodiments, a cell context is one or more cells that have been deposited within a well of a multiwell plate 302, such as a particular cell line, primary cells, or a co-culture system. In some embodiments, as described herein with reference to FIG. 3, at least each compound (e.g., compounds 232) in the compound library (e.g., test compound library 230) that is not pre-selected to be included in the final smart library (e.g., in some embodiments, all compounds in the compound library are tested, regardless of whether they are pre-selected for the final smart library) is exposed to a plurality of different cell contexts, e.g., at least two, three, four, five, six, seven, eight, nine, ten, or more cell contexts. In some embodiments, at least each compound in the compound library that is not preselected to be included in the final smart library is exposed to a single cell context (e.g., a single cell line or primary cell type). In some embodiments, compounds that are pre-selected for inclusion in the final smart library are exposed to the cell contexts and included in the subsequent feature analysis, e.g., in order to identify and/or remove compounds providing similar phenotypes.

Examples of cell types that are useful to be included in a cell context include, but are not limited to, U2OS cells, A549 cells, MCF-7 cells, 3T3 cells, HTB-9 cells, HeLa cells, HepG2 cells, HEKTE cells, SH-SY5Y cells, HUVEC cells, HMVEC cells, primary human fibroblasts, and primary human hepatocyte/3T3-J2 fibroblast co-cultures. In some embodiments a cell line used as a basis for a cell context is a culture of human cells. In some embodiments, a cell line used as a basis for a cell context is any cell line set forth in Table 1 below, or a genetic modification of such a cell line. In some embodiments each cell line used as a different cell context in the screening method is from the same species. In some embodiments the cell lines used for a cell context in the screening method can be from more than one species. For instance, a first cell line used as a first context is from a first species (e.g., human) and a second cell line used as a second context is from a second species (e.g., monkey).

TABLE 1

Example cell types used as a basis for providing cell context in some embodiments.

| Cell Name | Tissue Type | Tissue | Phenotype | Primary |
|---|---|---|---|---|
| jb6 p+ c141 | Mouse | Skin | Adherent | no |
| jcam1.6 | Human | Lymphocyte | Suspension | no |
| jb6 rt101 | Mouse | Epithelial | Either | yes |
| jy | Human | Lymphocyte | Suspension | no |
| k562 | Human | Bone | Suspension | no |
| j82 | Human | Bladder | Adherent | no |
| ivec cells | Human | Endothelial | Adherent | no |
| jeg-3 | Human | Other | Adherent | no |
| jurkat | Human | Lymphocyte | Suspension | no |
| j558l | Mouse | Blood | Suspension | no |

TABLE 1-continued

Example cell types used as a basis for providing cell context in some embodiments.

| Cell Name | Tissue Type | Tissue | Phenotype | Primary |
|---|---|---|---|---|
| k46 | Mouse | Lymphocyte | Suspension | no |
| j774 cells | Mouse | Macrophage | Adherent | no |
| knrk | Rat | Epithelial | Either | no |
| keratinocytes | Mouse | Keratinocyte | Adherent | yes |
| kc1 | *Drosophila Melanogaster* | Default | Adherent | no |
| kc18-2-40 cells | Human | Keratinocyte | Adherent | no |
| kt-3 | Human | Lymphocyte | Suspension | no |
| kmst-6 | Human | Skin | Adherent | no |
| l1210-fas | Mouse | Myoblast | Suspension | yes |
| kb | Human | Fibroblast | Adherent | no |
| keratinocytes | Human | Keratinocyte | Adherent | yes |
| kg-1 cells | Human | Bone marrow | Suspension | no |
| ks cells | Human | Skin | Adherent | yes |
| kd83 | Mouse | Blood | Suspension | no |
| l-m(tk-) | Mouse | Connective | Adherent | no |
| l8 cells | Rat | Myoblast | Adherent | yes |
| lk35.2 | Mouse | Lymphocyte | Suspension | no |
| l1210 | Mouse | Monocyte | Suspension | yes |
| lan-5 | Human | Brain | Adherent | no |
| llc-pk1 | Pig | Kidney | Adherent | no |
| lewis lung carcinoma, llc | Mouse | Lung | Either | no |
| l6e9 | Rat | Muscle | Adherent | no |
| lmh | Chicken | Liver | Adherent | no |
| l6 cells | Rat | Muscle | Adherent | no |
| lisn c4 (nih 3t3 derivative overexpressing egf) | Mouse | Fibroblast | Adherent | yes |
| lap1 | Mouse | Lymphocyte | Suspension | yes |
| lap3 | Mouse | Embryo | Adherent | no |
| l929 | Mouse | Fibroblast | Adherent | no |
| mg87 | Mouse | Fibroblast | Adherent | no |
| min6 | Mouse | Default | Either | no |
| mel | Mouse | Other | Adherent | no |
| melenoma cells | Human | Melanoma | Adherent | yes |
| mdbk | Cow | Kidney | Adherent | no |
| mkn45 gastric cancer | Human | Stomach | Adherent | yes |
| mewo | Human | Melanoma | Adherent | no |
| mda-mb-468 | Human | Breast/Mammary | Adherent | no |
| mdck | Dog | Kidney | Adherent | no |
| mf4/4 | Mouse | Macrophage | Adherent | no |
| me-180 | Human | Cervix | Adherent | yes |
| mes-sa | Human | Uterus | Adherent | no |
| mg-63 cells | Human | Bone | Adherent | no |
| mono-mac-6 cells | Human | Blood | Suspension | no |
| monocytes | Human | Blood | Suspension | yes |
| mrc-5 | Human | Lung | Adherent | yes |
| mob cells | Mouse | Osteoblast | Adherent | yes |
| msc human mesenchymal stem cell | Human | Bone marrow | Adherent | yes |
| mt-2 | Human | Lymphocyte | Adherent | yes |
| mouse embryonic fibroblasts | Mouse | Fibroblast | Adherent | yes |
| mnt1 | Human | Skin | Adherent | yes |
| ms1 | Mouse | Pancreas | Adherent | no |
| mr1 | Rat | Embryo | Adherent | no |
| mt4 | Human | Lymphocyte | Suspension | yes |
| molt4 (human acute t lymphoblastic leukaemia) | Human | Blood | Suspension | no |
| hep3b | Human | Liver | Adherent | no |
| hepatic stellate cells | Rat | Liver | Adherent | yes |
| hela 229 cells | Human | Cervix | Either | yes |
| hep2 | Human | Epithelial | Adherent | no |
| hela-cd4 | Human | Epithelial | Adherent | no |
| hct116 | Human | Colon | Adherent | no |
| hepatocytes | Mouse | Liver | Adherent | yes |
| hela s3 | Human | Cervix | Adherent | no |
| hel | Human | Lymphocyte | Suspension | yes |
| hela cells | Human | Cervix | Adherent | no |
| hela t4 | Human | Blood | Suspension | no |
| hepg2 | Human | Liver | Adherent | no |
| high 5 (bti-tn-5b1-4) | Insect | Embryo | Adherent | no |
| hit-t15 cells | Hamster | Epithelial | Adherent | no |

TABLE 1-continued

Example cell types used as a basis for providing cell context in some embodiments.

| Cell Name | Tissue Type | Tissue | Phenotype | Primary |
|---|---|---|---|---|
| hepatocytes | Rat | Liver | Adherent | yes |
| hitb5 | Human | Muscle | Adherent | yes |
| hi299 | Human | Lung | Adherent | no |
| hfff2 | Human | Foreskin | Adherent | no |
| hib5 | Rat | Brain | Adherent | yes |
| hm-1 embryonic stem cells | Mouse | Other | Adherent | yes |
| hitb5 | Human | Muscle | Adherent | yes |
| hl-60 | Human | Lymphocyte | Suspension | no |
| hl-5 | Mouse | Heart | Adherent | no |
| hl-1 | Mouse | Heart | Adherent | no |
| glya | Hamster | Ovary | Adherent | no |
| gamma 3t3 | Mouse | Fibroblast | Adherent | no |
| gh3 | Rat | Pituitary | Adherent | no |
| granta-519 | Human | Blood | Suspension | no |
| freestyle 293 | Human | Kidney | Suspension | no |
| g401 | Human | Connective | Adherent | no |
| fto-2b (rat hepatoma) cells | Rat | Liver | Suspension | yes |
| gh4c1 | Rat | Pituitary | Adherent | yes |
| fsdc, murine dendritic cell | Mouse | Blood | Either | no |
| goto | Human | Neuroblastoma | Adherent | yes |
| gc-2spd (ts) | Mouse | Epithelial | Adherent | no |
| glomeruli | Rat | Lung | Adherent | yes |
| frt | Rat | Thyroid | Suspension | no |
| h19-7/igf-ir | Rat | Brain | Suspension | no |
| gt1 | Mouse | Brain | Adherent | no |
| griptite? 293 msr | Human | Kidney | Adherent | no |
| h441 | Human | Lung | Adherent | yes |
| h-500, leydig tumor cell | Rat | Testes | Adherent | yes |
| h4 | Human | Glial | Adherent | no |
| guinea pig endometrial stromal cells | Guinea Pig | Ovary | Adherent | yes |
| h187 | Human | Lung | Adherent | yes |
| h35 | Rat | Liver | Adherent | no |
| h-7 | Mouse | Bone marrow | Suspension | no |
| h1299 | Human | Lung | Adherent | no |
| granulosa cells | Mouse | Ovary | Either | yes |
| hbl100 cells | Human | Breast/Mammary | Adherent | no |
| h9c2 | Rat | Myoblast | Adherent | no |
| hbec-90 | Human | Brain | Adherent | no |
| has-p | Mouse | Breast/Mammary | Adherent | yes |
| hasmcs | Human | Muscle | Adherent | no |
| hc11 | Mouse | Breast/Mammary | Adherent | no |
| hacat | Human | Keratinocyte | Adherent | yes |
| hb60-5 cells | Mouse | Spleen | Adherent | no |
| h4iie | Rat | Liver | Adherent | yes |
| hca-7 | Human | Colon | Adherent | yes |
| hcd57 | Mouse | Blood | Suspension | no |
| haecs | Human | Aorta | Adherent | yes |
| rpe.40 | Hamster | Kidney | Adherent | yes |
| rcme, rabbit coronary microvessel endothelial | Rabbit | Endothelial | Adherent | yes |
| rko, rectal carcinoma cell line | Human | Colon | Adherent | no |
| ros, rat osteoblastic cell line | Rat | Osteoblast | Adherent | yes |
| rh18 | Human | Muscle | Adherent | no |
| rcho | Rat | Default | Adherent | no |
| rccd1 | Rat | Kidney | Adherent | no |
| s194 cells | Mouse | Lymphocyte | Adherent | yes |
| rin 1046-38 | Rat | Pancreas | Suspension | no |
| rw-4 | Mouse | Embryo | Adherent | yes |
| rj2.2.5 | Human | Lymphocyte | Suspension | no |
| rk13 | Rabbit | Kidney | Adherent | no |
| remc | Rat | Breast/Mammary | Adherent | no |
| sk-br-3 | Human | Breast/Mammary | Adherent | no |
| s49.1 | Mouse | Thymus | Suspension | no |
| schizosaccharomyces pombe | Yeast | Other | Either | yes |
| sf9 | Insect | Ovary | Suspension | no |
| sf21 | Insect | Other | Either | yes |
| sf21ae | Insect | Other | Either | yes |
| sh-sy5y | Human | Brain | Either | no |

TABLE 1-continued

Example cell types used as a basis for providing cell context in some embodiments.

| Cell Name | Tissue Type | Tissue | Phenotype | Primary |
|---|---|---|---|---|
| s2-013 | Human | Pancreas | Either | yes |
| saos-2 | Human | Bone | Adherent | no |
| siha | Human | Cervix | Adherent | no |
| scc12, human squamous cell carcinoma line (c12c20) | Human | Skin | Adherent | yes |
| shep | Human | Brain | Adherent | no |
| sk-lms-1 | Human | Other | Adherent | no |
| sk-n-sh, neuronal cells | Human | Brain | Adherent | yes |
| sk-n-as | Human | Neuroblastoma | Adherent | no |
| sknmc | Human | Brain | Adherent | no |
| sk-hep-1 cells | Human | Skin | Either | yes |
| skov3 | Human | Ovary | Adherent | no |
| sk-n-be(2) | Human | Neuroblastoma | Adherent | yes |
| smmc7721 | Human | Liver | Adherent | no |
| smooth muscle cells (aortic) rasmc (a7-r5) | Rat | Aorta | Adherent | yes |
| sl2 | *Drosophila melanogaster* | Default | Either | no |
| sk-ut-1 | Human | Muscle | Adherent | no |
| n2a | Mouse | Neuroblastoma | Adherent | no |
| myocytes (ventricular) | Rat | Heart | Adherent | yes |
| mtln3 | Rat | Breast/Mammary | Adherent | no |
| n1e-115 | Mouse | Brain | Adherent | no |
| mtsv1-7 | Human | Epithelial | Adherent | no |
| murine alveolar macrophages cell line mhs | Rat | Lung | Adherent | no |
| n18tg cells | Mouse | Neuroblastoma | Adherent | no |
| n13 | Mouse | Brain | Adherent | no |
| mutu group3, b-cell line | Human | Lymphocyte | Suspension | no |
| mtd-1a | Mouse | Epithelial | Adherent | yes |
| mutu i | Human | Lymphocyte | Suspension | no |
| mv1lu | Mink | Lung | Adherent | no |
| ncb20 | Mouse | Neuroblastoma | Adherent | yes |
| nb324k | Human | Kidney | Adherent | no |
| neural stem cells | Rat | Brain | Either | yes |
| neuroblastoma | Human | Brain | Adherent | yes |
| nci-h23 | Human | Lung | Adherent | no |
| nci-h460 | Human | Lung | Adherent | no |
| neurons (astrocytes) | Rat | Brain | Adherent | yes |
| neuro 2a, a murine neuroblastoma cell line | Mouse | Neuroblastoma | Adherent | no |
| nbt-ii | Rat | Bladder | Adherent | no |
| neuons (astrocytes) | Rat | Astrocyte | Adherent | yes |
| nci-h295 | Human | Kidney | Adherent | no |
| nci-h358 | Human | Lung | Adherent | no |
| neuons (hippocampal & septal) | Rat | Brain | Adherent | yes |
| neurons | Mouse | Brain | Adherent | yes |
| nhdf | Human | Fibroblast | Adherent | no |
| neurons (post-natal/adult) | Rat | Brain | Adherent | yes |
| nhbe | Human | Lung | Adherent | yes |
| ng108-15 | Mouse | Neuroblastoma | Adherent | no |
| neurons (embryonic cortical) | Rat | Brain | Adherent | yes |
| neurons (cortical) | Mouse | Other | Adherent | yes |
| ng 125 | Human | Neuroblastoma | Adherent | no |
| nhf3 | Human | Fibroblast | Adherent | no |
| *neurospora crassa* | Fungi | Embryo | Adherent | yes |
| neurons (superior cervical ganglia - scg) | Rat | Brain | Adherent | yes |
| neurons (ganglia) | Frog | Brain | Either | yes |
| ns20y | Mouse | Neuroblastoma | Adherent | no |
| nrk | Rat | Fibroblast | Adherent | yes |
| nmumg | Mouse | Breast/Mammary | Adherent | no |
| o23 | Hamster | Fibroblast | Adherent | no |
| nt2 | Human | Fibroblast | Adherent | no |
| nhff | Human | Foreskin | Adherent | yes |
| nih 3t3, 3t3-l1 | Mouse | Fibroblast | Adherent | no |
| ohio helas | Human | Cervix | Suspension | no |
| nih 3t6 | Mouse | Fibroblast | Adherent | no |
| nih 3t3-l1, nih 3t3 | Mouse | Embryo | Adherent | no |
| nt2-d1 | Human | Testes | Adherent | no |

TABLE 1-continued

Example cell types used as a basis for providing cell context in some embodiments.

| Cell Name | Tissue Type | Tissue | Phenotype | Primary |
|---|---|---|---|---|
| nih 3t3-l1, nih 3t3 ( ) | Mouse | Embryo | Adherent | no |
| orbital fibroblast | Human | Fibroblast | Adherent | yes |
| osteoblasts | Rat | Bone | Adherent | yes |
| p19 cells | Mouse | Embryo | Adherent | yes |
| ovcar-3 | Human | Ovary | Adherent | no |
| opaec cells | Sheep | Endothelial | Adherent | no |
| ovarian surface epithelial (ose) | Human | Ovary | Adherent | yes |
| p388d1 | Mouse | Macrophage | Adherent | yes |
| p825, mastocytoma cells | Mouse | Macrophage | Adherent | yes |
| p19cl6 | Mouse | Heart | Adherent | no |
| omega e | Mouse | Embryo | Adherent | no |
| ok, derived from renal proximal tubules | Opossum | Kidney | Adherent | yes |
| p815, mastocytoma cells | Mouse | Macrophage | Adherent | yes |
| p3.653 × ag8 murine myeloma cells | Mouse | Bone marrow | Adherent | yes |
| paju, human neural crest-derived cell line | Human | Brain | Adherent | yes |
| pac-1 | Rat | Aorta | Adherent | no |
| parp−/− mouse embryonic fibroblasts | Mouse | Fibroblast | Suspension | no |
| pci-13 | Human | Skin | Adherent | no |
| pc 6 (pheochromocytoma-6) | Rat | Glial | Adherent | no |
| pancreatic islets | Rat | Pancreas | Adherent | yes |
| peripheral blood lymphocytes | Human | Blood | Either | yes |
| pc-3 | Human | Prostate | Either | no |
| pc-12 | Rat | Brain | Adherent | no |
| panc1 | Human | Pancreas | Adherent | no |
| per.c6 ® | Human | Retina | Either | no |
| pa 317 or pt67 mouse fibroblast with herpes thymidine kinase (tk) gene | Mouse | Fibroblast | Adherent | yes |
| pam212, mouse keratinocytes | Mouse | Keratinocyte | Adherent | yes |
| peripheral blood mononuclear cells (pbmc) | Human | Blood | Suspension | yes |
| qt6 | Quail | Fibroblast | Adherent | no |
| pu5-1.8 cells | Mouse | Macrophage | Suspension | no |
| primary lymphoid (oka) organ from penaeus shrimp | Shrimp | Lymphocyte | Adherent | yes |
| ps120, an nhe-deficient clone derived from ccl39 cells | Hamster | Lung | Adherent | yes |
| phoenix-eco cells | Human | Embryo | Adherent | no |
| quail embryos | Quail | Embryo | Either | yes |
| plb985 | Human | Blood | Suspension | no |
| rabbit pleural mesothelial | Rabbit | Lung | Adherent | no |
| r1 embryonic stem cell, es | Mouse | Embryo | Either | no |
| rabbit vsmc, vascular smooth muscle cells | Rabbit | Muscle | Adherent | yes |
| raec, rat aortic endothelial cells | Rat | Aorta | Adherent | yes |
| raji | Human | Lymphocyte | Suspension | no |
| rat epithelial cells | Rat | Epithelial | Adherent | yes |
| raw 264.7 cells, murine macrophage cells | Mouse | Macrophage | Adherent | yes |
| ramos | Human | Lymphocyte | Suspension | no |
| rat hepatic ito cells | Rat | Liver | Adherent | yes |
| rat adipocyte | Rat | Adipose | Adherent | yes |
| rat c5, glioma cells | Rat | Glial | Adherent | yes |
| rat-1, rat fibroblasts | Rat | Fibroblast | Adherent | yes |
| rat 2, rat fibroblasts | Rat | Fibroblast | Adherent | yes |
| rat glomerular mesangial mc cells | Rat | Kidney | Adherent | yes |
| raw cells | Rat | Peritoneum | Suspension | no |
| rat-6 (r6), rat embryo fibroblast | Rat | Fibroblast | Adherent | yes |

TABLE 1-continued

Example cell types used as a basis for providing cell context in some embodiments.

| Cell Name | Tissue Type | Tissue | Phenotype | Primary |
|---|---|---|---|---|
| hmec-1 | Human | Endothelial | Adherent | yes |
| hre h9 | Rabbit | Uterus | Adherent | no |
| hmn 1 | Mouse | Neuroblastoma | Adherent | yes |
| ht-29 | Human | Colon | Adherent | no |
| hos | Human | Osteoblast | Adherent | no |
| hs68 | Human | Foreskin | Adherent | yes |
| hmcb | Human | Skin | Adherent | no |
| hs-578t | Human | Breast/Mammary | Adherent | no |
| hnscc | Human | Skin | Adherent | no |
| hpb-all | Human | Lymphocyte | Suspension | no |
| hmvec-l | Human | Lung | Adherent | no |
| hsy-eb | Human | Other | Adherent | no |
| huh 7 | Human | Liver | Adherent | no |
| htlm2 | Mouse | Breast/Mammary | Adherent | yes |
| hut 78 | Human | Skin | Suspension | no |
| ht1080 | Human | Fibroblast | Adherent | no |
| huvec, huaec | Human | Umbilicus | Adherent | yes |
| htla230 | Human | Neuroblastoma | Adherent | yes |
| hybridoma | Mouse | Spleen | Suspension | no |
| ib3-1 | Human | Lung | Adherent | no |
| ht22 | Mouse | Brain | Adherent | yes |
| human skeletal muscle | Human | Muscle | Adherent | yes |
| ht4 | Human | Testes | Adherent | yes |
| hutu 80 | Human | Colon | Adherent | yes |
| in vivo mouse brain | Mouse | Bone | Either | yes |
| in vivo rat brain | Rat | Brain | Either | yes |
| iec-6 rie | Rat | Epithelial | Adherent | no |
| imr-32 | Human | Neuroblastoma | Adherent | no |
| ic11 | Mouse | Testes | Adherent | no |
| imr-90 | Human | Lung | Adherent | no |
| in vivo rat lung | Rat | Lung | Either | yes |
| in vivo rat liver | Rat | Liver | Either | yes |
| ins-1 | Rat | Pancreas | Adherent | no |
| in vivo rabbit eye | Rabbit | Other | Either | yes |
| in vivo mouse | Mouse | Other | Either | yes |
| imdf | Mouse | Skin | Adherent | no |
| in vivo pig | Pig | Other | Either | yes |
| caski | Human | Cervix | Adherent | no |
| cerebellar | Mouse | Brain | Adherent | yes |
| cd34+ monocytes | Human | Monocyte | Suspension | yes |
| cfk2 | Rat | Bone | Adherent | no |
| cem | Human | Blood | Suspension | no |
| catha, cath.a | Mouse | Brain | Either | no |
| ccl-16-b9 | Hamster | Lung | Adherent | no |
| ch12f3-2a | Mouse | Lymphocyte | Suspension | no |
| cf2th | Dog | Thymus | Adherent | no |
| cardiomyocytes | Human | Heart | Adherent | yes |
| cg-4 | Rat | Glial | Adherent | no |
| cell.220(b8) | Human | Default | Suspension | no |
| cardiomyocytes | Rat | Heart | Adherent | yes |
| chick embryo fibroblasts | Chicken | Embryo | Adherent | yes |
| chicken sperm | Chicken | Sperm | Adherent | yes |
| cho k1 | Hamster | Ovary | Adherent | no |
| cho 58 | Hamster | Ovary | Adherent | no |
| cho-b7 | Hamster | Ovary | Adherent | no |
| chick embryo blastodermal cells | Chicken | Embryo | Adherent | yes |
| cho -b53 | Hamster | Ovary | Adherent | yes |
| chick embryo chondrocytes | Chicken | Embryo | Adherent | yes |
| chinese hamster lung | Hamster | Lung | Adherent | no |
| cho dg44 | Hamster | Ovary | Either | no |
| cho - b53 jf7 | Hamster | Ovary | Adherent | yes |
| chicken hepatocytes | Chicken | Liver | Adherent | yes |
| cos-1 | Primate - Non Human | Kidney | Adherent | no |
| cho-lec1 | Hamster | Ovary | Adherent | yes |
| clone a | Human | Colon | Adherent | no |
| cho-lec2 | Hamster | Ovary | Adherent | no |
| colo205 | Human | Colon | Adherent | no |
| chu-2 | Human | Epithelial | Adherent | no |
| cmt-93 | Mouse | Rectum | Adherent | no |
| cho-s | Hamster | Ovary | Suspension | no |
| cho-leu c2gnt | Hamster | Ovary | Adherent | no |
| cho-trvb | Hamster | Ovary | Adherent | no |

TABLE 1-continued

Example cell types used as a basis for providing cell context in some embodiments.

| Cell Name | Tissue Type | Tissue | Phenotype | Primary |
|---|---|---|---|---|
| clone-13, mutant b lymphoblastoid | Human | Lymphocyte | Suspension | no |
| cj7 | Mouse | Embryo | Adherent | no |
| smooth muscle cells (aortic) | Rat | Muscle | Adherent | yes |
| splenocytes | Mouse | Spleen | Suspension | yes |
| smooth muscle cells (vascular) | Rat | Muscle | Adherent | yes |
| sp1 | Mouse | Breast/Mammary | Adherent | no |
| stem | Rat | Bone | Suspension | yes |
| spoc-1 | Rat | Trachael | Adherent | no |
| snb19 | Human | Brain | Adherent | no |
| splenocytes (resting b cells) | Mouse | Spleen | Suspension | yes |
| splenocytes (b cells t2) | Mouse | Spleen | Suspension | yes |
| svr | Mouse | Pancreas | Adherent | no |
| stem cells | Human | Bone marrow | Suspension | yes |
| smooth muscle cells (vascular) | Human | Muscle | Adherent | yes |
| smooth muscle cells (vascular) | Rabbit | Aorta | Adherent | yes |
| t3cho/at1a | Hamster | Ovary | Either | no |
| t-rex-cho | Hamster | Ovary | Adherent | no |
| t-rex-293 | Human | Kidney | Adherent | no |
| sw620 | Human | Colon | Adherent | no |
| t lymphocytes (t cells) | Mouse | Lymphocyte | Adherent | yes |
| t lymphocytes cytotoxic (ctl) cells | Mouse | Lymphocyte | Either | yes |
| sw480 | Human | Colon | Adherent | no |
| t lymphocytes (t cells) | Human | Lymphocyte | Adherent | yes |
| sw13 | Human | Adrenal gland/cortex | Adherent | no |
| t47d, t-47d | Human | Breast/Mammary | Adherent | no |
| t24 | Human | Bladder | Adherent | no |
| t-rex hela | Human | Cervix | Adherent | no |
| tr2 | Mouse | Brain | Adherent | no |
| tig | Human | Fibroblast | Adherent | yes |
| t98g | Human | Brain | Adherent | no |
| tsa201 | Human | Embryo | Adherent | no |
| tobacco protoplasts | Plant | Other | Suspension | yes |
| thp-1 | Human | Blood | Suspension | yes |
| tk.1 | Mouse | Lymphocyte | Suspension | no |
| tib-90 | Mouse | Fibroblast | Adherent | no |
| ta3 | Mouse | Breast/Mammary | Adherent | no |
| tyknu cells | Human | Ovary | Adherent | no |
| u-937 | Human | Macrophage | Suspension | no |
| tgw-nu-1 | Human | Bladder | Adherent | no |
| b-lcl | Human | Blood | Suspension | no |
| b4.14 | Primate - Non Human | Kidney | Adherent | yes |
| b82 m721 | Mouse | Fibroblast | Adherent | no |
| b-tc3 | Mouse | Pancreas | Adherent | no |
| b16-f10 | Mouse | Melanoma | Adherent | no |
| b82 | Mouse | Fibroblast | Adherent | no |
| as52 | Hamster | Ovary | Adherent | no |
| b lymphocytes | Human | Blood | Suspension | yes |
| b35 | Rat | Neuroblastoma | Adherent | yes |
| b65 | Rat | Neuroblastoma | Adherent | no |
| b11 | Mouse | Spleen | Suspension | no |
| att-20 | Mouse | Pituitary | Adherent | no |
| bcl-1 | Mouse | Lymphocyte | Adherent | no |
| bac | Cow | Adrenal Gland | Adherent | yes |
| balb/c 3t3, 3t3-a31 | Mouse | Fibroblast | Adherent | no |
| be(2)-c | Human | Neuroblastoma | Adherent | no |
| bewo | Human | Other | Adherent | no |
| balb/mk | Mouse | Epithelial | Adherent | no |
| beas-2b | Human | Lung | Adherent | no |
| bewo | Human | Uterus | Adherent | yes |
| baf3, ba/fi | Mouse | Lymphocyte | Suspension | no |
| bcec | Human | Brain | Adherent | yes |
| bc3h1 | Mouse | Brain | Adherent | yes |
| baec | Cow | Aorta | Adherent | no |
| a10 | Rat | Muscle | Adherent | no |
| a1.1 | Mouse | Lymphocyte | Adherent | yes |
| a72 | Dog | Connective | Adherent | no |

TABLE 1-continued

Example cell types used as a basis for providing cell context in some embodiments.

| Cell Name | Tissue Type | Tissue | Phenotype | Primary |
|---|---|---|---|---|
| a549 | Human | Lung | Adherent | no |
| a204 | Human | Muscle | Adherent | yes |
| a6 | Frog | Kidney | Adherent | no |
| a875 | Human | Melanoma | Adherent | yes |
| a498 | Human | Kidney | Adherent | no |
| a172 | Human | Brain | Adherent | yes |
| a-431 | Human | Skin | Adherent | no |
| a20 | Mouse | Lymphocyte | Suspension | yes |
| arpe-19 | Human | Retina | Adherent | no |
| alpha t3 | Human | Pituitary | Adherent | no |
| akr | Mouse | Spleen | Adherent | no |
| ar4-2j | Rat | Pancreas | Adherent | no |
| aortic endothelial cells | Human | Aorta | Adherent | yes |
| achn | Human | Kidney | Adherent | yes |
| adventitial fibroblasts | Human | Aorta | Adherent | yes |
| am12 | Mouse | Blood | Suspension | no |
| anterior pituitary gonadotropes | Human | Pituitary | Adherent | yes |
| ae-1 | Mouse | Spleen | Suspension | no |
| ab1 | Mouse | Embryo | Adherent | no |
| anjou 65 | Human | Default | Either | no |
| crfk | Cat | Kidney | Adherent | no |
| d.mel-2 | Insect | Embryo | Either | no |
| ct26 | Mouse | Colon | Either | yes |
| cowpea plant embryos | Fungi | Embryo | Adherent | yes |
| cos-7 | Primate - Non Human | Kidney | Adherent | no |
| crl6467 | Mouse | Liver | Adherent | no |
| cwr22rv1 | Human | Prostate | Adherent | no |
| ct60 | Hamster | Ovary | Adherent | no |
| cos-gs1 | Primate - Non Human | Kidney | Adherent | no |
| cos-m6 | Primate - Non Human | Kidney | Adherent | yes |
| cv-1 | Primate - Non Human | Kidney | Adherent | no |
| ctll-2 | Mouse | Lymphocyte | Suspension | no |
| d3 embryonic stem cells | Mouse | Embryo | Adherent | no |
| du145 | Human | Prostate | Adherent | no |
| do-11.10 | Mouse | Lymphocyte | Suspension | no |
| daudi | Human | Lymphocyte | Suspension | no |
| d10 | Mouse | Lymphocyte | Suspension | no |
| dgz | Plant | Other | Adherent | yes |
| dictyostelium | Amoeba | Other | Suspension | yes |
| dt40 | Chicken | Bursa | Suspension | no |
| *drosophila* kc | Insect | Embryo | Adherent | yes |
| df1 | Chicken | Fibroblast | Adherent | no |
| dc 2.4 cells | Mouse | Blood | Either | no |
| daoy | Human | Other | Adherent | no |
| lovo | Human | Colon | Adherent | no |
| lncap | Human | Prostate | Adherent | no |
| m21 | Human | Melanoma | Adherent | no |
| lsv5 | Human | Keratinocyte | Adherent | no |
| ltk | Mouse | Connective | Adherent | no |
| m1 | Rat | Embryo | Adherent | no |
| m3z | Human | Breast/Mammary | Adherent | no |
| m21-l | Human | Melanoma | Adherent | no |
| lymphoid cell line | Rat | Lymphocyte | Suspension | no |
| m-imcd | Mouse | Kidney | Adherent | yes |
| m12.4 | Mouse | Lymphocyte | Adherent | no |
| m21-14 | Human | Melanoma | Adherent | no |
| mat b iii | Rat | Breast/Mammary | Adherent | no |
| mda-mb-453 | Human | Breast/Mammary | Adherent | no |
| mca-rh7777 | Rat | Liver | Adherent | no |
| ma104 | Primate - Non Human | Kidney | Adherent | no |
| magi-ccr5 | Human | Epithelial | Adherent | no |
| mda-mb-231 | Human | Breast/Mammary | Adherent | no |
| mcf-10 | Human | Breast/Mammary | Adherent | no |
| mc3t3-e1 | Mouse | Osteoblast | Adherent | no |
| mc ardle 7777 | Rat | Liver | Either | yes |
| macrophages | Mouse | Peritoneum | Adherent | yes |
| mcf-7 | Human | Breast/Mammary | Adherent | no |
| macrophages | Human | Blood | Either | yes |
| maize protoplasts | Plant | Other | Adherent | no |

TABLE 1-continued

Example cell types used as a basis for providing cell context in some embodiments.

| Cell Name | Tissue Type | Tissue | Phenotype | Primary |
|---|---|---|---|---|
| umr 106-01 | Rat | Bone | Adherent | no |
| uc729-6 | Human | Lymphocyte | Either | no |
| u9737 | Human | Lymphocyte | Suspension | no |
| uok257 | Human | Kidney | Adherent | no |
| u373mg | Human | Astrocyte | Adherent | no |
| wit49 wilms tumor | Human | Lung | Either | yes |
| vero | Primate - Non Human | Kidney | Adherent | no |
| u87, u87mg | Human | Astrocyte | Adherent | no |
| umrc6 | Human | Kidney | Adherent | no |
| u251 cells | Human | Glial | Adherent | no |
| u2os | Human | Bone | Adherent | no |
| bovine chromaffin cells | Cow | Adrenal Gland | Adherent | yes |
| bowes melanoma cells | Human | Skin | Adherent | no |
| boll weevil brl-ag-3c | Insect | Other | Adherent | no |
| bm5 | Insect | Ovary | Suspension | no |
| bhk-21 | Hamster | Kidney | Either | no |
| bosc 23 | Human | Kidney | Adherent | yes |
| bms-black mexican sweet protoplasts | Default | Default | Suspension | yes |
| bfc012 | Mouse | Embryo | Adherent | no |
| bone marrow cells | Mouse | Bone marrow | Suspension | yes |
| bone marrow derived stromal cells | Human | Bone marrow | Adherent | yes |
| bs-c-1, bsc-1 | Primate - Non Human | Kidney | Adherent | no |
| bjab | Human | Lymphocyte | Suspension | no |
| bnl cl.2 (cl2) | Mouse | Liver | Adherent | no |
| btm (bovine trachael myocytes) | Cow | Muscle | Adherent | no |
| c2c12 | Mouse | Muscle | Adherent | no |
| c3a | Human | Liver | Adherent | no |
| c1.39t | Human | Fibroblast | Adherent | no |
| bt cells | Cow | Fibroblast | Adherent | no |
| bsc-40 | Primate - Non Human | Kidney | Adherent | no |
| c33 | Human | Cervix | Adherent | no |
| c1c12 | Mouse | Muscle | Adherent | no |
| c127 | Mouse | Epithelial | Adherent | no |
| bt549 | Human | Breast/Mammary | Adherent | no |
| c1r, hmy2.c1r | Human | Lymphocyte | Adherent | yes |
| c13-nj | Human | Glial | Adherent | no |
| canine gastric parietal cells | Dog | Stomach | Adherent | yes |
| calu-3 | Human | Lung | Adherent | yes |
| cak | Mouse | Fibroblast | Adherent | no |
| c57bl/6 cells | Mouse | Heart | Adherent | no |
| caco-2 cells | Human | Colon | Adherent | no |
| c3h 10t1/2 | Mouse | Fibroblast | Adherent | no |
| ca77 | Rat | Thyroid | Adherent | no |
| c6 cells | Rat | Brain | Adherent | no |
| calu-6 | Human | Lung | Adherent | no |
| capan-2 | Human | Pancreas | Adherent | no |
| c4-2 | Human | Prostate | Adherent | no |
| 143b | Human | Bone marrow | Either | no |
| 1064sk | Human | Foreskin | Adherent | yes |
| 16-9 | Human hamster hybrid cell line - transfected with two human genes | Other | Adherent | no |
| 2008 | Human | Ovary | Adherent | no |
| 208f | Rat | Fibroblast | Adherent | no |
| 293-h | Human | Kidney | Either | no |
| 293 | Human | Kidney | Either | no |
| 293 ebna | Human | Kidney | Adherent | no |
| 293t | Human | Kidney | Either | no |
| 2pk3 | Mouse | Lymphocyte | Suspension | no |
| 293-f | Human | Kidney | Either | no |
| 2780 | Human | Ovary | Adherent | no |
| 293s | Human | Kidney | Either | no |
| 2774 | Human | Ovary | Adherent | no |
| 3y1 | Rat | Fibroblast | Adherent | yes |
| 82-6 | Human | Fibroblast | Adherent | no |
| 9hte | Human | Trachael | Adherent | yes |
| 3.12 | Mouse | Lymphocyte | Either | yes |

TABLE 1-continued

Example cell types used as a basis for providing cell context in some embodiments.

| Cell Name | Tissue Type | Tissue | Phenotype | Primary |
|---|---|---|---|---|
| 5637 | Human | Bladder | Adherent | no |
| 4t1 | Mouse | Breast/Mammary | Adherent | no |
| 3t3-f442a | Mouse | Other | Adherent | yes |
| 33.1.1 | Mouse | Lymphocyte | Suspension | no |
| 32d | Mouse | Bone marrow | Either | no |
| 4de4 | Mouse | Bone marrow | Either | yes |
| e1-ts20 | Human | Breast/Mammary | Adherent | yes |
| embryonic stem cells | Mouse | Embryo | Adherent | yes |
| e. histolytica | Amoeba | Other | Suspension | yes |
| ef88 | Mouse | Fibroblast | Adherent | yes |
| el-4 | Mouse | Thymus | Suspension | no |
| ebc-1 | Human | Lung | Adherent | no |
| duck (in vivo) | Duck | Other | Suspension | yes |
| ecv | Human | Endothelial | Adherent | no |
| ecr-293 | Human | Kidney | Adherent | no |
| e14tg2a | Mouse | Embryo | Adherent | no |
| e36 | Hamster | Lung | Adherent | no |
| endothelial cells (pulmonary aorta) | Rat | Aorta | Adherent | yes |
| endothelial cells (aortic) | Pig | Aorta | Adherent | yes |
| ewing sarcoma coh cells | Human | Bone | Suspension | no |
| f9 | Mouse | Testes | Adherent | no |
| fibroblasts (cardiac) | Rat | Fibroblast | Adherent | yes |
| f442-a | Mouse | Preadiopocyte | Adherent | no |
| es-2 ovarian clear cell adenocarcinoma | Human | Ovary | Adherent | no |
| fetal neurons | Rat | Brain | Adherent | yes |
| epithelial cells (sra01/04) | Human | Epithelial | Adherent | yes |
| fibroblasts (embryo) | Rat | Fibroblast | Adherent | yes |
| fgc-4 | Rat | Liver | Adherent | yes |
| fak-/- | Mouse | Embryo | Adherent | yes |
| es-d3 | Mouse | Embryo | Adherent | no |
| epithelial cells (rte) | Rat | Trachael | Adherent | yes |
| foreskin fibroblast | Human | Foreskin | Adherent | no |
| flp-in jurkat | Human | Lymphocyte | Suspension | no |
| flp-in cho | Hamster | Ovary | Adherent | no |
| fibroblasts (neonatal dermal) | Human | Skin | Adherent | yes |
| flp-in 293 | Human | Kidney | Adherent | no |
| flp-in t-rex 293 | Human | Kidney | Adherent | no |
| flp-in cv-1 | Primate - Non Human | Kidney | Adherent | no |
| fibroblasts | Chicken | Skin | Adherent | yes |
| fibroblasts (normal) | Human | Fibroblast | Adherent | yes |
| fl5.12 | Mouse | Liver | Suspension | no |
| fm3a | Mouse | Breast/Mammary | Adherent | no |
| fr | Rat | Fibroblast | Adherent | no |
| nalm6 | Human | Other | Suspension | no |

In some embodiments, the cell context includes a perturbation to the one or more cells. For example, in some embodiments, the cell context includes an environmental factor that perturbs the cell relative to a reference environment (such as a growth medium that is commonly used to culture the particular cell). For example, in some embodiments, the cell context includes a component in a growth medium that significantly changes the metabolism of the one or more cells, e.g., a compound that is toxic to the one or more cells, that slows cellular metabolism, that increases cellular metabolism, or that otherwise changes a characteristic of cellular metabolism. As another example, the perturbation could be a shift in the osmolality, conductivity, pH, or other physical characteristic of the growth environment. In some embodiments, a cell context includes a mutation within the genome of the one or more cells, e.g., a human cell line in which a gene has been mutated or deleted. In some embodiments, a cell context is a cell line that has one or more documented structural variations (e.g., a documented single nucleotide polymorphism "SNP", an inversion, a deletion, an insertion, or any combination thereof). In some such embodiments, the one or more documented structural variations are homozygous variations. In some such embodiments, the one or more documented structural variations are heterozygous variations. As an example of a homozygous variation in a diploid genome, in the case of a SNP, both chromosomes contain the same allele for the SNP. As an example of a heterozygous variation in a diploid genome, in the case of the SNP, one chromosome has a first allele for the SNP and the complementary chromosome has a second allele for the SNP, where the first and second allele are different.

In some embodiments, the different cell contexts include different cell types, e.g., different human and/or mammalian cells. In some embodiments, the different cell contexts include at least two cell contexts incorporating the same cell type, where one of the cell contexts is exposed to a perturbing agent and another cell context is not exposed to a perturbing agent. In some embodiments, the different cell contexts include multiple cell contexts incorporating the same cell type, e.g., but perturbed in different fashions. For example, in some embodiments, two cell contexts include the same cell type but are perturbed with different siRNA molecules that knock-down expression of different genes.

Accordingly, in some embodiments, the plurality of cell contexts includes two or more cell types (440). Similarly, in some embodiments, the plurality of cell contexts includes five or more cell types (442). Likewise, in some embodiments, the plurality of cell contexts includes two, three, four, five, six, seven, eight, nine, ten, or more cell types. In some embodiments, the method is performed using a single cell context.

In some embodiments, a first cell context in the plurality of cell contexts includes a first cell type and a second cell context in the plurality of cell contexts includes the first cell type exposed to a perturbing agent (444). Similarly, in come embodiments, a first cell context in the plurality of cell contexts includes a first cell type exposed to a first perturbing agent and a second cell context in the plurality of cell contexts includes the first cell type exposed to a second perturbing agent. In some embodiments, the perturbing agent is a toxin, a cytokine, a predetermined drug, a siRNA, a sgRNA, a different cell exposure to compound time, a cell type from a different donor, or a cell culture condition (446), e.g., as described further below.

In some embodiments, a first cell context in the plurality of cell contexts includes a first native cell type and a second cell context in the plurality of cell contexts consist of the first native cell type that has incurred a genetic modification (448). For example, in some embodiments, the first cell context includes a human cell (e.g., a U2OS cell or HeLa cell) and the second cell context includes the same human cell line (e.g., the U2OS cell or HeLa cell) having a mutation that is not present in the human cell of the first cell context (e.g., a point mutation, deletion, insertion, inversion, etc.). In some embodiments, the mutation is a genetic deletion or an insertion (450).

In some embodiments, a cell context is generated by perturbing a particular cell line with a small interfering RNA (siRNA), e.g., a double-stranded RNA molecule, 20-25 base pairs in length that interferes with the expression of a specific gene with a complementary nucleotide sequence by degrading mRNA after transcription preventing translation of the gene. An siRNA is an RNA duplex that can reduce gene expression through enzymatic cleavage of a target mRNA mediated by the RNA induced silencing complex (RISC). An siRNA has the ability to inhibit targeted genes with near specificity. See, Agrawal et al., 2003, "RNA interference: biology, mechanism, and applications," Microbiol Mol Biol Rev. 67: 657-85; and Reynolds et al., 2004, "Rational siRNA design for RNA interference," Nature Biotechnology 22, 326-330, each of which is hereby incorporated by reference. In some such embodiments, the perturbation is achieved by transfecting the siRNA into the one or more cells, DNA-vector mediated production, or viral-mediated siRNA synthesis. See, for example, Paddison et al., 2002, "Short hairpin RNAs (shRNAs) induce sequence-specific silencing in mammalian cells," Genes Dev. 16:948-958; Sui et al., 2002, A DNA vector-based RNAi technology to suppress gene expression in mammalian cells," Proc Natl Acad Sci USA 99:5515-5520; Brummelkamp et al., 2002, "A system for stable expression of short interfering RNAs in mammalian cells," Science 296:550-553; Paddison et al., 2004, "Short hairpin activated gene silencing in mammalian cells," Methods Mol Biol 265:85-100; Wong et al. 2003, "CIITAregulated plexin-A1 affects T-cell-dendritic cell interactions, Nat Immunol 2003, 4:891-898; Tomar et al., 2003, "Use of adeno-associated viral vector for delivery of small interfering RNA. Oncogene 22:5712-5715; Rubinson et al., 2003 "A lentivirus-based system to functionally silence genes in primary mammalian cells, stem cells and transgenic mice by RNA interference," Nat Genet 33:401-406; Moore et al., 2005, "Stable inhibition of hepatitis B virus proteins by small interfering RNA expressed from viral vectors," J Gene Med; and Tran et al., 2003, "Expressing functional siRNAs in mammalian cells using convergent transcription, BMC Biotechnol 3:21; each of which is hereby incorporated by reference.

In some embodiments, a cell context is generated by perturbing a particular cell line with a short hairpin RNA (shRNA). See, Taxman et al., 2006, "Criteria for effective design, construction, and gene knockdown by shRNA vectors," BMC Biotechnology 6:7 (2006), which is hereby incorporated by reference. In some such embodiments, the perturbation is achieved by DNA-vector mediated production, or viral-mediated siRNA synthesis as generally discussed in the references cited above for siRNA.

In some embodiments, a cell context is generated by perturbing a particular cell line with a single guide RNA (sgRNA) used in the context of palindromic repeat (e.g., CRISPR) technology. See, Sander and Young, 2014, "CRISPR-Cas systems for editing, regulating and targeting genomes," Nature Biotechnology 32, 347-355, hereby incorporated by reference, in which a catalytically-dead Cas9 (usually denoted as dCas9) protein lacking endonuclease activity to regulate genes in an RNA-guided manner. Targeting specificity is determined by complementary base-pairing of a single guide RNA (sgRNA) to the genomic loci. sgRNA is a chimeric noncoding RNA that can be subdivided into three regions: a 20 nt base-pairing sequence, a 42 nt dCas9-binding hairpin and a 40 nt terminator. In some embodiments, when designing a synthetic sgRNA, only the 20 nt base-pairing sequence is modified from the overall template. In some such embodiments, the perturbation is achieved by DNA-vector mediated production, or viral-mediated sgRNA synthesis.

In some embodiments, a cell context is optimized for non-optical measurements of features, e.g., via RNASeq, L1000, proteomics, toxicity assays, publicly available bioassay data, in-house generated bioassays, microarrays, or chemical toxicity assays, etc.

In some embodiments, a cell context is generated by perturbing a particular cell line with a cytokine or mixture of cytokines. See Heike and Nakahata, 2002, "Ex vivo expansion of hematopoietic stem cells by cytokines," Biochim Biophys Acta 1592, 313-321, which is hereby incorporated by reference. In some embodiments the cell context includes cytokines (e.g., lymphokines, chemokines, interferons, tumor necrosis factors, etc.). In some embodiments a cell context includes lymphokines (e.g., Interleukin 2, Interleukin 3, Interleukin 4, Interleukin 5, Interleukin 6, granulocyte-macrophage colony-stimulating factor, interferon gamma, etc.). In some embodiments a cell context includes chemokines such as homeostatic chemokines (e.g., CCL14, CCL19, CCL20, CCL21, CCL25, CCL27, CXCL12, CXCL13, etc.) and/or inflammatory chemokines (e.g., CXCL-8, CCL2, CCL3, CCL4, CCL5, CCL11, CXCL10). In some embodiments a cell context includes interferons (IFN) such as a type I IFN (e.g., IFN-α, IFN-β, IFN-ε, IFN-κ and IFN-ω), a type II IFN (e.g., IFN-γ), or a type III IFN. In some embodiments a cell context includes tumor necrosis factors such as TNFα or TNF alpha.

In some embodiments, a cell context is generated by perturbing a particular cell line with a protein, such as a peptide aptamer. Peptide aptamers are combinatorial reagents that bind to target proteins with a high specificity and a strong affinity. By so doing, they can modulate the function of their cognate targets. In some embodiments, a peptide aptamer comprises one (or more) conformationally constrained short variable peptide domains, attached at both ends to a protein scaffold. In some embodiments, a cell context is perturbed with peptide aptamer derivatized with one or more functional moieties that can cause specific postranslational modification of their target proteins, or change the subcellular localization of the targets. See, for example, Colas et al., 2000, "Targeted modification and transportation of cellular proteins," Proc. Natl. Acad. Sci. USA. 97 (25): 13720-13725, which is hereby incorporated by reference. In some embodiments, a cell context is perturbed with a peptide that selectively affects protein-protein interactions within an entity. In some such embodiments this protein-protein interaction affects an intracellular signaling event. See, for example, Sourouj on and Mochly-Rosen, 1998, "Peptide modulators of protein-protein interactions in intracellular signaling," Nature Biotechnology 16, 919-924, which is hereby incorporated by reference. In some embodiments, a cell context is perturbed with an antibody or other form of biologic.

In some embodiments, a cell context is generated by perturbing a particular cell line with a nucleic acid, such as a nucleic acid aptamer. Nucleic acid aptamers are short synthetic single-stranded oligonucleotides that specifically bind to various molecular targets such as small molecules, proteins, nucleic acids, and even cells and tissues. See, Ni et al., 2011, "Nucleic acid aptamers: clinical applications and promising new horizons," Curr Med Chem 18(27), 4206, which is hereby incorporated by reference. In some instance nucleic acid aptamers are selected from a biopanning method such as SELEX (Systematic Evolution of Ligands by Exponential enrichment). See, Ellington and Szostak, 1990, "In vitro selection of RNA molecules that bind specific ligands," Nature 346(6287), 818; and Tuerk and Gold, 1990, "Systematic evolution of ligands by exponential enrichment: RNA ligands to bacteriophage T4 DNA polymerase," Science 249(4968), 505, each of which is hereby incorporated by reference. The SELEX screening method begins with a random sequence library of ssDNA or ssRNA that spans 20-100 nucleotides (nt) in length. The randomization of nucleic acid sequences provides a diversity of $4^n$, with n corresponding to the number of randomized bases. Diversities on the order of $\sim 10^{16}$ aptamers can typically generated and screened in the SELEX methods. Each random sequence region is flanked by constant sequences that is used for capture or priming. To overcome exonuclease degradation, aptamers can be chemically synthesized and capped with modified or inverted nucleotides to prevent terminal degradation. Modified oligonucleotides can also be incorporated within the aptamer, either during or after selection, for enhanced endonuclease stability. Some modified nucleotide triphosphates, particularly 2'-O-modified pyrimidines, can be efficiently incorporated into nucleic acid aptamer transcripts by T7 RNA polymerases. Common chemical modifications included during selection are 2'-amino pyrimidines and 2'-fluoro pyrimidines. See, Ni et al., 2011, "Nucleic acid aptamers: clinical applications and promising new horizons," Curr Med Chem 18(27), 4206, which is hereby incorporated by reference.

In some embodiments, a cell context is generated by perturbing a particular cell line with a zinc finger transcription factor. In some such embodiments, the zinc finger protein transcription factor is encoded into vector that is transformed into the one or more cells, thereby causing the control of expression of one or more targeted components within the one or more cells. In some such embodiments, a sequence that is common to multiple (e.g., functionally related) components in the entity is used by a perturbation in the form of a zinc finger protein in order to control the transcription of all these component with a single perturbation in the form of a zinc finger transcription factor. In some embodiments, the perturbation in the form of a zinc finger transcription factor targets a family of related components in an entity by targeting and modulating the expression of the endogenous transcription factors that control them. See, for example, Doyon, 2008, "Heritable targeted gene disruption in zebrafish using designed zinc-finger nucleases," Nature Biotechnology 26, 702-708, which is hereby incorporated by reference.

Features

Each of the feature measurements 216 used to form the basis of elements of instance vectors 212, or corresponding dimension reduction components thereof, or compound vectors 220, or corresponding dimension reduction components thereof, is selected from a plurality of measured features. In some embodiments, the one or more feature measurements include one or more of morphological features, expression data, genomic data, epigenomic data, epigenetic data, proteomic data, metabolomics data, toxicity data, bioassay data, etc.

In some embodiments, the corresponding set of elements includes between 5 test elements and 100,000 test elements (454). Likewise, in some embodiments, the corresponding set of elements includes a range of elements falling within the larger range discussed above, e.g., from 100 to 100,000, from 1000 to 100,000, from 10,000 to 100,000, from 5 to 10,000, from 100 to 10,000, from 1000 to 10,000, from 5 to 1000, from 100 to 1000, and the like. Generally, the more elements included in the test set, the more information available to distinguish the effects of the compounds from each other. On the other hand, as the number of elements in the set increases, the computational resources required to process the data and manipulate the multi-dimensional vectors also increases.

In some embodiments, each feature 216 in the plurality of features is an optical feature that is optically measured (456), e.g., using fluorescent labels (e.g., cell painting) or using native imaging, as described herein and known to the skilled artisan. In some embodiments, when each feature is an optical feature, a single image collection step (e.g., that obtains a single image or a series of images at multiple wavebands) can be used to collect image data from multiple samples, e.g., an entire multiwell plate. In some embodiments, a number of images are collected for each well in a multiwell plate. Feature extraction is then performed electronically from the collected image(s), limiting the experimental time required to extract features from a large plurality of cell contexts and compounds.

In some embodiments, a first subset of the plurality of features 216 are optical features that are optically measured (e.g., e.g., using fluorescent labels (e.g., cell painting)), and a second subset of the plurality of features 216 are non-optical features (458). Non-limiting examples of non-optical features include gene expression, protein levels, single end-point bio-assays, metabolome data, microenvironment data, microbiome data, genome sequence and associated features (e.g., epigenetic data such as methylation, 3D genome structure, chromatin accessibility, etc.), and a relationship and/or change in a particular feature over time, e.g., within a single sample or across a plurality of samples in a time series. Further details about these and other types of non-optical features, as well as collection of data associated with these features, is provided below.

In some embodiments, each feature 216 in the plurality of features is a feature that is non-optically measured (460). Non-limiting examples of non-optical features include gene expression, protein levels, single endpoint bio-assays, metabolome data, microenvironment data, microbiome data, genome sequence and associated features (e.g., epigenetic data such as methylation, 3D genome structure, chromatin accessibility, etc.), and a relationship and/or change in a particular feature over time, e.g., within a single sample or across a plurality of samples in a time series. Further details about these and other types of non-optical features, as well as collection of data associated with these features, is provided below. Thus, in some embodiments, multiple assays are performed for each instance (e.g., replicate) of a respective cell context that is exposed to a respective compound, e.g., both a nucleic acid microarray assay and a bioassay are performed from different instances of a respective cell context exposed to a respective compound.

In some embodiments, one or more of the features is determined from a non-cell-based assay. That is, in some embodiments, data collected from in vitro experiments performed in the absence of a cell is used in the construction of the multi-dimensional vectors described herein.

Optically-Measured Features

In some embodiments, one or more of the features represent morphological features of a cell, or an enumerated portion of a cell, upon exposure of a respective compound in the cell context. Example features include, but are not limited to cell area, cell perimeter, cell aspect ratio, actin content, actin texture, cell solidity, cell extent, cell nuclear area, cell nuclear perimeter, cell nuclear aspect ratio, and algorithm-defined features (e.g., latent features). In some embodiment, example features include, but are not limited to, any of the features found in Table S2 of the reference Gustafsdottir S M, et al., PLoS ONE 8(12): e80999. doi: 10.1371/journal.pone.0080999 (2013), which is hereby incorporated by reference.

In some embodiments, such morphological features are measured and acquired using the software program Cellprofiler. See Carpenter et al., 2006, "CellProfiler: image analysis software for identifying and quantifying cell phenotypes," Genome Biol. 7, R100 PMID: 17076895; Kamentsky et al., 2011, "Improved structure, function, and compatibility for CellProfiler: modular high-throughput image analysis software," Bioinformatics 2011/doi. PMID: 21349861 PMCID: PMC3072555; and Jones et al., 2008, CellProfiler Analyst: data exploration and analysis software for complex image-based screens, BMC Bioinformatics 9(1):482/doi: 10.1186/1471-2105-9-482. PMID: 19014601 PMCID: PMC261443, each of which is hereby incorporated by reference.

In some embodiments, the measurement one or more different feature 216 in the plurality of features is a fluorescent microscopy measurement of the different feature (406). In some embodiments, the one or more optical emitting compounds are dyes and wherein the vector for a compound in the plurality of compounds includes respective measurements of features in the plurality of features for the cell context in the presence of each of at least three different dyes (418). In some embodiments, the one or more optical emitting compounds are dyes and wherein the vector for a compound in the plurality of compounds includes respective measurements of features in the plurality of features for the cell context in the presence of each of at least five different dyes (420).

Accordingly, in some embodiments, one or more feature is measured after exposure of the cell context to the compound and to a panel of fluorescent stains that emit at different wavelengths, such as Concanavalin A/Alexa Fluor 488 conjugate (Invitrogen, cat. no. C11252), Hoechst 33342 (Invitrogen, cat. no. H3570), SYTO 14 green fluorescent nucleic acid stain (Invitrogen, cat. no. S7576), Phalloidin/Alexa Fluor 568 conjugate (Invitrogen, cat. no. A12380), and/or MitoTracker Deep Red (Invitrogen, cat. no. M22426). In some embodiments, measured features include one or more of staining intensities, textural patterns, size, and shape of the labeled cellular structures, as well as correlations between stains across channels, and adjacency relationships between cells and among intracellular structures. In some embodiments, two, three, four, five, six, seven, eight, nine, ten, or more than 10 fluorescent stains, imaged in two, three, four, five, six, seven, or eight channels, are used to measure features including different cellular components and/or compartments.

In some embodiments, one or more features 216 are measured from single cells, groups of cells, and/or a field of view. In some embodiments, features are measured from a compartment or a component (e.g., nucleus, endoplasmic reticulum, nucleoli, cytoplasmic RNA, F-actin cytoskeleton, Golgi, plasma membrane, mitochondria) of a single cell. In some embodiments, each channel includes (i) an excitation wavelength range and (ii) a filter wavelength range in order to capture the emission of a particular dye from among the set of dyes the cell has been exposed to prior to measurement. An example of the dye that is being invoked and the type of cellular component that is measured as a features for five suitable channels is provided in Table 2 below, which is adapted from Table 1 of Bray et al., 2016, "Cell Painting, a high-content image-based assay for morphological profiling using multiplexed fluorescent dyes," Nature Protocols, 11, p. 1757-74, which is hereby incorporated by reference.

TABLE 2

Example channels used for measuring features

| Channel | Dye | Filter (excitation; nm) | Filter (emission; nm) | Entity component or compartment |
|---|---|---|---|---|
| 1 | Hoechst 33342 | 387/11 | 417-477 | Nucleus |
| 2 | Concanavalin A/Alexa Fluor 488 conjugate | 472/30a | 503-538a | Endoplasmic reticulum |
| 3 | SYTO 14 green fluorescent nucleic acid stain | 531/40 | 573-613 | Nucleoli, cytoplasmic RNAb |

TABLE 2-continued

Example channels used for measuring features

| Channel | Dye | Filter (excitation; nm) | Filter (emission; nm) | Entity component or compartment |
|---|---|---|---|---|
| 4 | Phalloidin/Alexa Fluor 568 conjugate, wheat-germ agglutinin/Alexa Fluor 555 conjugate | 562/40 | 622-662c | F-actin cytoskeleton, Golgi, plasma membrane |
| 5 | MitoTracker Deep Red | 628/40 | 672-712 | Mitochondria |

Cell Painting and related variants of cell painting represent another form of imaging technique that holds promise. Cell painting is a morphological profiling assay that multiplexes six fluorescent dyes, imaged in five channels, to reveal eight broadly relevant cellular components or organelles. Cells are plated in multiwell plates, perturbed with the treatments to be tested, stained, fixed, and imaged on a high-throughput microscope. Next, automated image analysis software identifies individual cells and measures any number between one and tens of thousands (but most often approximately 1,000) morphological features (various measures of size, shape, texture, intensity, etc. of various whole-cell and sub-cellular components) to produce a profile that is suitable for the detection of even subtle phenotypes. Profiles of cell populations treated with different experimental perturbations can be compared to suit many goals, such as identifying the phenotypic impact of chemical or genetic perturbations, grouping compounds and/or genes into functional pathways, and identifying signatures of disease. See, Bray et al., 2016, Nature Protocols 11, 1757-1774.

In some embodiments, the measurement of the different feature in the plurality of features is a label-free imaging measurement of the different feature. In some embodiments, one or more feature is measured by the label-free imaging technique after exposure of the cell context to a compound. Non-invasive, label free imaging techniques have emerged, fulfilling the requirements of minimal cell manipulation for cell based assays in a high content screening context. Among these label free techniques, digital holographic microscopy (Rappaz et al., 2015 Automated multi-parameter measurement of cardiomyocytes dynamics with digital holographic microscopy," Opt. Express 23, 13333-13347) provides quantitative information that is automated for end-point and time-lapse imaging using 96- and 384-well plates. See, for example, Kuhn, J. 2013, et al., "Label-free cytotoxicity screening assay by digital holographic microscopy," Assay Drug Dev. Technol. 11, 101-107; Rappaz et al., 2014 "Digital holographic microscopy: a quantitative label-free microscopy technique for phenotypic screening," Comb. Chem. High Throughput Screen 17, 80-88; and Rappaz et al., 2015 in Label-Free Biosensor Methods in Drug Discovery (ed. Fang, Y.) 307-325, Springer Science+Business Media). Light sheet fluorescence microscopy (LSFM) holds promise for the analysis of large numbers of samples, in 3D high resolution and with fast recording speed and minimal photo-induced cell damage. LSFM has gained increasing popularity in various research areas, including neuroscience, plant and developmental biology, toxicology and drug discovery, although it is not yet adapted to an automated HTS setting. See, Pampaloni et al., 2014, "Tissue-culture light sheet fluorescence microscopy (TC-LSFM) allows long-term imaging of three-dimensional cell cultures under controlled conditions," Integr. Biol. (Camb.) 6, 988-998; Swoger et al., 2014, "Imaging cellular spheroids with a single (selective) plane illumination microscope," Cold Spring Harb. Protoc., 106-113; and Pampaloni et al., 2013, "High-resolution deep imaging of live cellular spheroids with light-sheet-based fluorescence microscopy," Cell Tissue Res. 352, 161-177.

In some embodiments, the measurement of the different feature in the plurality of features is a bright field measurement of the different feature (410). In some embodiments, one or more feature is measured by bright field microscopy after exposure of the cell context to a compound. In contrast to measurements obtained by fluorescent microscopy, which requires exposing the cell context to one of more fluorescent stain, bright field microscopy does not require the use of stains, reducing phototoxicity and simplifying imaging setup. Although the lack of stains reduces the contrast provided in bright field images, as compared to fluorescent images, various techniques have been developed to improve cellular imaging in this fashion. For example, Quantitative Phase Microscopy relies on estimation of a phase map generated from images acquired at different focal lengths. See, for example, Curl C L, et al., Cytometry A 65:88-92 (2005), which is incorporated by reference herein. Similarly, a phase map can be measured using lowpass digital filtering, followed by segmentation of individual cells. See, for example, Ali R., et al., Proc. 5th IEEE International Symposium on Biomedical Imaging: From Nano to Macro, ISBI:181-84 (2008), which is incorporated by reference herein. Texture analysis, e.g., where cell contours are extracted after segmentation, can also be used in conjunction with bright field microscopy. See, for example, Korzynska A, et al., Pattern Anal Appl 10:301-19 (2007). Yet other techniques are also available to facilitate use of bright filed microscopy, including z-projection based methods. See, for example, Selinummi J., et al., PLoS One, 4(10):e7497 (2009).

In some embodiments, the measurement of the different feature in the plurality of features is phase contrast measurement of the different feature (412). In some embodiments, one or more feature is measured by phase contrast microscopy after exposure of the cell context to a compound. Images obtained by phase contrast or differential interference contrast (DIC) microscopy can be digitally reconstructed and quantified. See Koos, 2015, "DIC image reconstruction using an energy minimization framework to visualize optical path length distribution," Sci. Rep. 6, 30420.

Although particular imaging techniques are specifically described herein, the methods provided herein could be performed using features measured from any of a number of microscope modalities.

In some embodiments, each feature in the plurality of features represents a color, texture, or size of the cell context, or an enumerated portion of the cell context, upon exposure of the cell context to the amount of the respective compound (414). Example features include, but are not limited to cell area, cell perimeter, cell aspect ratio, actin content, actin texture, cell solidity, cell extent, cell nuclear area, cell nuclear perimeter, and cell nuclear aspect ratio. In some embodiment, example features include, but are not limited to, any of the features found in Table S2 of the reference Gustafsdottir S M, et al., PLoS ONE 8(12): e80999. doi:10.1371/journal.pone.0080999 (2013), which is hereby incorporated by reference.

In some embodiments, one or more of the measured features are latent features, e.g., extracted from an image of the cell context after exposure to the compound. In one embodiments, each respective instance of the plurality of instances of the cell context is imaged to form a corresponding two-dimensional pixelated image having a corresponding plurality of native pixel values and wherein a feature in the plurality of features comprises a result of a convolution or a series convolutions and pooling operators run against native pixel values in the plurality of native pixel values of the corresponding two-dimensional pixelated image (418). While this is an example of a latent feature that can be derived from an image, other latent features and mathematical combinations of latent features can also be used. A non-limiting example of the use of latent features in image-based profiling of cellular structure is found in Ljosa, V., et al., J Biomol. Screen., 18(10):10.1177/1087057113503553 (2013), which is incorporated herein by reference.

Non-Optically-Measured Features

In some embodiments one or more of the measured features 216 include expression data, e.g., obtained using a whole transcriptome shotgun sequencing (RNA-Seq) assay that quantifies gene expression from cells (e.g., a single cell) in counts of transcript reads mapped to gene constructs. As such, in some embodiments, RNA-Seq experiments aim at reconstructing all full-length mRNA transcripts concurrently from millions of short reads. RNA-Seq facilitates the ability to look at alternative gene spliced transcripts, post-transcriptional modifications, gene fusion, mutations/SNPs and changes in gene expression over time, or differences in gene expression in different groups or treatments. See, for example, Maher et al., 2009, "Transcriptome sequencing to detect gene fusions in cancer," Nature. 458 (7234): 97-101, which is hereby incorporated by reference. In addition to mRNA transcripts, RNA-Seq can evaluate and quantify individual members of different populations of RNA including total RNA, mRNA, miRNA, lncRNA, snoRNA, or tRNA within entities. As such, in some embodiments, one or more of the features that is measured is an individual amount of a specific RNA species as determined using RNA-Seq techniques. In some embodiments, RNA-Seq experiments produce counts of component (e.g., digital counts of mRNA reads) that are affected by both biological and technical variation. In some embodiments RNA-Seq assembly is performed using the techniques disclosed in Li et al., 2008, "IsoLasso: A LASSO Regression Approach to RNA-Seq Based Transcriptome Assembly," Cell 133, 523-536 which is hereby incorporated by reference.

In some embodiments one or more of the measured features 216 are obtained using transcriptional profiling methods such an L1000 panel that measures a set of informative transcripts. In such an approach, ligation-mediated amplification (LMA) followed by capture of the amplification products on fluorescently addressed microspheres beads is extended to a multiplex reaction (e.g., a 1000-plex reaction). For instance, cells growing in 384-well plates are lysed and mRNA transcripts are captured on oligo-dT-coated plates. cDNAs are synthesized from captured transcripts and subjected to LMA using locus-specific oligonucleotides harboring a unique 24-mer barcode sequence and a 5' biotin label. The biotinylated LMA products are detected by hybridization to polystyrene microspheres (beads) of distinct fluorescent color, each coupled to an oligonucleotide complementary to a barcode, and then stained with streptavidin-phycoerythrin. In this way, each bead can be analyzed both for its color (denoting landmark identity) and fluorescence intensity of the phycoerythrin signal (denoting landmark abundance). See Subramanian et al., "A Next Generation Connectivity Map: L1000 Platform and the First 1,000, 000 Profiles," Cell 171(6), 1437, which is hereby incorporated by reference. In some embodiments, between 500 and 1500 different informative transcripts are measured using this assay.

In some embodiments one or more of the measured features 216 are obtained using microarrays. A microarray (also termed a DNA chip or biochip) is a collection of microscopic nucleic acid spots attached to a solid surface that can be used to measure the expression levels of large numbers of genes simultaneously. Each nucleic acid spot contains picomoles of a specific nucleic acid sequence, known as probes (or reporters or oligos). These can be a short section of a gene or other nucleic acid element that are used to hybridize a cDNA or cRNA (also called anti-sense RNA) sample (called target) under high-stringency conditions. For instance, by way of a non-limiting example, in some embodiments, the microarrays such as the Affymetrix GeneChip microarray, a high density oligonucleotide gene expression array, is used. Each gene on an Affymetrix microarray GeneChip is typically represented by a probe set consisting of 11 different pairs of 25-bp oligos covering features of the transcribed region of that gene. Each pair consists of a perfect match (PM) and a mismatch (MM) oligonucleotide. The PM probe exactly matches the sequence of a particular standard genotype, often one parent of a cross, while the MM differs in a single substitution in the central, $13^{th}$ base. The MM probe is designed to distinguish noise caused by non-specific hybridization from the specific hybridization signal. See, Jiang, 2008, "Methods for evaluating gene expression from Affymetrix microarray datasets," BMC Bioinformatics 9, 284, which is hereby incorporated by reference.

In some embodiments one or more of the measured features 216 are obtained using ChIP-Seq data. See, for example, Quigley and Kintner, 2017, "Rfx2 Stabilizes Foxj 1 Binding at Chromatin Loops to Enable Multiciliated Cell Gene Expression," PLoS Genet 13, e1006538, which is hereby incorporated by reference. In some embodiments, ChIP-seq is used to determine how transcription factors and other chromatin-associated proteins influence phenotype-affecting mechanisms in entities (e.g., cells). Specific DNA sites in direct physical interaction with transcription factors and other proteins can be isolated by chromatin immunoprecipitation. ChIP produces a library of target DNA sites bound to a protein of interest (component) in vivo. Parallel sequence analyses are then used in conjunction with whole-genome sequence databases to analyze the interaction pattern of any protein with DNA (Johnson et al., 2007, "Genome-wide mapping of in vivo protein—DNA interactions," Science. 316: 1497-1502, which is hereby incorporated by reference) or the pattern of any epigenetic chromatin modifications. This can be applied to the set of ChIP-able proteins and modifications, such as transcription factors, polymerases and transcriptional machinery, structural proteins, protein modifications, and DNA modifications.

ChIP selectively enriches for DNA sequences bound by a particular protein (component) in living cells (entities). The ChIP process enriches specific cross-linked DNA-protein complexes using an antibody against the protein (component) of interest. Oligonucleotide adaptors are then added to the small stretches of DNA that were bound to the protein of interest to enable massively parallel sequencing. After size selection, all the resulting ChIP-DNA fragments are sequenced concurrently using a genome sequencer. A single sequencing run can scan for genome-wide associations with high resolution, meaning that features can be located precisely on the chromosomes. Various sequencing methods can be used. In some embodiments the sequences are analyzed using cluster amplification of adapter-ligated ChIP DNA fragments on a solid flow cell substrate to create clusters of clonal copies. The resulting high density array of template clusters on the flow cell surface is sequenced by a Genome analyzing program. Each template cluster undergoes sequencing-by-synthesis in parallel using fluorescently labelled reversible terminator nucleotides. Templates are sequenced base-by-base during each read. Then, the data collection and analysis software aligns sample sequences to a known genomic sequence to identify the ChIP-DNA fragments.

In some embodiments one or more of the measured features 216 are obtained using ATAC-seq (Assay for Transposase-Accessible Chromatin using sequencing), which is a technique used in molecular biology to study chromatin accessibility. See Buenrostro et al., 2013, "Transposition of native chromatin for fast and sensitive epigenomic profiling of open chromatin, DNA-binding proteins and nucleosome position," Nature Methods 10, 1213-1218, which is hereby incorporated by reference. In some embodiments, ATAC-seq make use of the action of the transposase Tn5 on the genomic DNA of an entity. See, for example, Buenrostro et al., 2015, "ATAC-seq: A Method for Assaying Chromatin Accessibility Genome-Wide," Current Protocols in Molecular Biology: 21.29.1-21.29.9, which is hereby incorporated by reference. Transposases are enzymes catalyzing the movement of transposons to other parts in the genome. While naturally occurring transposases have a low level of activity, ATAC-seq employs a mutated hyperactive transposase. The high activity allows for highly efficient cutting of exposed DNA and simultaneous ligation of specific sequences, called adapters. Adapter-ligated DNA fragments are then isolated, amplified by PCR and used for next generation sequencing. See Buenrostro et al., 2013, "Transposition of native chromatin for fast and sensitive epigenomic profiling of open chromatin, DNA-binding proteins and nucleosome position," Nature Methods 10, 1213-1218, which is hereby incorporated by reference.

While not intending to be limited to any particular theory, transposons are believed to incorporate preferentially into genomic regions free of nucleosomes (nucleosome-free regions) or stretches of exposed DNA in general. Thus enrichment of sequences from certain loci in the genome indicates absence of DNA-binding proteins or nucleosome in the region. An ATAC-seq experiment will typically produce millions of next generation sequencing reads that can be successfully mapped on the reference genome. After elimination of duplicates, each sequencing read points to a position on the genome where one transposition (or cutting) event took place during the experiment. One can then assign a cut count for each genomic position and create a signal with base-pair resolution. This signal is used as a features in some embodiments of the present disclosure. Regions of the genome where DNA was accessible during the experiment will contain significantly more sequencing reads (since that is where the transposase preferentially acts), and form peaks in the ATAC-seq signal that are detectable with peak calling tools. In some embodiments, such peaks, and their locations in the genome are used as features. In some embodiments, these regions are further categorized into the various regulatory element types (e.g., promoters, enhancers, insulators, etc.) by integrating further genomic and epigenomic data such as information about histone modifications or evidence for active transcription. Inside the regions where the ATAC-seq signal is enriched, one can also observe sub-regions with depleted signal. These sub-regions, typically only a few base pairs long, are considered to be "footprints" of DNA-binding proteins. In some embodiments, such footprints, or their absence or presence thereof are used as features.

In some embodiments flow cytometry methods using Luminex beads, are used to obtain values for one or more of the measured features 216. See for example, Süsal et al., 2013, Transfus Med Hemother 40, 190-195, which is hereby incorporated by reference. For instance, the Luminex-supported single antigen bead (L-SAB) test allows for the characterization of human leukocyte antigen (HLA) antibody specificities. In such a flow cytometric method, microbeads coated with recombinant single antigen HLA molecules are employed in order to differentiate antibody reactivity in two reaction tubes against 100 different HLA class I and 100 different HLA class II alleles. An approximation of the strength of antibody reactivity is derived from the mean fluorescence intensity (MFI) and in some embodiments this serves as features in the present disclosure. In addition to antibody reactivity against HLA-A, -B, -C, -DR and -DQB antigens, L-SAB is capable of detecting antibodies against HLA-DQA, -DPA, and -DPB antigens. In some embodiments, other Luminex kits are used for detection of non-HLA antibodies in order to derive values for one or more features for entities in accordance with the present disclosure. For instance, in some embodiments, major histocompatibility complex class I-related chain A (MICA) and human neutrophil antibodies, and kits that utilize, instead of recombinant HLA molecules, affinity purified pooled human HLA molecules obtained from multiple cell lines (screening test to detect presence of HLA antibodies without further specification) or phenotype panels in which each bead population bears either HLA class I or HLA class II proteins of a cell lines derived from a single individual (panel reactivity, PRA-test) are used to determine value for features for entities in accordance with an embodiment of the present disclosure.

In some embodiments, flow cytometry methods, such fluorescent cell barcoding, is used to obtain values for one or more of the measured features 216. Fluorescent cell barcoding (FCB) enables high throughput, e.g. high content flow cytometry by multiplexing samples of entities prior to staining and acquisition on the cytometer. Individual cell samples (entities) are barcoded, or labeled, with unique signatures of fluorescent dyes so that they can be mixed together, stained, and analyzed as a single sample. By mixing samples prior to staining, antibody consumption is typically reduced 10 to 100-fold. In addition, data robustness is increased through the combination of control and treated samples, which minimizes pipetting error, staining variation, and the need for normalization. Finally, speed of acquisition is enhanced, enabling large profiling experiments to be run with standard cytometer hardware. See, for example, Krutzik, 2011, "Fluorescent Cell Barcoding for Multiplex Flow Cytometry," Curr Protoc Cytom Chapter 6: Unit 6.31, which is hereby incorporated by reference.

In some embodiments, metabolomics is used to obtain values for one or more of the features 216 that are observed for an entity or a plurality of entities. Metabolomics is a systematic evaluation of small molecules in order to obtain biochemical insight into disease pathways. In some embodiments, such metabolomics comprises evaluation of plasma metabolomics in diabetes (Newgard et al., 2009, "A branched-chain amino acid-related metabolic signature that differentiates obese and lean humans and contributes to insulin resistance," Cell Metab 9: 311-326, 2009) and ESRD (Wang, 2011, "RE: Metabolite profiles and the risk of developing diabetes," Nat Med 17: 448-453). In some embodiments, urine metabolomics is used to obtain values for one or more of the features. Urine metabolomics offers a wider range of measurable metabolites because the kidney is responsible for concentrating a variety of metabolites and excreting them in the urine. In addition, urine metabolomics may offer direct insights into biochemical pathways linked to kidney dysfunction. See, for example, Sharma, 2013, "Metabolomics Reveals Signature of Mitochondrial Dysfunction in Diabetic Kidney Disease," J Am Soc Nephrol 24, 1901-12, which is hereby incorporated by reference.

In some embodiments, mass spectrometry is used to obtain values for one or more of the measured features 216. For instance, in some embodiments, protein mass spectrometry is used to obtain values for one or more of the measured features. In particular, in some embodiments, biochemical fractionation of native macromolecular assemblies within entities followed by tandem mass spectrometry is used to obtain values for one or more of the measured features. See, for example, Wan et al., 2015, "Panorama of ancient metazoan macromolecular complexes," Nature 525, 339-344, which is hereby incorporated by reference. Tandem mass spectrometry, also known as MS/MS or MS2, involves multiple steps of mass spectrometry selection, with some form of fragmentation occurring in between the stages. In a tandem mass spectrometer, ions are formed in the ion source and separated by mass-to-charge ratio in the first stage of mass spectrometry (MS1). Ions of a particular mass-to-charge ratio (precursor ions) are selected and fragment ions (product ions) are created by collision-induced dissociation, ion-molecule reaction, photodissociation, or other process. The resulting ions are then separated and detected in a second stage of mass spectrometry (MS2). In some embodiments the detection and/or presence of such ions serve as the one or more of the measured features.

In some embodiments, the features 216 that are observed for an entity or a plurality of entities are post-translational modifications that modulate activity of proteins within a cell. In some such embodiments, mass spectrometric peptide sequencing and analysis technologies are used to detect and identify such post-translational modifications. In some embodiments, isotope labeling strategies in combination with mass spectrometry are used to study the dynamics of modifications and this serves as a measured feature. See for example, Mann and Jensen, 2003 "Proteomic analysis of post-translational modifications," Nature Biotechnology 21, 255-261, which is hereby incorporated by reference. In some embodiments, mass spectrometry is user to determine splice variants in entities, for instance, splice variants of components within entities, and such splice variants and the detection of such splice variants serve as measured features. See for example, Nilsen and Graveley, 2010, "Expansion of the eukaryotic proteome by alternative splicing, 2010, Nature 463, 457-463, which is hereby incorporated by reference.

In some embodiments, imaging cytometry is used to obtain values for one or more of the measured features 216. Imaging flow cytometry combines the statistical power and fluorescence sensitivity of standard flow cytometry with the spatial resolution and quantitative morphology of digital microscopy. See, for example, Basiji et al., 2007, "Cellular Image Analysis and Imaging by Flow Cytometry," Clinics in Laboratory Medicine 27, 653-670, which is hereby incorporated by reference.

In some embodiments, electrophysiology is used to obtain values for one or more of the measured features 216. See, for example, Dunlop et al., 2008, "High-throughput electrophysiology: an emerging paradigm for ion-channel screening and physiology," Nature Reviews Drug Discovery 7, 358-368, which is hereby incorporated by reference.

In some embodiments, proteomic imaging/3D imaging is used to obtain values for one or more of the measured features 216. See for example, United States Patent Publication No. 20170276686 A1, entitled "Single Molecule Peptide Sequencing," which is hereby incorporated by reference. Such methods can be used to large-scale sequencing of single peptides in a mixture from an entity, or a plurality of entities at the single molecule level.

Assay Parameters

As described herein with reference to FIG. 3, in some embodiments, each feature measurement 216 is obtained in replicate, e.g., each condition (e.g., exposure of each cell context to each compound) is performed more than once and each feature measurement is obtained from each instance of the condition. In some embodiments, feature measurements 216 are obtained from at least two, three, four, five, or more instances of every condition, e.g., experimental conditions are prepared in two or more replicates.

Similarly, as described herein with reference to FIG. 3, in some embodiments, each compound 232 is exposed to each cell context at a plurality of concentrations. In some embodiments, each compound 232 is exposed to each cell context using at least two, three, four, five, or more concentrations. Similarly, in some embodiments, each feature measurement 216 is obtained at each concentration in replicate.

Accordingly, in some embodiments, a first amount of the respective compound is tested in a first subset of the plurality of instances of the cell context, and a second amount of the respective compound is tested in a second subset of the plurality of instances of the cell context (422). For example, as described with respect to FIG. 3, each cell context is exposed to each concentration of each compound in a plurality of replicates, e.g., at least two times each, at least three times each, at least four times each, at least five times each, or more. In some embodiments, each cell context is exposed to each concentration of each compound in the same number of replicates. In some embodiments, each cell context is exposed to a first concentration of the compounds a different number of times than the cell context is exposed to a second concentration. In one embodiment, the first subset of the plurality of instances is three instances, and the second subset of the plurality of instances is three instances (424). In some embodiments, a third amount of the respective compound is tested in a third subset of the plurality of instances of the cell context (428). In some embodiments, the third subset of the plurality of instances is three instances (430).

With respect to the concentrations of compounds used for any particular instance, the skilled artisan will know how to select a concentration for a given compound. In some embodiments, each compound will be used at the same concentrations. In some embodiments, different compounds will be used at different concentrations, e.g., based upon one or more known or expected property of the compound such as molecular weight, solubility, presence or particular functional groups, known or expected interactions, known or expected toxicity, etc. For example, in some embodiments, where a respective compound is known to be toxic to a cell type used in a particular cell context, the concentration of the compound may be adjusted, e.g., relative to the concentration used for other compounds. Generally, in the methods described herein, a compound will be used at a concentration of between 1 nM and 1 mM. In some embodiments, a compound will be used at a concentration of from 10 nM to 100 µM. In some embodiments, a compound will be used at a concentration of from 100 nM to 10 µM. However, the skilled artisan will know when a compound should be used at a concentration outside of this range.

In some embodiments, where the compounds are tested at multiple concentrations, the multiple concentrations will span at least a two-fold range on concentrations, e.g., 100 nM to 200 nM. In some embodiments, the multiple concentrations will span at least an order of magnitude, e.g., 100 nM to 1 µM. Accordingly, in some embodiments, a first amount of the respective compound is a first concentration of the respective compound, the second amount of the respective compound is a second concentration of the respective compound other than the first concentration, and the third amount of the respective compound is a third concentration of the respective compound other than the first concentration or the second concentration (434). For example, in one embodiment, where at least two concentrations are used, the first amount is 0.3 µM, and the second amount is 1 µM (426). In one embodiment, where a third amount of the respective compound is tested in a third subset of the plurality of instances of the cell context, the third amount is 3 µM (432).

Generally, the time over which a cell context is exposed to a compound is influenced by the particular feature being measured and/or the particular assay from which the feature data is being generated. For example, where the assay being used measures a phenomenon that occurs rapidly following exposure of the cell context to the compound, the cell context does not need to be exposed to the compound for a long period of time prior to measurement of the feature. Conversely, where the assay being used measures a phenomenon that occurs slowly, or after a significant delay, following exposure of the cell context to the compound, a longer incubation time should be used prior to measuring the feature.

In some embodiments, e.g., where latent features are being extracted from a cell context, the time over which the cell context is exposed to a compound prior to measurement is determined stochastically. In some embodiments, the time over which the cell context is exposed to a compound prior to measurement is determined based on experience or trial and error with a particular assay or phenomenon. In one embodiment, exposure of the amount of the respective compound to the plurality of instances of the cell type is for at least one hour prior to obtaining the measurement (452). In some embodiments, the measurement is obtained by cellular imaging, e.g., using fluorescent labels (e.g., cell painting) or using native imaging, as described herein and known to the skilled artisan. In some embodiments, exposure of the amount of the respective compound to the plurality of instances of the cell type is for at least one hour prior to obtaining an image (e.g., an image of a multiwell plate 302).

In some embodiments feature data is acquired using an automated cellular imaging system (e.g., ImageXpress Micro, Molecular Devices), where cell contexts have been arranged in multiwell plates (e.g., 384-well plates) after they have been stained with a panel of dyes that emit at different discrete wavelengths (e.g., Hoechst 33342, Alexa Fluor 594 phalloidin, etc.) and exposed to a perturbation. In some embodiments the cell contexts are imaged with an exposure that is a determined by the marker dye used (e.g., 15 ms for Hoechst, 1000 ms for phalloidin), at 20× magnification with 2× binning. For each well, in some embodiments the optimal focus is found using laser auto-focusing on a particular dye channel (e.g., the Hoechst channel). In some embodiments the automated microscope is then programmed to collect a z-stack of 32 images (z=0 at the optimal focal plane, 16 images above the focal plane, 16 below) with 2 µm between slices. In some embodiments each well contains several thousand cells in them, and thus each digital representation of a well captured by a camera represents several thousand cells in each of several different wells. In some embodiments, segmentation software is used to identify individual cells in the digital images and moreover various components (e.g., cellular components) within individual cells. Once the cellular components are segmented and identified, mathematical transformations are performed on these components on order to obtain the measurements of features.

Collection of feature data for a compound library (e.g., step 102 in method 100) continues until all data is collected for each instance of the plurality of cell contexts exposed to respective compounds in the plurality of compounds. Accordingly, in some embodiments, the obtaining step is repeated (462) for each cell context in the plurality of cell contexts, thereby obtaining for each respective compound in the plurality of compounds, a plurality of vectors (e.g., generating (106) multi-dimensional vectors based on measurements of each test instance in a cell contexts for each compound, in method 100), each vector in the plurality of vectors for the plurality of features across a different cell context in the plurality of cell contexts.

Normalization

In some embodiments, the feature measurements 216, e.g., acquired from one or more multiwell plates as illustrated in FIG. 3, are normalized against one or more control instances, e.g., to account for background in the feature measurement (e.g., as represented in step 104 of method 100, illustrated in FIG. 1, which may be performed before or after construction of a multi-dimensional vector). In some embodiments, the one or more control instances are cell contexts that are not exposed to any compound. As such, in some embodiments, each element 216 of a vector that represents a measured feature is determined through an independent normalization process using measurements of the same feature from the control set (e.g., control instance). In other words, the values of a first feature that will collectively (e.g., as an average or other measure of central tendency of these value) serve as a first element in a vector for a compound are normalized in a manner that is independent of the way the values of a second feature that will serve as a second element in a vector for a compound are normalized. Such normalization generally makes use of the values for the corresponding feature from the control instances.

Accordingly, in some embodiments, a subset of the wells in the plurality of wells in each multi-well plate in the plurality of multi-well plates include an aliquot of cells of the cell context that have not been exposed to the respective compound, and the measurement of the different feature in the plurality of features, across the plurality of instances of the cell context that has been exposed to the amount of the respective compound, is normalized by one or more instances of the wells in the subset of wells that contain the cell context and have not been exposed to a respective compound (control instance), e.g., by a mean of the different feature measured across the instances of the wells in the subset of wells that contain the cell context that have not been exposed to the respective compound (436).

In some embodiments, the normalization of the different feature is achieved using the mean of the different feature measured across the instances of the wells in the subset of the wells that contain the cell context that have not been exposed to the respective compound by a method that includes: a) subtracting (i) the mean of the different feature measured across the instances of the wells in the subset of wells that contain the cell context that have not been exposed to the compound (control instance) from (ii) each measurement of the different feature across the plurality of instances of the cell context upon exposure of the amount of the respective compound, and b) dividing the measurement of the different feature across the plurality of instances of the cell context upon exposure of the amount of the respective compound by a standard deviation of the different feature measured across the instances of the wells in the subset of wells that contain the cell context that have not been exposed to the compound (438).

In some embodiments, the normalization of the different feature is achieved using the standard deviation of the different feature measured across the instances of the wells in the subset of the wells that contain the cell context that have not been exposed to the respective compound by dividing the measurement of the different feature across the plurality of instances of the cell context upon exposure of the amount of the respective compound by a standard deviation, two standard deviations, or three standard deviations of the different feature measured across the instances of the wells in the subset of wells that contain the cell context that have not been exposed to the compound.

In some embodiments, the normalization of the different feature is achieved using a measure of dispersion of the different feature measured across the instances of the wells in the subset of the wells that contain the cell context that have not been exposed to the respective compound by dividing the measurement of the different feature across the plurality of instances of the cell context upon exposure of the amount of the respective compound by the measure of dispersion of the different feature across the instances of the wells in the subset of wells that contain the cell context that have not been exposed to the compound. In some such embodiments, this measure of dispersion is a mean deviation, a standard deviation, a variance, or some multiplication thereof (e.g., 2×mean deviation, 2×standard deviation, 2×variance, etc.).

In some embodiments, the normalization of the different feature is achieved using a measure of central tendency of the different feature measured across the instances of the wells in the subset of the wells that contain the cell context that have not been exposed to the respective compound by a method including: a) subtracting (i) the measure of central tendency of the different feature measured across the instances of the wells in the subset of wells that contain the cell context that have not been exposed to the compound (control instances) from (ii) each measurement of the different feature across the plurality of instances of the cell context upon exposure of the amount of the respective compound, and b) dividing the measurement of the different feature across the plurality of instances of the cell context upon exposure of the amount of the respective compound by a measure of dispersion of the different feature measured across the instances of the wells in the subset of wells that contain the cell context that have not been exposed to the compound. In some such embodiments, the measure of central tendency is an arithmetic mean, weighted mean, midrange, midhinge, trimean, Winsorized mean, median, or mode. In some such embodiments, the measure of dispersion of the different feature measured across the instances of the wells in the subset of wells that contain the cell context that have not been exposed to the compound (control instance) is a mean deviation, a standard deviation, a variance, or some multiplication thereof (e.g., 2×mean deviation, 2×standard deviation, 2×variance) of the different feature measured across the instances of the wells in the subset of wells that contain the cell context that have not been exposed to the compound.

Intra-Compound Pruning

In some embodiments, a first sub-set of compounds is selected based on a similarity between multi-dimensional vectors (e.g., a geometric relationship between instance vectors) corresponding to the same compound (e.g., as represented by step 108 in method 100). In some embodiments, this step is used to eliminate compounds from the starting library that do not provide internally consistent cellular effects, e.g., across different instances of exposure of a respective cell context to the compound, because internal inconsistency indicates that the effects are most likely noise that is not biologically relevant. In some embodiments, instance vectors corresponding to all instances of a cell context that is exposed to a respective compound are compared to each other, e.g., regardless of the concentration of the compound exposed to the cell context, and compounds that cause significantly varying effects (e.g., as identified through a geometric relationship between the instance vectors) are not selected for the focused compound library. In some embodiments, only instance vectors corresponding to all instances of a cell context that is exposed to the same concentration of a respective compound are compared to each other, and compounds that cause significantly varying effects (e.g., as identified through a geometric relationship between the instance vectors) are not selected for the focused compound library.

Accordingly, in some embodiments, method 400 includes, for each respective compound 232 in the plurality of compounds, and for each respective cell context in the plurality of cell contexts, computing a similarity metric (e.g., vector angle, angular distance, distance between vectors, vector magnitude, Minkowski distance, Braycurtis distance, Canberra distance, etc.) between each instance vector representing the respective compound in the respective cell context thereby forming a distribution of similarity metrics for the respective cell context and determining a similarity statistic for the distribution of similarity metrics for the respective compound for the respective cell context. Accordingly, in some embodiments, the method then includes eliminating any compound from the plurality of compounds that fails a similarity metric distribution threshold for the calculated similarity statistic for each cell context in the plurality of cell contexts, or for a predetermined number of cell contexts in the plurality of cell contexts, e.g., as represented by step 117 in method 100. In some embodiments, the similarity statistic is a non-parametric statistic, e.g., derived from a Mann-Whitney U test or Kruskal Wallis test. In some embodiments, the similarity statistic is a parametric statistic, e.g., derived from a T-test or ANOVA test. In some embodiments, the similarity statistic is a p-value relative to a null distribution. In one embodiment, the p-value distribution threshold is 0.05. In other embodiments, the p-value distribution threshold is 0.005, 0.01, 0.02, 0.03, 0.04, 0.05, 0.06, 0.07, 0.08, 0.09, 0.1, or higher.

In some embodiments, rather than using a fixed similarity threshold for selecting compounds to be removed, the distribution similarity statistics are ranked ordered and a predetermined number of compounds, e.g., having the widest distributions, are removed from the compound library (e.g., are not selected from the smart compound library). In this fashion, a user can prune the compound library to a desired number of compounds using intra-compound vector comparisons.

In some embodiments, the similarity metric used to compare N-dimensional vectors is an angle formed between the vectors in N-dimensional space. The angle θ(u, v) between vectors u and v can be determined based on the relationship between the dot product of the vectors, the lengths of the vectors, and the angle between the vectors, e.g., where:

$$\cos\Theta(u, v) = \frac{u \cdot v}{|u| \cdot |v|}$$

Accordingly, in some embodiments, method 400 includes for each respective compound in the plurality of compounds, for each respective cell context in the plurality of cell contexts, computing (476) an angle between each instance vector representing the respective compound in the respective cell context thereby forming a distribution of angles for the respective compound for the respective cell context and determining a distribution statistic (e.g., a non-parametric statistic, e.g., derived from a Mann-Whitney U test or Kruskal Wallis test, or a parametric statistic, e.g., derived from a T-test or ANOVA test) for the distribution of angles for the respective compound for the respective cell context. Accordingly, in some embodiments, the method then includes eliminating any compound from the plurality of compounds that fails an angle distribution threshold for each cell context in the plurality of cell contexts, e.g., where the angle distribution threshold for one or more respective cell contexts in the plurality of contexts is not satisfied. In some embodiments, the angle distribution statistic is a p-value distribution statistic relative to a null distribution. In one embodiment, the p-value distribution threshold is 0.05. In other embodiments, the p-value distribution threshold is 0.005, 0.01, 0.02, 0.03, 0.04, 0.05, 0.06, 0.07, 0.08, 0.09, 0.1, or higher.

In some embodiments, the similarity metric used to compare N-dimensional vectors is a distance between the vectors in N-dimensional space. The distance d(u, v) between vectors u and v can be determined based on application of the Pythagorean theorem in N-dimensional space having n dimensions, e.g., where:

$$d(u,v) = \sqrt{\sum_{i=1}^{n}(u_i - v_i)^2}$$

Accordingly, in some embodiments, method 400 includes for each respective compound in the plurality of compounds, for each respective cell context in the plurality of cell contexts, computing a distance between each instance vector representing the respective compound in the respective cell context thereby forming a distribution distances for the respective compound for the respective cell context and determining a distribution statistic (e.g., a non-parametric statistic, e.g., derived from a Mann-Whitney U test or Kruskal Wallis test, or a parametric statistic, e.g., derived from a T-test or ANOVA test) for the distribution of distances for the respective compound for the respective cell context. Accordingly, in some embodiments, the method then includes eliminating any compound from the plurality of compounds that fails a distance distribution statistic threshold for each cell context in the plurality of cell contexts, e.g., where the distance distribution threshold for one or more respective cell contexts in the plurality of contexts is not satisfied. In some embodiments, the distance distribution statistic is a p-value distribution statistic relative to a null distribution. In one embodiment, the p-value distribution threshold is 0.05. In other embodiments, the p-value distribution threshold is 0.005, 0.01, 0.02, 0.03, 0.04, 0.05, 0.06, 0.07, 0.08, 0.09, 0.1, or higher.

In some embodiments, prior to computing the similarity metric for the multi-dimensional instance vectors, the dimensions of the instance vectors are reduced (e.g., as in step 110 of method 100), thereby obtaining a plurality of dimension-reduced multi-dimensional instance vectors. Dimension reduction reduces the number of variables under consideration (e.g., the elements comprising feature measurements) by determining a smaller set of principal variables. Dimension reduction methodologies include feature selection techniques and feature extraction techniques (e.g., principal component analysis, non-negative matrix factorization, kernel PCA, graph-based kernel PCA, linear discriminant analysis, generalized discriminant analysis, Uniform Manifold Approximation and Projection (UMAP), and use of an autoencoder), as described in more detail below. For a brief review see, for example, Pudil P., Novovičová J. (1998) Novel Methods for Feature Subset Selection with Respect to Problem Knowledge. In: Liu H., Motoda H. (eds) Feature Extraction, Construction and Selection. The Springer International Series in Engineering and Computer Science, vol. 453. Springer, Boston, MA, the content of which is incorporated by reference herein. Advantageously, reducing the dimensions of the instance vectors reduces the processing time required when computing similarity metrics, and improves the performance of machine learning models by removing multi-collinearity, while maintaining as much of the original underlying data (e.g., information from the measured features) as possible.

Accordingly, in some embodiments, method 400 includes reducing (464) a dimension of each instance vector in the plurality of instance vectors using a dimension reduction technique. In some embodiments, the dimension reduction technique is principal component analysis in which a plurality of principal components is identified based on a variance in the measurement of each different feature in the plurality of features, for a cell context in the plurality of cell contexts, across each compound in the plurality of compounds, and each respective instance vector in the plurality of instance vectors for the cell context is re-expressed as a projection of the respective vector onto the plurality of principal components (466). Similarly, in some embodiments, the dimension reduction method includes: (i) application of a kernel function to the respective measurement of each measured different feature in the plurality of features, for a cell context in the plurality of cell contexts, across each compound in the plurality of compounds, thereby deriving a kernel matrix, and (ii) application of principal component analysis to the kernel matrix thereby identifying a plurality of principal components and wherein each respective instance vector in the plurality of instance vectors for the cell context is re-expressed as a projection of the respective combined vector onto the plurality of principal components (474).

In some embodiments, prior to computing the similarity metric for the multi-dimensional instance vectors (e.g., the dimension-reduced multi-dimensional instance vectors), a transformation is applied to the instance vectors to uncorrelated each element of the instance vectors and/or standardizes the variance of each element of the instance vectors. Non-limiting examples of methodologies useful for decorrelating and/or standardizing variance include whitening transformations, decorrelation transformations, standardization transformations, and coloring transformations, as described in detail below. In some embodiments, this generates a plurality of multi-dimensional covariance vectors from the plurality of dimension-reduced multi-dimension vectors, e.g., in which each element of the vectors is scaled to have its sample variance equal to one.

Accordingly, in some embodiments, each respective principal component analysis in the plurality of principal components is associated with a corresponding eigenvalue, and each respective principal component in the plurality of principal components is normalized by the square root of the corresponding eigenvalue prior to using the plurality of principal components to re-express each respective vector in the plurality of vectors (468), e.g., thereby forming a plurality of multi-dimensional covariance vectors. For a review of data whitening techniques see, for example, Agnan Kessy, Alex Lewin & Korbinian Strimmer (2018) Optimal Whitening and Decorrelation, The American Statistician, DOI: 10.1080/00031305.2016.1277159, the content of which is incorporated by reference herein.

In some embodiments, prior to computing the similarity metric for the multi-dimensional instance vectors (e.g., the multi-dimensional covariance instance vectors), the elements of the instance vectors (e.g., elements of the multi-dimensional covariance instance vectors) are normalized against one or more control instances, e.g., to account for background in the feature measurement and/or to control for variability across instances (e.g., across experiments, batches, etc.) (e.g., as represented in step 114 of method 100, illustrated in FIG. 1). In some embodiments, the one or more control instances are cell contexts that are not exposed to any compound. Accordingly, in some embodiments, a subset of the wells in the plurality of wells in each multi-well plate in the plurality of multi-well plates comprise an aliquot of cells of the cell context that have not been exposed to the respective compound, and each respective element in the respective vector is normalized by a measure of central tendency (e.g., mean, average) of the respective element in the vectors representing the subset of the wells that contain the cell context that have not been exposed to the respective compound prior to applying the dimension reduction technique (470). That is, in some embodiments, the feature elements measured from the test instances are normalized by the corresponding feature elements in the control instances prior to dimension-reducing (e.g., using principal component analysis) the feature elements measured from the test instances.

In some embodiments, each respective element in the respective instance vector is normalized by a mean, or some other measure of central tendency, of the respective element in the vectors representing the subset of the wells that contain the cell context (but have not been exposed to the respective compound) by a method including: a) subtracting the mean, or some other measure of central tendency, of the respective element across the vectors representing the subset of the wells that contain the cell context that have not been exposed to the respective compound, and b) dividing by a standard deviation, or some other measure of dispersion, of the respective element in the vectors representing the subset of the wells that contain the cell context that have not been exposed to the compound control (472). In some embodiments, each element in the respective instance vector is normalized using control data using any of the methods of normalization discussed above in the section entitled "normalization" prior to performing the dimension reduction technique.

Inter-Compound Pruning

In some embodiments, a second sub-set of compounds is selected based on geometric relationships between multi-dimensional compound vectors (e.g., multi-dimensional vectors corresponding to all instances of all cell contexts exposed to a respective compound, as formed in step 120 of method 100) corresponding to different compounds (e.g., as represented by step 118 in method 100). In some embodiments, this step is used to create a smaller, "smart" compound library that maintains the majority of the diversity of effects provided by the original compound library, e.g., by eliminating compounds that have highly similar effects to other compounds that are selected for the second sub-set of compounds. In this fashion, the second sub-set of compounds is representative of the larger set of compounds. (e.g., either the original library of compounds or the first sub-set of compounds that has already been reduced by removing compounds with internally inconsistent effects).

In some embodiments, the compound vectors include, or are accompanied by, additional information about the compound, e.g., information that was not measured in an assay. For example, in some embodiments, this additional information includes annotated tags about the compound, e.g., mechanisms of action (MOA) annotations for the compound. For instance, the vector may include, or be accompanied by, a known mechanism of action, a chemical structure, a bioassay outcome, any other non-cell-based assay result described herein, or other structural characteristic of the molecule (e.g., an identity of a functional group within the compound). Available information about a chemical compound that can be incorporated into, or accompany, a multi-dimensional vector can be found, for example, in publicly available electronic databases, such as ChEMBL (see, Gaulton, A., et al., Nucleic Acids Res. 40:D1100-D1107 (2012)), PubChem (see, Wang, Y., et al., Nucleic Acids Res. 40:D400-D412 (2012)), and ZINC 15 (see, Sterling and Irwin, J. Chem. Inf. Model, 55:2324-37 (2015)). In some embodiments, the multi-dimensional includes a two-dimensional fingerprint of the corresponding compound (e.g., an extended-connectivity fingerprint "ECFP" which are described in Rogers and Hahn, "Extended-connectivity fingerprints," 2010, Journal of Chemical Information and Modeling 50, no. 5, pp. 742-754, and on the Internet at docs.chemaxon.com/display/docs/Extended+Connectivity+Fingerprint+ECFP, accessed Sep. 14, 2018, each which is hereby incorporated by reference in its entirety) or a chemical hashed fingerprint of the corresponding compound (e.g., as described on the Internet at https://docs.chemaxon.com/display/docs/Chemical+Hashed+Fingerprint, accessed Sep. 14, 2018, is hereby incorporated by reference in its entirety).

In some embodiments, the second sub-set of compounds is selected from the original library of compounds, e.g., after measuring the features of the plurality of test instances in one or more cell context for each compound in the test compound library (e.g., as represented in step 102 of method 100), multi-dimensional compound vectors are generated based on all feature measurements from all instances of all cell contexts that are exposed to a representative compound in the compound library (e.g., as represented in step 120 of method 100). In some embodiments, prior to generating the multi-dimensional compound vectors, feature measurements are normalized against control instances, e.g., as described above with respect to intra-compound pruning methodologies and represented in step 104 of method 100). In some embodiments, the multi-dimensional compound vectors are dimension reduced (e.g., as described with respect to multi-dimensional instance vectors above and represented in step 110 of method 100), uncorrelated and/or variance standardized (e.g., as described with respect to multi-dimensional instance vectors above and represented in step 112 of method 100), and/or normalized against elements of control vectors representing control instances of the cell context (e.g., as described with respect to multi-dimensional instance vectors above and represented in step 114 of method 100).

In some embodiments, e.g., where the second sub-set of compounds is selected from the original library of compounds, multi-dimensional compound vectors are generated by first constructing multi-dimensional instance vectors based on feature measurements from individual instances of a cell context that is exposed to a compound in the test library, e.g., as described above with respect to intra-compound pruning methodologies and represented in step 106 of method 100. In some embodiments, the multi-dimensional instance vectors are dimension reduced (e.g., as represented in step 110 of method 100), uncorrelated and/or variance standardized (e.g., as represented in step 112 of method 100), and/or normalized against elements of control vectors representing control instances of the cell context (e.g., as represented in step 114 of method 100), e.g., as described above with respect to intra-compound pruning methodologies. Then, all multi-dimensional instance vectors for each respective compound are combined to form a single multi-dimensional compound vector for that compound (e.g., corresponding to features measured from all instances of all cell contexts exposed to the compound), such that a plurality of multi-dimensional compound vectors are formed, each corresponding to a different compound in the plurality of compounds.

In some embodiments, the second sub-set of compounds is selected from a first sub-set of the original library of compounds, e.g., that was reduced using the intra-compound reduction methods described above for removing compounds with internally inconsistent effects (e.g., as represented by set 108 of method 100). In some embodiments, the multi-dimensional instance vectors generated for the intra-compound reduction step are used for the inter-compound reduction methods described herein, e.g., multi-dimensional instance vectors as generated in step 106 of method 100, dimension-reduced instance vectors as generated in step 110 of method 100, multi-dimensional instance covariance vectors as generated in step 112 of method 100, or standardized multi-dimensional instance covariance vectors as generated in step 114 of method 100. That is, in some embodiments, each multi-dimensional instance vector corresponding to an instance of a cell context for a respective compound are combined into a multi-dimensional compound vector for the inter-compound reduction methods described herein.

Accordingly, in some embodiments, method 400 includes combining (478), for each respective compound in the plurality of compounds, the plurality of vectors (e.g., multi-dimensional instance vectors, e.g., as formed in step 106, 110, 112, or 114 of method 100) for the respective compound (e.g., for all compounds in the original compound library or for all compounds in a reduced compound library, e.g., as formed in step 108 of method 100) to form a combined vector for the respective compound (e.g., a multi-dimensional compound vector), thereby forming a plurality of combined vectors (e.g., a plurality of multi-dimensional compound vectors), each combined vector in the plurality of combined vectors representing a different compound in the plurality of compounds (e.g., as represented in step 120 of method 100). In some embodiments, combining the vectors is performed using a predetermined mathematical operation, such as concatenation, addition, mean, etc. In some embodiments, combining the vectors in performed using a learned mathematical operation, e.g., convolution, etc.

In some embodiments, method 400 includes pruning (480) the plurality of compounds (e.g., the original library of compounds or the first sub-set of compounds that has already been reduced by removing compounds with internally inconsistent effects) to the subset of compounds (e.g., the second sub-set of compounds) based on a similarity between respective combined vectors (e.g., multi-dimensional compound vectors) in the plurality of combined vectors corresponding to respective compounds in the plurality of compounds.

In some embodiments, inter-compound pruning includes computing a similarity metric (e.g., vector angle, angular distance, distance between vectors, distance function between pairs, combination of distances, combination of functions of the two compound representations, clustering, such as k-means clustering where one compound from each cluster is selected, etc.) between respective pairs of multi-dimensional compound vectors in the plurality of multi-dimensional compound vectors, identifying two or more respective multi-dimensional compound vectors with a threshold similarity to each other, and eliminating one or more of the identified two of more respective multi-dimensional compound vectors (e.g., but not all of the identified two or more respective multi-dimensional compound vectors) from the plurality of compounds. In this fashion, compounds having similar effects on the tested cell contexts as other compounds are pruned from the compound library, such that the final pruned library represents compounds having diverse effects on the tested cell contexts.

In some embodiments, rather than using a fixed threshold similarity for identifying compounds with similar effects, the similarity metrics are ranked ordered and a predetermined number of compound pairs, e.g., with similarity metrics indicating the highest similarity in effects on the cell contexts, are selected for pruning from the compound library. In this fashion, a user can prune the compound library to a desired number of compounds using inter-compound vector comparisons.

Accordingly, in one embodiment, method 400 includes computing (482) an angle between respective combined vector pairs (e.g., multi-dimension compound vector pairs) in the plurality of combined vectors for all respective pairs of compounds in the plurality of compounds. In some embodiments, the angle θ(u, v) between vectors u and v is determined based on the relationship between the dot product of the vectors, the lengths of the vectors, and the angle between the vectors, e.g., where:

$$\cos\Theta(u, v) = \frac{u \cdot v}{|u| \cdot |v|}$$

Accordingly, in some embodiments, the method further includes identifying a pair of compounds, consisting of a first compound and a second compound, from the computing whose corresponding multi-dimensional compound vectors form an angle falling below a threshold measure, and eliminating one of the compounds from the compound library. In some embodiments, the threshold measure is a smallest angle formed between corresponding multi-dimensional compound vectors, that is, the pair of compounds is identified based on the fact that their corresponding multi-dimensional compound vectors form the smallest angle of any pair of multi-dimensional compound vectors remaining in the compound library.

In one embodiment, the similarity metric used to compare N-dimensional vectors is an angular distance between the vectors in N-dimensional space. In some embodiments, the angular distance $\theta_d(u, v)$ between vectors u and v is computed as:

$$\frac{\sum_i^n A_i B_i}{\sqrt{\sum_{i=1}^n A_i^2} \sqrt{\sum_{i=1}^n B_i^2}}$$

where: $A_i$ is an element i in a first combined vector (e.g., multi-dimensional compound vector u), in the plurality of combined vectors, that represents a first compound in a compound pair, $B_i$ is an element i in a second combined vector (e.g., multi-dimensional compound vector v), in the plurality of combined vectors, that represents a second compound in the compound pair, and n is a number of elements common between the first combined vector and the second combined vector (484). Accordingly, in some embodiments, the method further includes identifying a pair of compounds, consisting of a first compound and a second compound, from the computing whose corresponding multi-dimensional compound vectors have an angular distance between them that falls below a threshold measure, and eliminating one of the compounds from the compound library. In some embodiments, the threshold measure is a smallest angular distance separating the corresponding multi-dimensional compound vectors, that is, the pair of compounds is identified based on the fact that their corresponding multi-dimensional compound vectors are separated by the smallest angular distance of any pair of multi-dimensional compound vectors remaining in the compound library.

In some embodiments, the similarity metric used to compare N-dimensional vectors is a distance between the vectors in N-dimensional space. The distance d(u, v) between vectors u and v can be determined based on application of the Pythagorean theorem in N-dimensional space having n dimensions, e.g., where:

$$d(u,v) = \sqrt{\sum_{i=1}^n (u_i - v_i)^2}$$

Accordingly, in some embodiments, the method further includes identifying a pair of compounds, consisting of a first compound and a second compound, from the computing whose corresponding multi-dimensional compound vectors are separated by a distance falling below a threshold measure, and eliminating one of the compounds from the compound library. In some embodiments, the threshold measure is a smallest distance between the corresponding multi-dimensional compound vectors, that is, the pair of compounds is identified based on the fact that their corresponding multi-dimensional compound vectors are separated by the smallest distance of any pair of multi-dimensional compound vectors remaining in the compound library.

In some embodiments, rather than comparing vector geometry pairwise across the entirety of N-dimensional space, clusters of vectors and/or sectors of N-dimensional space are considered, e.g., such that compounds corresponding to vectors falling within each cluster of vectors or sector in N-dimensional space are more evenly represented in the final library. For example, in some embodiments, compounds are removed from the compound library based on their corresponding vector falling within a clusters or sector in N-dimensional space that is over-represented by vectors. In some embodiments, clusters of vectors or sectors of N-dimensional space are selected for removal of one or more compounds having vectors falling within the cluster or sector and then individual compounds are removed based on comparison (e.g., pairwise comparison) of the geometries of corresponding multidimensional vectors falling within the cluster or sector of N-dimensional space (e.g., without considering the geometry of multi-dimensional vectors falling within other clusters or sectors in N-dimensional space.

In some embodiments, after determining similarity metrics for respective pairs of multi-dimensional compound vectors (e.g., vector angle, angular distance, distance between vectors, distance function between pairs, combination of distances, combination of functions of the two compound representations, clustering, such as k-means clustering where one compound from each cluster is selected, etc.), the method includes identifying (486) a pair of compounds, consisting of a first compound and a second compound, from the computing that has a closest similarity (e.g., such as smallest angle, shortest angular distance, shortest distance, like clustering, etc.). In some embodiments, the method then includes discarding (488) a compound in the pair of compounds identified in the last instance of the identifying. In some embodiments, the discarding is based on a similarity of each compound in the pair of compounds with other compounds, e.g., based on their corresponding multi-dimensional compound vector. For example, in some embodiments, the compound whose compound vector forms a smallest mean angle with respect to the combined vector of each other compound remaining in the plurality of compounds is removed. Similarly, in some embodiments, the compound whose compound vector has the smallest mean angular distance with respect to the combined vector of each other compound remaining in the plurality of compounds is removed.

In some embodiments, the method includes repeating (490) the identifying and the discarding (e.g., as represented in steps 124 and 126 of method 100) until a threshold number of compounds have been pruned from the plurality of compounds or a number of compounds in the subset of compounds satisfies a threshold value. In some embodiments, each iteration of the identifying and discarding of compounds from the compound library is based on the same similarity metric, e.g., angle distances are used to identify all of the most similar compounds. In other embodiments, different iterations of the identifying and discarding are based on different similarity metrics, e.g., in one iteration a first compound corresponding to a compound vector having the smallest angle distance with a compound vector corresponding to a second compound is removed from the compound library, while in a second iteration a third compound corresponding to a compound vector having a smallest distance from a compound vector corresponding to a fourth compound is removed from the compound library.

Dimensional Reduction

In some embodiments, particularly where a large number of features are measured and/or a large number of cell contexts are used, the resulting multi-dimensional instance vectors and/or multi-dimensional compound vectors used for pruning compounds from the compound library are very large, rendering the subsequent computationally taxing. In order to reduce the computational burden, in some embodiments, the multi-dimensional vectors can be dimension reduced, using a statistical feature selection or feature extraction procedure known in the art, for example, principal component analysis, non-negative matrix factorization, kernel PCA, graph-based kernel PCA, linear discriminant analysis, generalized discriminant analysis, and use of an autoencoder. This, in turn, reduces the computational burden of analyzing the data set by compressing the data in order to make the method more computationally efficient, e.g., by allowing the computer to apply an algorithm to the smaller dataset (the dimension-reduced vectors) rather than the full dataset (the original multi-dimensional vectors).

Principle component analysis (PCA) reduces the dimensionality of a multi-dimensional vector by transforming the plurality of elements (e.g., measured elements 216) to a new set of variables (principal components) that summarize the features of the training set. See, for example, Jolliffe, 1986, Principal Component Analysis, Springer, New York, which is hereby incorporated by reference. PCA is also described in Draghici, 2003, Data Analysis Tools for DNA Microarrays, Chapman & Hall/CRC, which is hereby incorporated by reference. Principal components (PCs) are uncorrelated and are ordered such that the kth PC has the kth largest variance among PCs across the observed data for the features. The kth PC can be interpreted as the direction that maximizes the variation of the projections of the data points such that it is orthogonal to the first k-1 PCs. The first few PCs capture most of the variation in the observed data. In contrast, the last few PCs are often assumed to capture only the residual "noise" in the observed data. As such, the principal components derived from PCA can serve as the basis of vectors that are used in accordance with the present disclosure.

Non-negative matrix factorization and non-negative matrix approximation reduce the dimensionality of a multi-dimensional matrix by factoring the matrix into two matrices, each of which have significantly lower dimensionality, but which provide a product having the same, or approximately the same, dimensionality as the original higher-dimensional matrix. See, for example, Lee and Seung, "Learning the parts of objects by non-negative matrix factorization, Nature, 401(6755):788-91 (1999), which is hereby incorporated by reference. See also Dhillon and Sra, "Generalized Nonnegative Matrix Approximations with Bregman Divergences," Advances in Neural Information Processing Systems 18 (NIPS 2005), which is hereby incorporated by reference.

Kernel PCA is an extension of PCA in which N elements of a vector are mapped onto a N-dimensional space using a non-trivial, arbitrary function, creating projections of the elements onto principle components lying on a lower dimensional subspace. In this fashion, kernel PCA is better equipped than PCA to reduce the dimensionality of non-linear data. See, for example, Scholkopf, "Nonlinear Component Analysis as a Kernel Eigenvalue Problem," Neural Computation, 10: 1299-1319 (198), which is hereby incorporated by reference.

Linear discriminant analysis (LDA), like PCA, reduces the dimensionality of a multi-dimensional vector by transforming the plurality of elements (e.g., measured elements 216) to a new set of variables (principal components) that summarize the features of the training set. However, unlike PCA, LDA is a supervised feature extraction method which (i) calculates between-class variance, (ii) calculates within-class variance, and then (iii) constructs a lower dimensional-representation that maximizes between-class variance and minimizes within-class variance. See, for example, Tharwat, A., et al., "Linear discriminant analysis: A detailed tutorial," AI Communications, 30:169-90 (2017), which is hereby incorporated by reference.

Generalized discriminant analysis (GDA), similar to kernel PCA, maps non-linear input elements of multi-dimensional vectors into higher-dimensional space to provide linear properties of the elements, which can then be analyzed according to classical linear discriminant analysis. In this fashion, GDA is better equipped than LDA to reduce the dimensionality of non-linear data. See, for example, Baudat and Anouar, "Generalized Discriminant Analysis Using a Kernel Approach," Neural Comput., 12(10):2385-404 (2000).

Autoencoders are artificial neural networks used to learn efficient data codings in an unsupervised learning algorithm that applies backpropagation. Autoencoders consist of two parts, an encoder and a decoder. The encoder reads an input vector and compress it to a lower-dimensional vector, and the decoder reads the compressed vector and recreates the input vector. See, for example, Chapter 14 of Goodfellow et al., "Deep Learning," MIT Press (2016), which is hereby incorporated by reference.

Yet other dimension reductions techniques known in the art may also be applied to the methods described herein. For example, in some embodiments, subset selection methods are used, which select a set of features to be included in a reduced dimension representation, while discarding other features, e.g., based on optimality criterion in linear regression. See, for example, Draper and Smith, "Applied Regression Analysis," 2d Edition, New York: John Wiley & Sons, Inc. (1981), which is hereby incorporated by reference. Similarly, in some embodiments, discrete methods, in which features are either selected or discarded, e.g., a leaps and bounds procedure, are used. See, for example, Furnival and Wilson, "Regressions by Leaps and Bounds," Technometrics, 16(4):499-511 (1974), which is hereby incorporated by reference. Likewise, in some embodiments, linear regression by forward selection, backward elimination, or bidirectionsl elimination are used. See, for example, Draper and Smith, "Applied Regression Analysis," 2d Edition, New York: John Wiley & Sons, Inc. (1981). In yet other embodiments, shrinkage methods, e.g., methods that reduce/shrink the redundant or irrelevant features in a more continuous fashion are used, e.g., ridge regression, Lasso, and Derived Input Direction Methods (e.g., PCR, PLS).

Correlation Removal and Variance Standardization

In some embodiments, in the case where principal component analysis is used, each element of the multi-dimensional vectors described herein represents a different principal component. As such, the resulting dimension-reduced vector includes principal components that are not normalized, and therefore the initial principal components which necessarily describe the greatest amount of variation have larger values then subsequent principal components. However, it is precisely these subsequent principal components that may have biological significance. Therefore, in some embodiments of the present disclosure the compounds are whitened to make all the principal components equal in value. For instance, in some embodiments, each respective principal component in the plurality of principal components is associated with a corresponding eigenvalue, and each respective principal component in the plurality of principal components is normalized by the square root of the corresponding eigenvalue prior to using the plurality of principal components to reexpress each respective vector in the plurality of vectors. In this way, the initial principal components do not overweight the comparison of vectors. More generally, any whitening transform, that is a linear transform that transforms a vector of random variables (here, the principal components) with a known covariance matrix into a set of new variables whose covariance is the identity matrix, can be used. Accordingly, there are many possible whitening procedures, including without limitation, whitening based on principle component analysis, the Cholesky matrix decomposition, and zero-phase component analysis. See, for example, Kessy A. et al., "Optimal Whitening and Decorrelation," The American Statistician, DOI: 10.1080/00031305.2016.1277159 (2018), which is hereby incorporated by reference.

Selection of Compounds Based on Compound Vector Projection in N-Dimensional Space The systems and methods described herein are used to intelligently select a subset of compounds from a larger test compound library for phenotypic drug discovery. As described herein, the selection is based on geometric relationships between multi-dimensional compound vectors representing a large number of features extracted from cell contexts exposed to respective compounds. Accordingly, the distribution of the projections of each multi-dimensional compound vector in N-dimensional space is representative of the diversity in effects caused by the set of compounds in the test library. Thus, by selecting compounds corresponding to compound vector projections distributed throughout N-dimensional space, the diversity of compound effects in the resulting smart library can be controlled.

For example, the diversity of effects in the resulting smart library can be maximized by selecting compounds corresponding to compound vector projections that are evenly distributed throughout the N-dimensional space. In a similar fashion, certain desired features, e.g., a particular phenotype, activity, toxicity, etc., can be enriched for, or avoided, within the resulting smart compound library by biasing for or against selection of compounds lying within an area of the N-dimensional space corresponding to the particular feature.

Figure 5:
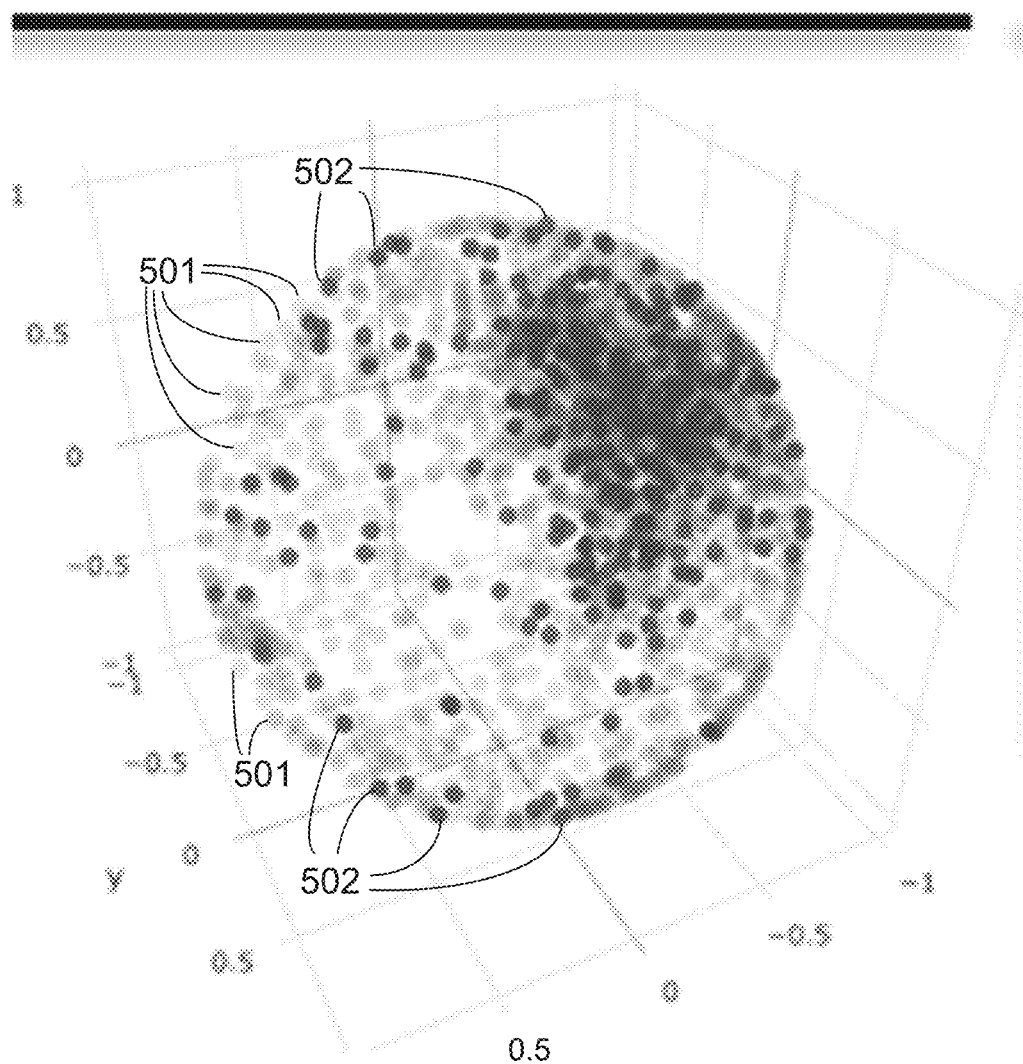
FIG. 5 illustrates selection of a subset of compounds in a plurality of compounds for use as an initial screening library of compounds, e.g., for drug discovery, based on comparison of high-dimensional compound vectors representing measurements of a plurality of different features across a plurality of instances of a plurality of cell contexts, in accordance with various embodiments of the present disclosure.

FIG. 5 illustrates a simplified example of geometric selection of a functionally diverse set of compounds 500 for the generation of a smart compound screening library. Each circle (501, 502) in FIG. 5 represents a multi-dimensional compound vector for a compound in a starting library of compounds, e.g., that may or may not have been previously pruned by considering intra-compound effect consistency (e.g., geometric relationships between multi-dimensional instance vectors, as represented in step 108 of method 100). For simplicity of the example, compound vectors are illustrated in three dimensions in FIG. 5, although they will generally have significantly higher dimensionality in practice. The open, light circles 501 in FIG. 5 represent compound vectors for compounds that were eliminated from the compound library (e.g., they were not selected as part of the final smart compound library), while the closed, dark circles 502 represent compound vectors for compounds that were selected for a final smart compound library.

In some embodiments, as illustrated in FIG. 5, more compounds per unit space are selected from areas within the N-dimensional space that are more densely populated with compound vectors than are selected from areas within the N-dimensional space that are more sparsely populated with compound vectors. For example, as illustrated in FIG. 5, compound vectors corresponding to the selected compounds, as represented by the closed, dark circles 502, are distributed about the three-dimensional phenotypic space in a fashion representative of the overall distribution of all compound vectors (e.g., corresponding to selected and not selected compounds). For instance, more compounds having vector projections lying within the top, right quadrant of the three-dimensional space are selected than compounds having vector projections in the lower, left quadrant of the space, because more total vector projections are present within the upper, right quadrant of the vector space.

In some embodiments, the distribution of compound vectors corresponding to selected compounds is substantially consistent throughout the N-dimensional space, e.g., regardless of whether certain areas within the N-dimensional space are more densely populated with projections of compound vectors than are other areas within the N-dimensional space. For instance, under such a scheme, the compound vectors corresponding to selected compounds in FIG. 5 would be distributed more evenly between the respective quadrants of the vector space, despite that more compound vector projections lie within the upper, right quadrant of vector space illustrated in FIG. 5 than the other quadrants.

Accordingly, in some embodiments, additional constraints are placed upon the selection, or rather the elimination, of compounds from the compound library during inter-compound pruning (e.g., as represented in step 118 of method 100). That is, elimination of compounds purely based on identifying respective compound pairs having vectors with a greatest similarity metric (e.g., smallest angle) will tend to produce reduced compound libraries having compound vector projections that are more evenly distributed throughout N-dimensional vector space, which underrepresent compound diversity within areas of the N-dimensional space that are more densely populated with compound vectors and over-represent compound diversity within areas of the N-dimensional space that are more sparsely populated.

In some embodiments, such constraints include a term that accounts for the overall density of compound vector projections within a given area of the N-dimensional space, e.g., promoting selection of more compounds having vector projections in more densely populated areas of the N-dimensional space and fewer compounds having compound vector projections is more sparsely populated areas of the N-dimensional space, e.g., as illustrated in FIG. 5.

In some embodiments, such constraints include a term that promotes selection of compounds providing a particular phenotype (feature) in one or more cell context and/or compounds with compound vector projections falling within or nearby an area of the N-dimensional space. For example, in some embodiments, a term is used that biases selection for compounds corresponding to compound vectors that include a particular element derived from one or more measured features that is similar to desired feature. In some embodiments, a term is used that biases selection for compounds corresponding to compound vectors having a desired external element, e.g., a MOA tag, a cost point, a functional group, a known toxicity, a known activity, etc. In some embodiments, a term is used that selects all compounds with compound vectors falling within a particular cluster or sector in N-dimensional space. In some embodiments, such constraints include a term that weighs for selection of compounds of a certain feature class.

In some embodiments, such constraints include a term that depresses selection of compounds providing a particular phenotype (feature) in one or more cell context and/or compounds with compound vector projections falling within or nearby an area of the N-dimensional space. For example, in some embodiments, a term is used that biases selection against compounds corresponding to compound vectors that include a particular element derived from one or more measured features that is similar to an undesired feature. In some embodiments, a term is used that biases selection against compounds corresponding to compound vectors having a desired external element, e.g., a MOA tag, a cost point, a functional group, a known toxicity, a known activity, etc. In some embodiments, a term is used that eliminates all compounds having a particular phenotype, e.g., an MOA or a cytotoxicity. In some embodiments, a term is used that eliminates all compounds with compound vectors falling within a particular cluster or sector in N-dimensional space, e.g., centered around a particular phenotype or combination of phenotypes. In some embodiments, such constraints include a term that weights against selection of compounds of a certain feature class.

In some embodiments, such constraints include a term that allows for selection of compounds of different classes with different frequencies. For example, in some embodiments, a first term is used to bias selection of a first class of compounds (e.g., new chemical entities (NCEs)) at a first frequency, e.g., selecting NCEs based on a first density distribution of their corresponding compound vectors in N-dimensional space, and a second term is used to bias selection of a second class of compounds (e.g., biologics) at a second frequency, e.g., selecting biologics based on a second density distribution of their corresponding compound vectors in N-dimensional space. For example, in some embodiments, this is accomplished by weighting determinations of geometric relationships (e.g., distance or angle between vectors) differently for different classes of compounds. In some embodiments, different classes of compounds are selected independently of one another, such that geometric relationships between vectors corresponding to compounds of different classes are not considered, or are considered only when selecting between two identified compounds of a same class.

In some embodiments, such constraints include a term that biases for or against selection of a compound based on a phenotypic distance to one or more identified compounds (e.g., a geometric relationship between the compound vector corresponding to the compound and the compound vectors corresponding to the one or more identified compounds). In some embodiments, the one or more identified compounds are compounds known to have an efficacy and/or known to fall within a particular class of compounds. In this fashion, selection can be biased for selection of compounds that are more likely to provide a similar phenotype, have a similar mechanism of action, and/or fall within a same class of compounds as the one or more identified compounds (e.g., by biasing for selection of compounds with compound vectors that lie near compound vectors for the one or more identified compounds in N-dimensional space). Similarly, selection can be biased for selection of compounds that are more likely to provide different phenotypes, have a different mechanism of action, and/or fall within a different class of compounds as the one or more identified compounds (e.g., by biasing against selection of compounds with compound vectors that lie near compound vectors for the one or more identified compounds in N-dimensional space).

EXAMPLES

A smart compound library having less than a third of the number of compounds as a starting test library was created using intra-compound and inter-compound pruning methods relying on extracted phenotypes from a single high-dimensional assay, as described herein. The starting test compound library used for the validation included 3023 compounds. From these, 167 compounds were manually selected for automatic inclusion in the final, smart library, by virtue of being of special biological or market interest. The 167 compounds were still included in all analysis steps.

The 3023 compounds in the test library were then exposed in triplicate to four cell contexts, HUVEC, U2OS, RPE, Fibroblast, at three different compound concentrations, 0.3 µM, 1 µM, and 3 µM, in a series of 384-well plates, according to the protocol outlined in Bray et al., Nat. Protoc, 11(9):1757-74 (2016). Additionally, samples of each of the cell contexts that were not exposed to any of the compounds were included in triplicate, as control instances.

Briefly, the cells for the cell contexts were grown to near confluence in mammalian cell culture vessels (Corning), according to established growth conditions for each cell line. The cells were detached from the culture vessels, diluted to an appropriate titer (e.g., 50,000 live cells per mL), and then dispensed into the appropriate wells of 384-well plates (e.g., at 1500-3000 cells per well). Compounds from the Moscow test library were then added to the appropriate wells by pin tool or liquid handling, and incubated for 24-48 hours. After incubation, the media was removed from each well of the plates, and then stained (i.e., painted) were painted with five fluorescent dies and fixed with paraformaldehyde, as described in Bray et al., Nature Protocols, 11:1757-74 (2016).

The multi-well plates were then mounted onto an automated microplate handling system associated with an automated ImageXpress Micro XLS epifluorescent microscope (Molecular Devices). Fluorescent images of the multiwell plates were acquired across five fluorescent channels, as given in Table 1, above. CellProfiler biological image analysis software (The Broad Institute) was used to extract per-cell morphology feature data from the Cell Painting images, as well as per-image quality control metrics. In total, 959 features were extracted from each well, resulting in the collection of 3,836 features per instance, across four cell contexts, for each compound at each concentration of the compound.

The feature data acquired from each instance were then combined as elements to form a plurality of instance vectors having 959 dimensions each. Individual elements were then normalized against a mean of the corresponding feature element measured from the replicates of the appropriate control instances by first subtracting (i) the mean of the feature measured across the control instances from (ii) each test measurement of the different feature across the plurality of instances of the cell context upon exposure of the compound, and second dividing (i) the measurement of the feature across the plurality of instances of the cell context upon exposure of the amount of the respective compound by (ii) a standard deviation of the feature measured across the control instances. The dimensions of the normalized vectors were then reduced using principle component analysis. A whitening transformation was used to uncorrelated variables and standardize the variance of all elements in the reduced vectors to 1. Each of the elements were again standardized against the control instances, as described above.

The angle formed between resulting instance vectors in each set of the nine instance vectors corresponding to all three instances of each respective cell context exposed to a respective compound (e.g., three repetitions each at 0.3 µM, 1 µM, and 3 µM), such that each compound corresponded to four sets of nine instance vectors, one for each of the four cell contexts. The statistic for mean cross-validated (CV) angle distribution p-value for each set of nine instance vectors was also calculated, and all compounds whose set of nine instance vectors had a mean CV angle distribution p value of over 0.95 for all 4 contexts were removed from inclusion in the smart compound library. In all, 1219 compounds, approximately 34% of the starting set tested, had four sets of nine instance vectors having a CV angle distribution p value of at least 0.05, and were removed from the candidate set.

The dimension-reduced, whitened, and normalized instance vectors for each of the 1804 remaining compound in the candidate library were concatenated, resulting in 1804 concatenated compound vectors having approximately 800-dimensions, each compound vector representing the approximately 200 reduced-dimensionality feature measurements extracted from each of the four cell contexts. These compound vectors were then used to further prune the compound library by removing compounds that are phenotypically similar across the 800 extracted features.

First, the angles formed between each respective pair of compound vector in the set were calculated, and the pair of compound vectors forming the smallest angle were identified, where at least one of the compound vectors did not represent a compound from the 167 manually selected compounds. Next, it was determined which of the two compound vectors in the pair of identified compound vectors forms the smallest minimum angle with all of the remaining compound vectors corresponding to respective compounds remaining in the candidate set of compounds, and the compound corresponding to that compound vector was eliminated from the compound set. If one of the two compounds was from the set of 167 manually selected compounds, then this compound was always kept. This process was then iterated until only 833 compounds remained in the test compound set. The 167 manually selected compounds were then added to the remaining 833, forming a final smart library of 1000 test compounds.

The resulting smart library was been screened across dozens of different loss-of-function genetic disease models. For example, when screened against loss of the human APC gene in a U2OS cell background, which is a model for familial adenomatous polyposis, five compounds within the smart library were identified as effective for rescuing the disease phenotype, representing 0.5% of the smart test library. Starting from these five compounds, and two compounds demonstrating moderate effectiveness for rescuing the disease phenotype, 34 additional compounds present in the original set of 3023 candidate compounds, but not the set of 1000 test compounds of the smart library, were selected as having compound vectors with high geometric proximity in N-dimensional space to compound vectors for the seven identified compounds in the smart test library. These 34 compounds were then screened for the ability to rescue the loss of APC gene phenotype and an additional 24 compounds were identified as effective, representing 70% of the compounds tested in the expansion screen.

Similarly, when the resulting smart library was screened against loss of the VCL gene in a U2OS cell background, which is a model for familial dilated cardiomyopathy, four compounds within the smart library were identified as effective for rescuing the disease phenotype, representing 0.4% of the smart test library. Starting from these four compounds, and seven compounds demonstrating moderate effectiveness for rescuing the disease phenotype, 31 additional compounds present in the original set of 3023 candidate compounds, but not the set of 1000 test compounds of the smart library, were selected as having compound vectors with high geometric proximity in N-dimensional space to compound vectors for the 11 identified compounds in the smart test library. These 31 compounds were then screened for the ability to rescue the loss of VCL gene phenotype and an additional nine compounds were identified as effective, representing 29% of the compounds tested in the expansion screen.

Finally, when the resulting smart library was screened against loss of the SMN1 gene in a HUVECs background, which is a model for spinal muscular atrophy, two compounds within the smart library were identified as effective for rescuing the disease phenotype, representing 0.2% of the smart test library. Starting from these two compounds, and one compound demonstrating moderate effectiveness for rescuing the disease phenotype, 28 additional compounds present in the original set of 3023 candidate compounds, but not the set of 1000 test compounds of the smart library, were selected as having compound vectors with high geometric proximity in N-dimensional space to compound vectors for the three identified compounds in the smart test library. These 28 compounds were then screened for the ability to rescue the loss of SMN1 gene phenotype and an additional 13 compounds were identified as effective, representing 46% of the compounds tested in the expansion screen.

References Cited and Alternative Embodiments

All references cited herein are incorporated herein by reference in their entirety and for all purposes to the same extent as if each individual publication or patent or patent application was specifically and individually indicated to be incorporated by reference in its entirety for all purposes.

The present invention can be implemented as a computer program product that comprises a computer program mechanism embedded in a nontransitory computer readable storage medium. For instance, the computer program product could contain the program modules shown in any combination of FIGS. 1, 2, 3, and/or described in FIG. 4. These program modules can be stored on a CD-ROM, DVD, magnetic disk storage product, USB key, or any other non-transitory computer readable data or program storage product.

Many modifications and variations of this invention can be made without departing from its spirit and scope, as will be apparent to those skilled in the art. The specific embodiments described herein are offered by way of example only. The embodiments were chosen and described in order to best explain the principles of the invention and its practical applications, to thereby enable others skilled in the art to best utilize the invention and various embodiments with various modifications as are suited to the particular use contemplated. The invention is to be limited only by the terms of the appended claims, along with the full scope of equivalents to which such claims are entitled.

What is claimed is:

1. A computer system for identifying a subset of compounds in a plurality of compounds, the computer system comprising:
   one or more processors;
   a memory; and
   one or more programs, wherein the one or more programs are stored in the memory and are configured to be executed by the one or more processors, the one or more programs including instructions for:

obtaining, for each respective compound in the plurality of compounds, a corresponding vector, thereby obtaining a corresponding plurality of vectors, where the obtaining comprises high throughput screening to measure a plurality of instances in one or more cell context for each compound in the plurality of compounds by imaging each respective instance of the plurality of instances of the cell context, via the high throughput screening, to form a corresponding two-dimensional pixelated image, and wherein the corresponding vector is obtained from a dataset generated from features in the corresponding two-dimensional pixelated image;

repeating the obtaining for each cell context in a plurality of cell contexts, thereby obtaining for each respective compound in the plurality of compounds, a plurality of vectors;

combining, for each respective compound in the plurality of compounds, the plurality of vectors for the respective compound to form a combined vector for the respective compound, thereby forming a plurality of combined vectors, each combined vector in the plurality of combined vectors representing a different compound in the plurality of compounds; and pruning the plurality of compounds to the subset of compounds based on a similarity between respective combined vectors in the plurality of combined vectors corresponding to respective compounds in the plurality of compounds, wherein the subset of compounds comprises a reduced size smart compound library for performing high throughput pharmaceutical drug screening.

2. The computer system of claim 1, wherein:
each respective vector in the corresponding plurality of vectors comprises a corresponding set of elements, and each respective element in the corresponding set of elements comprises a measurement of a different feature in a plurality of features, across a plurality of instances of a cell context in the plurality of cell contexts upon exposure of an amount of the respective compound to the plurality of instances of the cell context using one or more multi-well plates comprising a plurality of wells.

3. The computer system of claim 2, wherein the exposure of the respective compound to the plurality of instances of the cell context is done in the presence of at least five different dyes and wherein the vector for each respective compound in the plurality of compounds includes respective measurements of features in the plurality of features for the cell context in the presence of each of the at least five different dyes.

4. The computer system of claim 2, wherein:
a first amount of the respective compound is tested in a first subset of the plurality of instances of the cell context, and
a second amount of the respective compound is tested in a second subset of the plurality of instances of the cell context.

5. The computer system of claim 2, wherein:
a subset of the wells in the plurality of wells in each multi-well plate in the one or more multi-well plates comprise an aliquot of cells of the cell context that have not been exposed to the respective compound; and
the measurement of the different feature in the plurality of features, across the plurality of instances of the cell context that has been exposed to the amount of the respective compound, is normalized by a mean of the different feature measured across the instances of the wells in the subset of the wells that contain the cell context that have not been exposed to the respective compound.

6. The computer system of claim 2, wherein the one or more programs further include instructions for:
reducing a dimension of each vector in the plurality of vectors using a dimension reduction technique.

7. The computer system of claim 1, wherein the one or more programs further include instructions for:
for each respective compound in the plurality of compounds:
for each respective cell context in the plurality of cell contexts;
computing an angle between each vector representing the respective compound in the respective cell context thereby forming a distribution of angles for the respective compound for the respective cell context; and
determining a distribution p-value for the distribution of angles for the respective compound for the respective cell context; and
eliminating any compound from the plurality of compounds that fails a p-value distribution threshold for each cell context in the plurality of cell contexts.

8. The computer system of claim 1, wherein the pruning the plurality of compounds to the subset of compounds based on the similarity between the combined vectors corresponding to the respective compounds in the plurality of compounds comprises:
computing a geometric relationship between respective combined vector pairs in the plurality of combine vectors for all respective pairs of compounds in the plurality of compounds;
identifying a pair of compounds, consisting of a first compound and a second compound, from the computing that has a closest geometric relationship;
discarding a compound in the pair of compounds identified in the last instance of the identifying that has a closest geometric relationship with respect to a combined vector of another compound remaining in the plurality of compounds; and
repeating the identifying and the discarding until a threshold number of compounds have been pruned from the plurality of compounds or a number of compounds in the subset of compounds satisfies a threshold value.

9. The computer system of claim 8, wherein the geometric relationship between the respective combined vector pairs is weighted based on a property of the first compound and the second compound.

10. The computer system of claim 8, wherein:
the geometric relationship is an angle formed between the respective combined vector pairs; and
the closest geometric relationship with respect to the combined vector of another compound remaining in the plurality of compounds is the smallest angle formed between:
the combined vector for the first compound or the combined vector for the second compound; and
the combined vector for the closest combined vector for another compound remaining in the plurality of compounds.

11. The computer system of claim 8, wherein the geometric relationship between the respective combined vector pairs is an angular distance computed as:

$$\frac{\sum_{i}^{n} A_i B_i}{\sqrt{\sum_{i=1}^{n} A_i^2} \sqrt{\sum_{i=1}^{n} B_i^2}}$$

and wherein:
- $A_i$ is an element i in a first combined vector, in the plurality of combined vectors, that represents a first compound in a compound pair;
- $B_i$ is an element i in a second combined vector, in the plurality of combined vectors, that represents a second compound in the compound pair; and
- n is a number of elements common between the first combined vector and the second combined vector.

12. The computer system of claim 1, wherein a first cell context in the plurality of cell contexts consists of a first cell type and a second cell context in the plurality of cell contexts consist of the first cell type exposed to a perturbing agent.

13. The computer system of claim 1, wherein a first cell context in the plurality of cell contexts consists of a first native cell type and a second cell context in the plurality of cell contexts consist of the first native cell type that has incurred a genetic modification.

14. A method for identifying a subset of compounds in a plurality of compounds, the method comprising:
at computer system comprising one or more processors and a memory:
obtaining, for each respective compound in the plurality of compounds, a corresponding vector, thereby obtaining a corresponding plurality of vectors where the obtaining comprises high throughput screening to measure a plurality of instances in one or more cell context for each compound in the plurality of compounds by imaging each respective instance of the plurality of instances of the cell context, via the high throughput screening, to form a corresponding two-dimensional pixelated image, and wherein the corresponding vector is obtained from a dataset generated from features in the corresponding two-dimensional pixelated image;
repeating the obtaining for each cell context in a plurality of cell contexts, thereby obtaining for each respective compound in the plurality of compounds, a plurality of vectors;
combining, for each respective compound in the plurality of compounds, the plurality of vectors for the respective compound to form a combined vector for the respective compound, thereby forming a plurality of combined vectors, each combined vector in the plurality of combined vectors representing a different compound in the plurality of compounds; and
pruning the plurality of compounds to the subset of compounds based on a similarity between respective combined vector pairs in the plurality of combined vectors corresponding to respective compound pairs in the plurality of compounds wherein the subset of compounds comprises a reduced size smart compound library for performing high throughput pharmaceutical drug screening.

15. The method of claim 14, further comprising:
reducing a dimension of each vector in the plurality of vectors using a dimension reduction technique.

16. The method of claim 14, further comprising:
for each respective compound in the plurality of compounds:
for each respective cell context in the plurality of cell contexts;
computing an angle between each vector representing the respective compound in the respective cell context thereby forming a distribution of angles for the respective compound for the respective cell context; and
determining a distribution p-value for the distribution of angles for the respective compound for the respective cell context; and
eliminating any compound from the plurality of compounds that fails a p-value distribution threshold for each cell context in the plurality of cell contexts.

17. The method of claim 14, wherein the pruning the plurality of compounds to the subset of compounds based on the similarity between the combined vectors corresponding to the respective compounds in the plurality of compounds comprises:
computing a geometric relationship between respective combined vector pairs in the plurality of combine vectors for all respective pairs of compounds in the plurality of compounds;
identifying a pair of compounds, consisting of a first compound and a second compound, from the computing that has a closest geometric relationship;
discarding a compound in the pair of compounds identified in the last instance of the identifying that has a closest geometric relationship with respect to a combined vector of another compound remaining in the plurality of compounds; and
repeating the identifying and the discarding until a threshold number of compounds have been pruned from the plurality of compounds or a number of compounds in the subset of compounds satisfies a threshold value.

18. The method as recited in claim 17, wherein the computing a geometric relationship between respective combined vector pairs in the plurality of combine vectors for all respective pairs of compounds in the plurality of compounds comprises:
weighting the geometric relationship between the respective combined vector pairs based on a property of the first compound and the second compound.

19. The method of claim 17, wherein the computing a geometric relationship between respective combined vector pairs in the plurality of combine vectors for all respective pairs of compounds in the plurality of compounds comprises:
computing the geometric relationship between the respective combined vector pairs is an angular distance computed as:

$$\frac{\sum_{i}^{n} A_i B_i}{\sqrt{\sum_{i=1}^{n} A_i^2} \sqrt{\sum_{i=1}^{n} B_i^2}}$$

and wherein:
- $A_i$ is an element i in a first combined vector, in the plurality of combined vectors, that represents a first compound in a compound pair;
- $B_i$ is an element i in a second combined vector, in the plurality of combined vectors, that represents a second compound in the compound pair; and n is a number of elements common between the first combined vector and the second combined vector.

20. A nontransitory computer readable storage medium and one or more computer programs embedded therein for identifying a subset of compounds in a plurality of compounds, the one or more computer programs comprising instructions which, when executed by a computer system, cause the computer system to perform a method comprising:

obtaining, for each respective compound in the plurality of compounds, a corresponding vector, thereby obtaining a corresponding plurality of vectors, where the obtaining comprises high throughput screening to measure a plurality of instances in one or more cell context for each compound in the plurality of compounds by imaging each respective instance of the plurality of instances of the cell context, via the high throughput screening, to form a corresponding two-dimensional pixelated image, and wherein the corresponding vector is obtained from a dataset generated from features in the corresponding two-dimensional pixelated image;

repeating the obtaining for each cell context in a plurality of cell contexts, thereby obtaining for each respective compound in the plurality of compounds, a plurality of vectors;

combining, for each respective compound in the plurality of compounds, the plurality of vectors for the respective compound to form a combined vector for the respective compound, thereby forming a plurality of combined vectors, each combined vector in the plurality of combined vectors representing a different compound in the plurality of compounds; and pruning the plurality of compounds to the subset of compounds based on a similarity between respective combined vector pairs in the plurality of combined vectors corresponding to respective compound pairs in the plurality of compounds, wherein the subset of compounds comprises a reduced size smart compound library for performing high throughput pharmaceutical drug screening.

* * * * *